US008694263B2

(12) United States Patent
Wigler et al.

(10) Patent No.: US 8,694,263 B2
(45) Date of Patent: Apr. 8, 2014

(54) METHOD OF IDENTIFYING VIRTUAL REPRESENTATIONS OF NUCLEOTIDE SEQUENCES

(75) Inventors: Michael H Wigler, Cold Spring Harbor, NY (US); John Healy, East Northport, NY (US); Robert Lucito, East Meadow, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 1931 days.

(21) Appl. No.: 10/851,779

(22) Filed: May 21, 2004

(65) Prior Publication Data
US 2005/0032095 A1   Feb. 10, 2005

Related U.S. Application Data

(60) Provisional application No. 60/472,845, filed on May 23, 2003, provisional application No. 60/472,843, filed on May 23, 2003.

(51) Int. Cl.
*G01N 33/48* (2006.01)
(52) U.S. Cl.
USPC ............................................................. 702/19
(58) Field of Classification Search
None
See application file for complete search history.

(56) References Cited

U.S. PATENT DOCUMENTS

| | | | |
|---|---|---|---|
| 5,436,142 | A | 7/1995 | Wigler et al. |
| 5,445,934 | A | 8/1995 | Fodor et al. |
| 5,474,796 | A | 12/1995 | Brennan |
| 5,501,964 | A | 3/1996 | Wigler et al. |
| 5,510,270 | A | 4/1996 | Fodor et al. |
| 5,569,753 | A | 10/1996 | Wigler et al. |
| 5,573,933 | A | 11/1996 | Seamark et al. |
| 5,665,549 | A | 9/1997 | Pinkel et al. |
| 5,710,000 | A | 1/1998 | Gingeras et al. |
| 5,721,098 | A | 2/1998 | Pinkel et al. |
| 5,830,645 | A | 11/1998 | Pinkel et al. |
| 5,858,671 | A | 1/1999 | Jones |
| 5,871,917 | A | 2/1999 | Duffy |
| 5,876,929 | A | 3/1999 | Wigler et al. |
| 6,013,431 | A | 1/2000 | Soederlund et al. |
| 6,040,138 | A | 3/2000 | Lockhart et al. |
| 6,100,030 | A | 8/2000 | McCasky Feazel et al. |
| 6,119,120 | A | 9/2000 | Miller |
| 6,153,379 | A | 11/2000 | Caskey et al. |
| 6,159,685 | A | 12/2000 | Pinkel et al. |
| 6,159,713 | A | 12/2000 | Wigler et al. |
| 6,277,606 | B1 | 8/2001 | Wigler et al. |
| 6,287,825 | B1 | 9/2001 | Weissman et al. |
| 6,350,576 | B1 | 2/2002 | Wigler et al. |
| 6,355,423 | B1 * | 3/2002 | Rothberg et al. ............... 435/6 |
| 6,465,482 | B2 | 10/2002 | Mewshaw et al. |
| 6,562,565 | B1 | 5/2003 | Pinkel et al. |
| 2002/0048763 | A1 * | 4/2002 | Penn et al. ....................... 435/6 |
| 2002/0133301 | A1 * | 9/2002 | Hubbell ............................ 702/20 |
| 2004/0137473 | A1 | 7/2004 | Wigler |
| 2004/0197774 | A1 | 10/2004 | Wigler |
| 2005/0196799 | A1 | 9/2005 | Wigler |
| 2005/0266444 | A1 | 12/2005 | Wigler |
| 2007/0207481 | A1 | 9/2007 | Wigler |

FOREIGN PATENT DOCUMENTS

| | | |
|---|---|---|
| AU | 753505 | 10/1998 |
| EP | 0 408 918 | 1/1991 |
| EP | 0721987 A1 | 7/1996 |
| EP | 1032705 | 5/1999 |
| WO | WO 89/10977 | 11/1989 |
| WO | WO/93/06239 | 4/1993 |
| WO | WO/94/11383 | 5/1994 |
| WO | WO/96/07917 | 3/1996 |
| WO | WO/96/19589 | 6/1996 |
| WO | WO/97/22721 | 6/1997 |
| WO | WO 98/28438 | 7/1998 |
| WO | WO 99/05321 | 2/1999 |
| WO | WO 99/23256 | 5/1999 |
| WO | WO 99/39001 | 8/1999 |
| WO | WO 00/24939 A1 | 5/2000 |
| WO | WO 01/83822 A2 | 11/2001 |
| WO | WO/2005/035792 | 4/2005 |
| WO | WO/2007/070640 | 6/2007 |
| WO | WO/2008/016374 A2 | 2/2008 |

OTHER PUBLICATIONS

Li et al. "Selection of optimal DNA oligos for gene expression arrays," Bioinformatics, vol. 17 (2001) pp. 1067-1076.*
Kruglyak et al., "Variation is the spice of life," Nature genetics, vol. 27 (2001) pp. 234-236.*
Shoemaker et al. "Experimental annotation of the human genome using microarray technology," Nature (2001) vol. 409 pp. 922-927.*
Armengol G., et al., "Recurrent gains of 1q, 8 and 12 in the Ewing family of tumours by comparative genomic hybridization," BR J Cancer, vol. 75(10), pp. 1403-1409, 1997.
Barrett MT et al., "Determination of the frequency of loss of heterozygosity in Esophageal Adencarcinoma by Cell Sorting, Whole Genome Amplification and Microsatellite Polymorphisms," Oncogene, vol. 12(9) pp. 1873-1878, 1996.
Barrett M.T., et al., "Genotypic analysis of multiple loci in somatic cells by whole genome amplification," Nucleic Acids Research vol. 23(17), pp. 3488-3492, 1995.
Bishop, D.T., et al., "A Model for RestrictonFragment Length Distributions," AM J Hum Genet, vol. 35, pp. 795-815, 1983.

(Continued)

*Primary Examiner* — Anna Skibinsky
(74) *Attorney, Agent, or Firm* — Gary J. Gershik; Cooper & Dunham LLP

(57) ABSTRACT

The invention provides oligonucleotide probes that can be used to hybridize to a representation of nucleic acid sequences. Compositions containing the probes such as microarrays are also provided. The invention also provides methods of using these probes and compositions in therapeutic, diagnostic, and research applications. Systems and methods for using a word counting algorithm that can quickly and accurately count the number of times a particular string of characters (i.e., nucleotides) appears in a nucleotide sequence (e.g., a genome) are provided. This algorithm can be used to identify the oligonucleotide probes of the invention. The algorithm uses a transform of a genome and an auxiliary data structure to count the number of times a particular word occurs in the genome.

12 Claims, 22 Drawing Sheets

(56) References Cited

OTHER PUBLICATIONS

Burrows, M. et al., *SRC Research Report: A Block-Sorting Lossless Data Compression Algorithm,* Systems Research Center, Digital Equipment Corporation, pp. 1-18, May 10, 1994.
Chang et al., 1998, "Characterization of transformation related genes inoral cancer cells," Oncogene 16:1921-1930.
Cheung, V.G., et al., "Whole Genome Amplification Using a Degenerate Oligomucleotide Primer Allows Hundreds of Genotypes to be Performed on Less than One Nanogram of Genomic DNA," Proc. Natl. Acad. Sci USA, vol. 93(25), pp. 14676-14679, 1996.
Ferragina, P., et al., *Opportunistic Data Structures with Applications,* IEEE Computer Society, 15 pages, 2000.
Ferragina, P., et al., *An Experimental Study of an Opportunistic Index,* Society for Industrial and Applied Mathematics, pp. 269-278, 2001.
Geng et al., 1998, "Isolation of Differentially Expressed Genes by Combining Representational Difference Analysis (RDA) and cDNA Library Arrays," Bio Techniques, vol. 25(3) pp. 434-438.
Guo et al., 1994, "Direct fluorescence analysis of genetic polymorphisms by hybridization with oligonucleotide arrays on glass supports," Nucleic Acids Research, vol. 22(24) pp. 5456-5465.
Hermsen, M.A., et al., "Comparative Genomic Hybridization: A New Tool in Cancer Pathology," Hum Pathol, vol. 27(4), pp. 342-349, 1996.
Houldsworth, J., et al. "Comparative Genomic Hybridization: An Overview," Am J. Pathol, vol. 145(6), pp. 1253-1260, 1994.
Hubank et al., 1994, "Identifying differences in nRNA expression by representational difference analysis of cDNA," Nucleic Acids Research, vol. 22(25) pp. 5640-5648.
Kallioniemi, O.P. et al., "Comparative Genomic Hybridization: A Rapid new Method for Detecting and Mapping DNA Amplification in Tumors," Semin Cancer Biol. vol. 4(1), pp. 41-46, 1993.
Lisitsyn, N., "Representational Difference Analysis: Finding the Differences between Genomes," TIG, vol. 11, pp. 303-307, 1995.
Lisitsyn et al., 1995, "Direct isolation of polymorphic markers linked to a trait by genetically directed representational difference analysis," Nature Genetics, vol. 6 pp. 57-63.
Llsitsyn et al., "Cloning the Differences Between Two Complex Genomes," Science, vol. 259, Feb. 12, 1993.
Lucito et al., Genetic analysis using genomic representations. Proc. Natl Acad Sci USA, vol. 95(8), pp. 4487-4492, Apr. 14, 1998.
Lucito et al., Detecting gene copy number fluctuations in tumor cells by microarray analysis of genomic representations. Genome Res. Nov. 10, 2000(11):1726-36.
Manzini, G., *The Burrows-Wheeler Transform: Theory and Practice,* Lecture Notes in Computer Science, vol. 1672, pp. 34-47, 1999.
Oroskar et al., "Detection of immobilized amplicons by ELISA-like techniques," Clin Chem. vol. 42(9) pp. 1547-1555, Sep. 1996.
Pastinen et al., "Minisequencing: A specific tool for DNA analysis and diagnostics on oligonucleotide arrays," Genome Res. vol. 7(6) pp. 606-614, 1997.
Paunio, T., et al., "Preimplantation Diagnosis by Whole-Genome Amplification, PCT Amplification, and Solid-Phase Minisequencing of Blastomere DNA," Clin Chem, vol. 42(9), pp. 1382-1390, 1996.
Sadakane, K., *A Modified Burrows-Wheeler Transform for Case-Insensitive Search with Application to Suffice Array Compression,* IEEE Computer Society, p. 548, 1999.
Sakamoto, M., et al., "CGH," Nippon Rinsho, vol. 54(4), pp. 501-505, 1996.
Sekizawa, A., et al., "Prenatal Diagnosis of the Fetal RhD Blood Type Using a Single Fetal Nucleated Erythrocyte from Materanl Blood," Obstet Gynecol, vol. 87(4), pp. 501-505, 1996.
Sermon, K., et al., "Adaptation of the Primer Extension Preamplification (PEP) reaction for Preimplantation Diagnosis: Single Blastomere Analysis using Short PEP Protocols," Mol Hum Reprod., vol. 2(3), pp. 209-212, 1996.
Sun, F., et al., "Whole Genome Amplification of Single Cells: Mathematical Analysis of PEP and Tagged PCR," Nucleic Acids Research, vol. 23(15), pp. 3034-3040, 1995.
Tengan, C.H., et al., "Detection and Analysis of Mitochondrial DNA Deletions by Whole Genome PCT;"Biochem Mol. Med, vol. 58(1), pp. 130-134, 1995.
Thompson, C.T., et al., Cytogenetic Profiling using Fluorescence in situ Hybridization (FISH) and Comparative Genomic Hybridization (CGH), J Cell Biochem Suppl., vol. 17G, pp. 139-143, 1993.
Ferragina, P., et al., "An Experimental Study of a Compressed Index," Information Sciences, vol. 135, No. ½, Jun. 2001, pp. 13-28.
Dong, S., et al., "Flexible Use of High-Density Ollgonucleotide Arrays for Single-Nucleotide Polymorphism Discovery and Validation," Genome Research, Cold Spring Harbor Laboratory Press, vol. 11, No. 8, 2001, pp. 1418-1424.
Li, F. et al., "Selection of Optimal DNA Oligos for Gene Expression Arrays," Bioinformatics, Oxford University Press, vol. 17, No. 11, 2001 pp. 1067-1076.
Official Action issued Aug. 21, 2008 in connection with Russian Federation Application No. 2005140278 with English Translation.
Requirement for Restriction/Election issued Feb. 1, 2001 in connection with U.S. Appl. No. 09/561,881, filed May 1, 2000.
Non-Final Office Action issued May 17, 2001 in connection with U.S. Appl. No. 09/561,881, filed May 1, 2000.
Final Office Action issued Feb. 11, 2002 in connection with U.S. Appl. No. 09/561,881, filed May 1, 2000.
Advisory Action issued Jul. 9, 2002 in connection with U.S. Appl. No. 09/561,881, filed May 1, 2000.
Requirement for Restriction/Election issued Jan. 13, 2003 in connection with U.S. Appl. No. 09/561,881, filed May 1, 2000.
Non-Final Office Action issued Apr. 21, 2003 in connection with U.S. Appl. No. 09/561,881, filed May 1, 2000.
Final Office Action issued Nov. 19, 2003 in connection with U.S. Appl. No. 09/561,881, filed May 1, 2000.
Examiner Interview Summary Record issued Jan. 8, 2004 in connection with U.S. Appl. No. 09/561,881, filed May 1, 2000.
Final Office Action issued Jan. 8, 2004 in connection with U.S. Appl. No. 09/561,881, filed May 1, 2000.
Examiner Interview Summary Record issued Feb. 17, 2004 in connection with U.S. Appl. No. 09/561,881, filed May 1, 2000.
Non-Final Office Action issued Mar. 18, 2004 in connection with U.S. Appl. No. 09/561,881, filed May 1, 2000.
Non-Final Office Action issued Aug. 17, 2004 in connection with U.S. Appl. No. 09/561,881, filed May 1, 2000.
Examiner Interview Summary Record issued Feb. 8, 2005 in connection with U.S. Appl. No. 09/561,881, filed May 1, 2000.
Final Office Action issued Apr. 19, 2005 in connection with U.S. Appl. No. 09/561,881, filed May 1, 2000.
Advisory Action issued Sep. 14, 2005 in connection with U.S. Appl. No. 09/561,881, filed May 1, 2000.
Non-Final Office Action issued Dec. 14, 2005 in connection with U.S. Appl. No. 09/561,881, filed May 1, 2000.
Examiner Interview Summary Record issued May 17, 2006 in connection with U.S. Appl. No. 09/561,881, filed May 1, 2000.
Final Office Action issued Aug. 28, 2006 in connection with U.S. Appl. No. 09/561,881, filed May 1, 2000.
Examiner Interview Summary Record issued Jan. 10, 2007 in connection with U.S. Appl. No. 09/561,881, filed May 1, 2000.
Advisory Action issued Mar. 21, 2007 in connection with U.S. Appl. No. 09/561,881, filed May 1, 2000.
Non-Final Office Action issued Jun. 13, 2007 in connection with U.S. Appl. No. 09/561,881, filed May 1, 2000.
Examiner Interview Summary Record issued Dec. 27, 2007 in connection with U.S. Appl. No. 09/561,881, filed May 1, 2000.
Final Office Action issued Mar. 13, 2008 in connection with U.S. Appl. No. 09/561,881, filed May 1, 2000.
Non-Final Office Action issued Mar. 5, 2009 in connection with U.S. Appl. No. 09/561,881, filed May 1, 2000.
Examiner Interview Summary Record issued Apr. 1, 2009 in connection with U.S. Appl. No. 09/561,881, filed May 1, 2000.
Examiner Interview Summary Record issued Apr. 14, 2009 in connection with U.S. Appl. No. 09/561,881, filed May 1, 2000.
Non-Final Office Action issued Jan. 25, 2006 in connection with U.S. Appl. No. 11/094,565, filed Mar. 20, 2005.
Final Office Action issued Aug. 25, 2006 in connection with U.S. Appl. No. 11/094,565, filed Mar. 20, 2005.

(56) References Cited

OTHER PUBLICATIONS

Advisory Action issued Mar. 21, 2007 in connection with U.S. Appl. No. 11/094,565, filed Mar. 20, 2005.
Non-Final Office Action issued Jul. 10, 2007 in connection with U.S. Appl. No. 11/094,565, filed Mar. 20, 2005.
Final Office Action issued Mar. 18, 2008 in connection with U.S. Appl. No. 11/094,565, filed Mar. 20, 2005.
Non-Final Office Action issued Mar. 5, 2009 in connection with U.S. Appl. No. 11/094,565, filed Mar. 20, 2005.
Non-Final Office Action issued Aug. 13, 2004 in connection with U.S. Appl. No. 10/677,396, filed Oct. 1, 2003.
Final Office Action issued Apr. 20, 2005 in connection with U.S. Appl. No. 10/677,396, filed Oct. 1, 2003.
Notice of Abandonment issued Nov. 1, 2005 in connection with U.S. Appl. No. 10/677,396, filed Oct. 1, 2003.
Non-Final Office Action issued Jul. 3, 2007 in connection with U.S. Appl. No. 11/094,388, filed Mar. 30, 2005.
Final Office Action issued Apr. 8, 2008 in connection with U.S. Appl. No. 11/094,388, filed Mar. 30, 2005.
Notice of Allowance Issued Dec. 30, 2008 in connection with U.S. Appl. No. 11/094,388, filed Mar. 30, 2005.
Issue Notification Issued Apr. 22, 2009 in connection with U.S. Appl. No. 11/094,388, filed Mar. 30, 2005.
Heller, R.A. et al. Discovery and analysis of inflammatory disease-related genes using cDNA microarrays. Proc Natl Acad Sci U S A. Mar. 18, 1997;94(6):2150-5.
Lisitsyn, N.A. et al. Comparative genomic analysis of tumors: detection of DNA losses and amplification. Proc Natl Acad Sci U S A. Jan. 3, 1995;92(1):151-5.
Pinkel, D. et al. High resolution analysis of DNA copy number variation using comparative genomic hybridization to microarrays. Nat Genet. Oct. 1998;20(2):207-11.
Pollack, J.R. et al. Genome-wide analysis of DNA copy-number changes using cDNA microarrays. Nat Genet. Sep. 1999;23(1):41-6.
Schena, M. et al. Quantitative monitoring of gene expression patterns with a complementary DNA microarray. Science. Oct. 20, 1995; 270 (5235):467-70.
Shalon, D. et al. A DNA microarray system for analyzing complex DNA samples using two-color fluorescent probe hybridization. Genome Res. Jul. 1996;6(7):639-45.
Shepherd, N.S. et al. Preparation and screening of an arrayed human genomic library generated with the P1 cloning system. Proc Natl Acad Sci U S A. Mar. 29, 1994;91 (7):2629-33.
Vos, P. et al. AFLP: a new technique for DNA fingerprinting. Nucleic Acids Res. Nov. 11, 1995;23(21):4407-14.
Welford, S.M. et al. Detection of differentially expressed genes in primary tumor tissues using representational differences analysis coupled to microarray hybridization. Nucleic Acids Res. Jun. 15, 1998;26(12):3059-65.
Notification of Transmittal of the International Search Report and The Written Opinion of the International Searching Authority, issued Dec. 23, 2005, in connection with International Application No. PCT/US04/016060.
Notification Concerning Transmittal of International Preliminary Report on Patentability, issued Jan. 26, 2006 in connection with PCT/US/04/016060.
Notification Concerning Transmittal of International Application as Published or Republished, issued Mar. 9, 2006 in connection with PCT/US/04/016060.
Examiner's First Report issued Nov. 28, 2008 in connection with Australian Application No. 2004280531.
Notification of First Office Action issued Jun. 29, 2007 in connection with Chinese Application No. 200480020682.7.
Notification of the Second Office Action issued Apr. 3, 2009 in connection with Chinese Application No. 200480020682.7.
Official Action issued May 10, 2007 in connection with Georgian Application No. AP2004009126.
Official Action issued Feb. 21, 2008 in connection with Georgian Application No. AP2004009126.
Search Report issued Oct. 9, 2008 in connection with Georgian Application No. AP2004009126.
Written Opinion, issued Apr. 27, 2006, in connection with Singapore Application No. SG200507408-3.
Written Opinion, issued Feb. 7, 2007, in connection with Singapore Application No. SG200507408-3.
Examination Report issued Nov. 22, 2007, in connection with Singapore Application No. SG200507408-3.
Notification of Grant issued Mar. 31, 2008 in connection with Singapore Application No. SG200507408-3.
Official Action issued Feb. 2008 in connection with Ukrainian Application No. 200512397.
Official Action issued Dec. 5, 2007 in connection with Russian Federation Application No. 2005140278.
Official Action issued Jun. 25, 2008 in connection with Russian Federation Application No. 2005140278.
Examination Report issued Jul. 4, 2007 in connection with New Zealand Application No. 544235.
Examination Report issued May 8, 2008 in connection with New Zealand Application No. 544235.
Examination Report issued Apr. 28, 2009 in connection with New Zealand Application No. 544235.
First Examination Report including Mark-up Claims by the Examiner issued Mar. 15, 2007 in connection with Indian Patent Application No. 235888/KOLNP/2005.
Notification of Grant issued Apr. 16, 2009 in connection with Indian Patent Application No. 235888/KOLNP/2005.
Examiner's Second Report issued Nov. 13, 2009 in connection with Australian Application No. 2004280531.
Examination Report issued Nov. 16, 2009 in connection with New Zealand Application No. 544235.
Decision to Grant issued Nov. 23, 2009 with English translation in connection with Russian Federation Application No. 2005140278.
Official Action issued Nov. 25, 2009 in connection with Canadian Application No. 2,526,810.
Official Action issued Dec. 15, 2009 with English translation in connection with Georgian Application No. AP2004009126.
Amendment in Response to Jun. 29, 2007 Official Action in connection with Chinese Application No. 200480020682.7.
Amendment in Response to Apr. 3, 2009 Official Action in connection with Chinese Application No. 200480020682.7.
Amendment in Response to Oct. 10, 2008 Official Action in connection with Georgian Application No. AP2004009126.
Supplemental Amendment in Response to Oct. 22, 2008 Official Action in connection with Georgian Application No. AP2004009126.
Amendment in Response to Dec. 15, 2009 Official Action in connection with Georgian Application No. AP2004009126.
Amendment in Response to Jun. 25, 2008 Official Action in connection with Russian Federation Application No. 2005140278.
Response to Jul. 4, 2007 Examiner's Report in connection with New Zealand Application No. 544235.
Response to May 14, 2008 Examiner's Report in connection with New Zealand Application No. 544235.
Response to the First Examination Report in connection with Indian Patent Application No. 235888/KOLNP/2005.
Amendment in Response to Aug. 21, 2009 Official Action in connection with Russian Federation Application No. 2005140278.
Oct. 30, 2009 Examiner's Report in connection with New Zealand Application No. 544235.
Response to Oct. 30, 2009 Examiner's Report in connection with New Zealand Application No. 544235.
Response to Examiner's Second Report filed on Feb. 18, 2010 in connection with Australian Application No. 2004280531.
Notice of Acceptance issued on Mar. 10, 2010 in connection with Australian Application No. 2004280531.
Notification of the Decision of Rejection issued Apr. 6, 2010 in connection with Chinese Application No. 200480020682.7.
Remiest for Reexamination in Response to Apr. 6, 2010 Official Action in connection with Chinese Application No. 200460020682.7.

(56) References Cited

OTHER PUBLICATIONS

Supplemental Amendment in Response to Mar. 5, 2009 Office Action and Summary of Mar. 12, 2010 Examiner Interview filed on Mar. 12, 2010 in connection with U.S. Appl. No. 09/561,881, filed May 1, 2000.
Examiner Interview Summary Record issued Mar. 18, 2010 in connection with U.S. Appl. No. 09/561,881, filed May 1, 2000.
Supplemental Amendment in Response to Mar. 5, 2009 Office Action and Summary of Mar. 12, 2010 Examiner Interview filed on Mar. 12, 2010 in connection with U.S. Appl. No. 11/094,565, filed Mar. 20, 2005.
Examiner Interview Summary Record issued Mar. 19, 2010 in connection with U.S. Appl. No. 11/094,565, filed Mar. 20, 2005.
Final Office Action issued May 25, 2010 in connection with U.S. Appl. No. 09/561,801, filed May 1, 2000.
Final Office Action issued May 26, 2010 in connection with U.S. Appl. No. 11/094,565, filed Mar. 30, 2005.
Official Action issued May 13, 2010 in connection with Japanese Application No. 2006-514923.
Amendment in Response to May 13, 2010 Notice of Rejection in connection with Japanese Application No. 2006-514923.
Official Action issued Apr. 15, 2010 in connection with European application 04809404.9.
Jul. 21, 2010 Amendment in Response to May 25, 2010 Final Office Action submitted in connection with U.S. Appl. No. 09/561,881, filed May 1, 2000.
Response to Examiner's Report filed May 25, 2010 in connection with Canadian Patent Application No, 2,526,810.
Jul. 26, 2010 Amendment in Response to May 26, 2010 Final Office Action submitted in connection with U.S. Appl. No. 11/094,565, filed Mar. 30, 2005.
Aug. 2, 2010 Advisory Action issued in connection with U.S. Appl. No. 09/561,881, filed May 1, 2000.
Official Action issued Jun. 15, 2010 in connection with Israeli Patent Application No. 172093.
Amendment in Response to Aug. 2, 2010 Advisory Action and May 25, 2010 Final Office Action submitted Aug. 9, 2010 in connection with U.S. Appl. No. 09/561,881, filed May 1, 2000.
Supplemental Amendment in Response to May 26, 2010 Final Office Action submitted Aug. 9, 2010 in connection with U.S. Appl. No. 11/094,565, filed Mar. 30, 2005.
Aug. 12, 2010 Advisory Action issued in connection with U.S. Appl. No. 11/094,565, filed Mar. 30, 2005.
Aug. 2, 2010 Amendment submitted in connection with European Patent Application No. 04809404.9.
Office Action issued Sep. 2, 2010 in connection with U.S. Appl. No. 09/561,881, filed May 1, 2000.
Wodicka, L. et al., Nature Biotechn. vol. 15, pp. 1359-1367 (1997).
DeRisi, J. et al., Nature Genetics, vol. 14, pp. 457-460 (1996).
Soares, M.B. et al., PNAS, vol. 91, pp, 9228-9232 (1994).
Office Action issued Sep. 14, 2010 in connection with U.S. Appl. No. 11/094,565, filed Mar. 30, 2005.
Beaucage, S.L., Curr. Med. Chem. vol. 8 pp. 1213-1244 (2001).
Grubor, V. et al. Novel genomic alterations and clonal evolution in chronic lymphocytic leukemia revealed by representational oligonucleotide microarray analysis (ROMA) . Blood 113, 1294-1303 (2009).

* cited by examiner

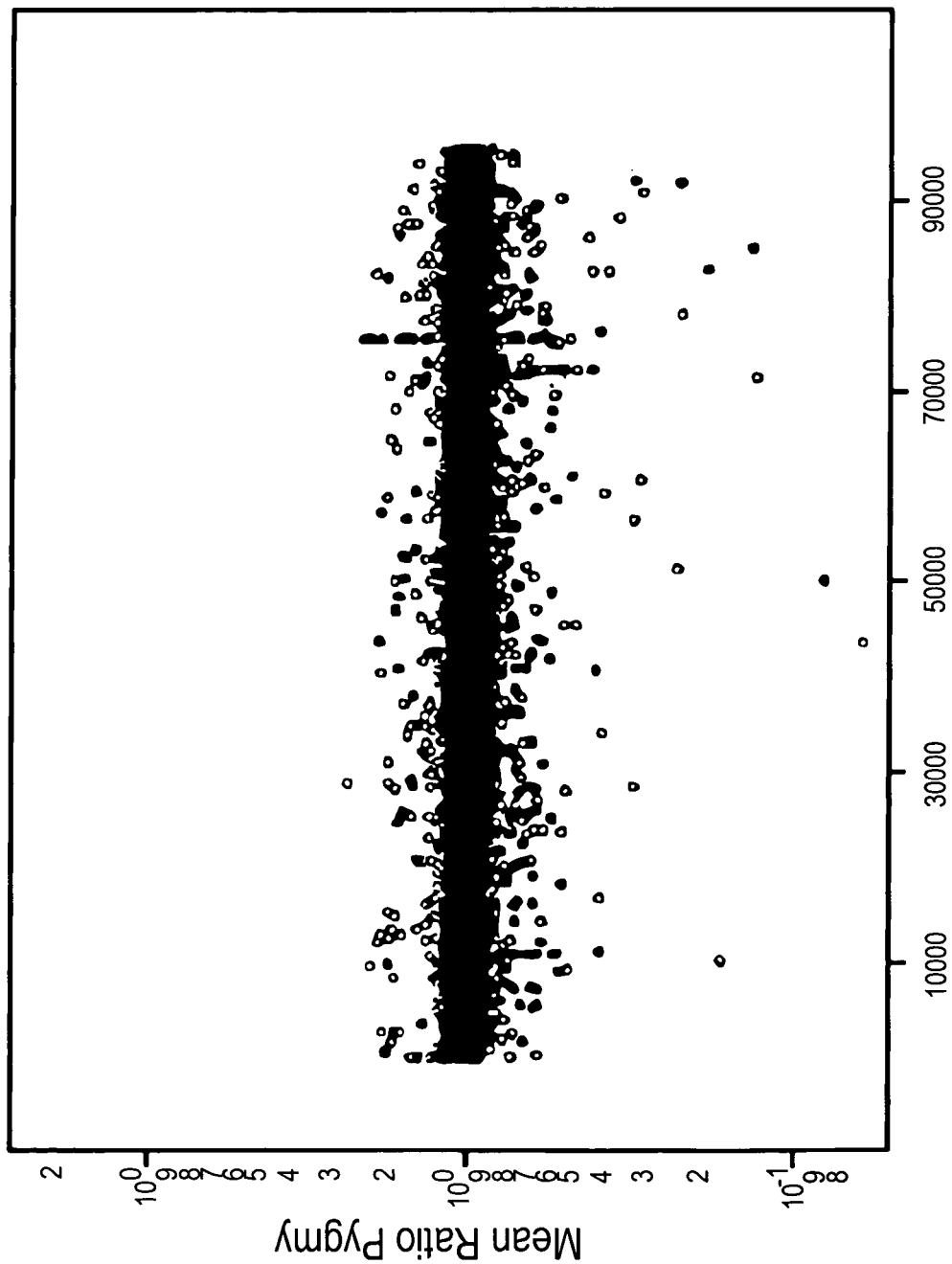

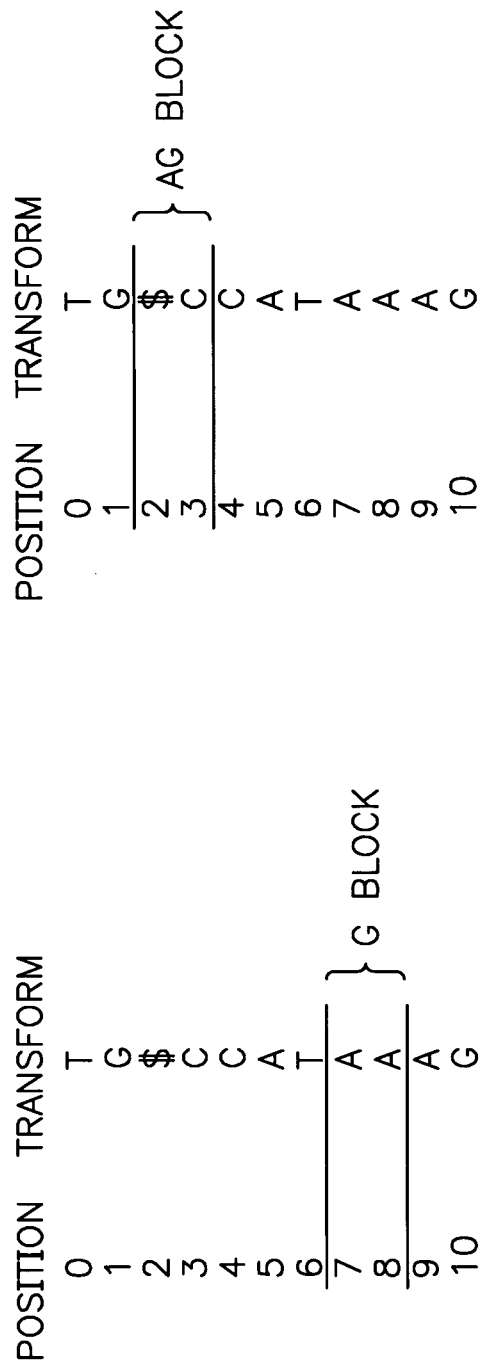

METHOD OF IDENTIFYING VIRTUAL REPRESENTATIONS OF NUCLEOTIDE SEQUENCES

STATEMENT AS TO FEDERALLY SPONSORED RESEARCH

This invention was funded in part by National Institutes of Health Grant Nos. 5R01-CA78544-04; 5R33-CA81674-04; and R21 HG 02606. The Government may have certain rights in this invention.

This application claims benefit of U.S. Patent Application Nos. 60/472,843, filed May 23, 2003 and 60/472,845, filed May 23, 2003, both of which are incorporated by reference herein in their entirety.

FIELD OF THE INVENTION

This invention relates generally to molecular biology. More specifically, this invention relates to materials and methods for generating nucleotide sequences that are representative of a given source DNA (e.g., a genome).

BACKGROUND OF THE INVENTION

Global methods for genomic analysis have provided useful insights into the pathophysiology of cancer and other diseases or conditions with a genetic component. Such methods include karyotyping, determination of ploidy, comparative genomic hybridizaton (CGH), representational difference analysis (RDA) (see, e.g., U.S. Pat. No. 5,436,142), and analysis of genomic representations (WO 99/23256, published May 14, 1999). Generally, these methods involve either using probes to interrogate the expression of particular genes or examining changes in the genome itself.

Using oligonucleotide arrays, these methods can be used to obtain a high resolution global image of genetic changes in cells. However, these methods require knowledge of the sequences of the particular probes. This is particularly limiting for cDNA arrays because such arrays only interrogate a limited set of genes. They also are limiting for genome-wide screening because many oligonucleotides designed for an array may be unrepresented in the interrogated population, resulting in inefficient or ineffective analysis.

SUMMARY OF THE INVENTION

This invention provides compositions and methods useful for interrogating populations of nucleic acid molecules. These compositions and methods can be used to analyze complex genomes (e.g., mammalian genomes), optionally in conjunction with the microarray technology. This invention features a plurality of at least 100 nucleic acid molecules (A) where (a) each of the nucleic acid molecules hybridizes specifically to a sequence in a genome of at least Z basepairs; and (b) at least P % of said plurality of nucleic acid molecules have (i) a length of at least K nucleotides; (ii) hybridizes specifically to at least one nucleic acid molecule present in or predicted to be present in a representation derived from said genome, said representation having no more than R % of the complexity of said genome; and (iii) no more than X exact matches of L1 nucleotides to said genome (or said representation) and no fewer than Y exact matches of L1 nucleotides to said genome (or said representation); and (B) where (a) $Z \geq \times 10^8$; (b) $300 \geq K \geq 30$; (c) $70\% \geq R \geq 0.001\%$; (d) $P\% \geq 90\% - R\%$; (e) $P\% = (((N \times (R\%/100)) + (3 \times sigma))/N) \times 100$; (f) sigma is the square root of $(N \times (R\%/100) \times (1-(R\%/100)))$; (g) the integer closest to $(\log_4(Z)+2)$ L1≥the integer closest to $\log_4(Z)$; (h) X is the integer closest to $D1 \times (K-L_1+1)$; (i) Y is the integer closest to $D2 \times (K-L_1+1)$; (j) $1.5 \geq D1 \geq 1$; and (k) $1 > D2 \geq 0.5$.

In some further embodiments, (1) the plurality of nucleic acid molecules comprises at least 500; 1,000; 2,500; 5,000; 10,000; 25,000; 50,000; 85,000; 190,000; 350,000; or 550,000 nucleic acid molecules; (2) Z is at least $3 \times 10^8$, $1 \times 10^9$, $1 \times 10$ or $1 \times 10^{11}$; (3) R % is 0.001, 1, 2, 4, 10, 15, 20, 30, 40, 50 or 70%; (4) P % is independent of R % and is at least 70, 80, 90, 95, 97 or 99%; (5) D1 is 1; (6) L1 is 15, 16, 17, 18, 19, 20, 21, 22, 23 or 24; (7) P % is 91, 92, 93, 94, 95, 96, 97, 98, 99 or 100%; and/or (8) K is 40, 50, 60, 70, 80, 90, 100, 110, 120, 140, 160, 180, 200 or 250. In some embodiments, a nucleic acid molecule that hybridizes specifically to another nucleic acid molecule has at least 90% sequence identity to a sequence of the same length in the other nucleic acid molecule. In further embodiments, it has at least 91%, at least 92%, at least 93%, at least 94%, at least 95%, at least 96%, at least 97%, at least 98%, at least 99%, or 100% sequence identity.

In some further embodiments, each of said P % of said plurality of nucleic acid molecules further have no more than A exact matches of L2 nucleotides to said genome and no fewer than B exact matches of L2 nucleotides to said genome, wherein (a) $L_1 > L_2 \geq$ the integer closest to $\log_4(Z)-3$, (b) A is the integer closest to $D_3 \times ((K-L_2+1) \times (Z/4^{L_2}))$; (c) B is the integer closest to $D_4 \times ((K-L_2+1) \times (Z/4^{L_2}))$; (d) $4 \geq D_3 \geq 1$; and (e) $1 > D_4 \geq 0.5$.

A representation of a DNA population can be produced by sequence-specific cleavage of said genome, e.g., accomplished with a restriction endonuclease. It can also be derived from another representation. That is, the resultant representation is a compound representation.

The nucleic acid molecules of this invention can be identified by a method comprising: (a) cleaving said genome in silico with a restriction enzyme to generate a plurality of predicted nucleic acid molecules; (b) generating a virtual representation of said genome by identifying predicted nucleic acid molecules each having a length of 200-1,200 basepairs, inclusive, said virtual representation having a complexity of 0.001%-70%, inclusive, of said genome; (c) selecting an oligonucleotide having a length of 30-300 nucleotides, inclusive, and at least 90% sequence identity to a predicted nucleic acid molecule in (b); (d) calculating the complexity of said virtual representation relative to said genome; (e) identifying all of the stretches of L1 nucleotides occurring in said oligonucleotide; and (f) confirming that the number of times each of said stretches occurs in said genome satisfies the various predetermined requirements.

The nucleic acid molecules of this invention can be used as probes for analyzing sample DNA. These probes can be immobilized on the surface of a solid phase, including a semi-solid surface. Solid phases include, without limitation, nylon membranes, nitrocellulose membranes, glass slides, and microspheres (e.g., paramagnetic microbeads). In some embodiments, the positions of the nucleic acid molecules on said solid phase are known, e.g., as used in a microarray format. The invention also features a method of analyzing a nucleic acid sample (e.g., a genomic representation), said method comprising (a) hybridizing the sample to the nucleic acid probes of this invention; and (b) determining to which of said plurality of nucleic acid molecules said sample hybridizes.

This invention features also a method of analyzing copy number variation of a genomic sequence between two genomes, said method comprising: (a) providing two detectably labeled representations, each prepared from the respective genomes with at least one identical restriction enzyme; (b) contacting these two representations with the nucleic acid probes of this invention to allow hybridization between the representations and the probes; (c) analyzing the hybridization levels of the two representations to the probe set, wherein a difference in said levels to a member of the probe set indicates a copy number variation between the two genomes with regard to a genomic sequence targeted by said member. In some embodiments, the representations are distinguishably labeled; and/or the contacting of the two representations is simultaneous.

This invention further features a method of comparing methylation status of a genomic sequence between two genomes, said method involves providing two detectably labeled representations from the respective genomes, each representation being prepared by a methylation sensitive method. For instance, a first representation of a first genome is prepared using a first restriction enzyme and a second representation of a second genome is prepared using a second restriction enzyme, wherein said first and second restriction enzymes recognize the same restriction site but one is methylation-sensitive and the other is not. Sequences with methyl-C can also be chemically cleaved after making a representation with a non-methylation sensitive restriction enzyme, such that a representation derived from a methylated genome is distinguishable from a representation derived from a non-methylated genome. Then the two representations are contacted with the probes of this invention to allow hybridization between the representations and the probes. Hybridization of the two representations to the probes is then analyzed, where a difference in hybridization levels between the representations with regard to a particular probe indicates a difference in methylation status between the two genomes with regard to a genomic sequence targeted by said probe.

Similar methods can also be used to analyze polymorphism of a complex genome, as further illustrated below.

In accordance with certain embodiments of the invention, an algorithm is provided for accurately and efficiently detecting and counting the number of times a word occurs in a genome. This algorithm, sometimes referred to herein as a search engine or a mer-engine, uses a transform of a genome (e.g., a Burrows-Wheeler Transform) and an auxiliary data structure to count the number of times a particular word occurs in the genome. A "word" refers to a nucleotide sequence of a defined length.

In general, the engine searches for a particular word by first finding the last character of the word. Then it proceeds to look for the character immediately preceding the last character. If the first immediately preceding character is found, it then looks for the second immediately preceding character to the last character of the word, and so on until the word is found. If further preceding characters are not found, it will be concluded that the word does not exist in the genome. If the first character of the word is found, then the number of times it occurs is the word count of that particular word.

This particular algorithm is advantageous because it can be used to implement several practical applications involving genomic studies, as discussed below.

Certain embodiments of the algorithm include the features set forth below in numerical sequence.

In some embodiments, the invention provides a method for annotating a nucleotide sequence, said nucleotide sequence comprising a string of characters, said method comprising: partitioning said nucleotide sequence into a plurality of words of a predetermined length, each word being a subregion of said nucleotide sequence having said predetermined length; and determining a word count for each word by counting the number of times each word appears in said nucleotide sequence. In some embodiments, said words overlap.

In some embodiments, said determining in the method for annotating a nucleotide sequence comprises using a word counting algorithm that utilizes a compressed transform of said nucleotide sequence to count how many times each word occurs in said nucleotide sequence. In some embodiments, the word counting algorithm comprises: iterating through each character of one of said words, starting with the last character and advancing to the first character one character per iteration, wherein the character corresponding to a particular iteration is stored as an index character, said iterating further comprising: defining a search region that delineates a contiguous range of characters within said transform; counting the number of times the character preceding said index character occurs in said search range; and wherein said iterating ceases if no occurrences of the character preceding said index character occurs in said search range; and outputting the number of times the first character is counted, this number being equivalent to the number times that particular word appears in said nucleotide sequence.

In some embodiments, the method for annotating a nucleotide sequence comprises performing a statistical analysis on the word counts obtained for each word.

In some embodiments, the method for annotating a nucleotide sequence comprises partitioning said nucleotide sequence into a second plurality of words of a second predetermined length, each of said second plurality of words being a subregion of said nucleotide sequence having said second predetermined length; and determining a word count for each of said second plurality of words by counting the number of times each of said second plurality of words appears in said nucleotide sequence.

In some embodiments, the annotated nucleotide sequence is a genome.

In some embodiments, the invention provides a system for annotating a nucleotide sequence, said nucleotide sequence comprising a string of characters, said system comprising user equipment configured to: partition said nucleotide sequence into a plurality of words of a predetermined length, each word being a subregion of said nucleotide sequence having said predetermined length; and determine a word count for each word by counting the number of times each word appears in said nucleotide sequence. In some embodiments, the words overlap.

In some embodiments, the user equipment is configured to use a word counting algorithm that utilizes a compressed transform of said nucleotide sequence to count how many times each word occurs in said nucleotide sequence. In some embodiments, the user equipment is further configured to: iterate through each character of one of said words, starting with the last character and advancing to the first character one character per iteration, wherein the character corresponding to a particular iteration is stored as an index character, said user equipment further configured to iterate by repeating the steps that: define a search region that delineates a contiguous range of characters within said transform; count the number of times the character preceding said index character occurs in said search range; and ceases iteration if no occurrences of the character preceding said index character occurs in said search range; and output the number of times the first character is counted, this number being equivalent to the number times that particular word appears in said nucleotide sequence.

In some embodiments, the user equipment is configured to perform a statistical analysis on the word counts obtained for each word. In some embodiments, the user equipment is configured to: partition said nucleotide sequence into a second plurality of words of a second predetermined length, each of said second plurality of words being a subregion of said nucleotide sequence having said second predetermined length; and determine a word count for each of said second plurality of words by counting the number of times each of said second plurality of words appears in said nucleotide sequence.

In some embodiments, the invention provides a method for selecting a polynucleotide that has minimal potential for cross-hybridizing to undesired regions of a nucleotide sequence, said method comprising: selecting a plurality of polynucleotides of a predetermined length that exist within said nucleotide sequence; generating statistical data on each polynucleotide; and determining which one of said polynucleotides has statistical data that best satisfies predetermined criteria.

In some embodiments, the generating in the method for selecting a polynucleotide that has minimal potential for cross-hybridizing comprises: partitioning each polynucleotide into a plurality of words of a predetermined length, each word being a subregion of the polynucleotide having said predetermined length; and determining a word count for each word by counting the number of times each word appears in said nucleotide sequence.

In some embodiments, the statistical data represents the number of times constituent words of each polynucleotide appear in said nucleotide sequence.

In some embodiments, the predetermined criteria in the method for selecting a polynucleotide that has minimal potential for cross-hybridizing comprise a minimum mean value of word counts of a predetermined length, a geometric mean value of word counts of a predetermined length, a mode value of word counts of a predetermined length, a minimized maximum value of word counts of a predetermined length, a sum total value of word counts of a predetermined length, a product value of word counts of a predetermined length, a maximum length string of a particular nucleotide, or a combination thereof.

In some embodiments, the selecting in the method for selecting a polynucleotide that has minimal potential for cross-hybridizing comprises generating word counts of a particular word having a particular length that occurs in said nucleotide sequence; and obtaining polynucleotides from regions of said nucleotide sequence such that the word counts for the substrings within said regions do not exceed a predetermined word count.

In some embodiments, the invention provides a system for selecting a polynucleotide that has minimal potential for cross-hybridizing to undesired regions of a nucleotide sequence, said method comprising user equipment configured to: select a plurality of polynucleotides of a predetermined length that exist within said nucleotide sequence; generate statistical data on each polynucleotide; and determine which one of said polynucleotides has statistical data that best satisfies predetermined criteria.

In some embodiments, the user equipment in the system for selecting a polynucleotide that has minimal potential for cross-hybridizing is configured to: partition each polynucleotide into a plurality of words of a predetermined length, each word being a subregion of the polynucleotide having said predetermined length; and determine a word count for each word by counting the number of times each word appears in said nucleotide sequence.

In some embodiments, the statistical data in the system for selecting a polynucleotide that has minimal potential for cross-hybridizing represents the number of times constituent words of each polynucleotide appear in said nucleotide sequence.

In some embodiments, the predetermined criteria in the system for selecting a polynucleotide that has minimal potential for cross-hybridizing comprise a minimum mean value of word counts of a predetermined length, a geometric mean value of word counts of a predetermined length, a mode value of word counts of a predetermined length, a minimized maximum value of word counts of a predetermined length, a sum total value of word counts of a predetermined length, a product value of word counts of a predetermined length, a maximum length string of a particular nucleotide, or a combination thereof.

In some embodiments, the user equipment in the system for selecting a polynucleotide that has minimal potential for cross-hybridizing is configured to: generate word counts of a particular word having a particular length that occurs in said nucleotide sequence; and obtain polynucleotides from regions of said nucleotide sequence such that the word counts for the substrings within said regions do not exceed a predetermined word count.

In some embodiments, the invention provides a method for counting the number of times a word occurs in a genome, wherein said word comprises a string of characters, said method comprising: providing a compressed transform of said genome; iterating through each character of said word, starting with the last character and advancing to the first character one character per iteration, wherein the character corresponding to a particular iteration is stored as an index character, said iterating further comprising: defining a search region that delineates a contiguous range of characters within said transform; counting the number of times the character preceding said index character occurs in said search range; and wherein said iterating ceases if no occurrences of the character preceding said index character occurs in said search range; and outputting the number of times the first character of said word is counted, this number being equivalent to the number times said word appears in said genome.

In some embodiments, the method for counting the number of times a word occurs in a genome further comprises: providing an auxiliary data structure, said auxiliary data structure comprising: a K-intervals data structure that maintains a running total of each character that has appeared in said transform up to and including a particular predetermined location in said compressed transform; and a dictionary-counts data structure that provides fast look-up access to the compressed transform; and wherein said counting is performed using at least said K-interval data structure and said dictionary-counts data structure.

In some embodiments, the transform remains compressed while said counting is being performed. In some embodiments, the compressed transform is compressed such that every three characters in the uncompressed transform are compressed to form a byte, and wherein said counting uncompresses at most one such byte during one of said iterations. In some embodiments, the compressed transform of said genome is derived using a compression ratio of 3-to-1. In some embodiments, the compressed transform is a Burrows-Wheeler transform of the genome.

In some embodiments, the genome comprises at least a million characters, e.g., at least four million characters, at least a hundred million characters, or at least three billion characters.

In some embodiments, the word comprises at least 15 characters.

In some embodiments, the method for counting the number of times a word occurs in a genome further comprises providing data which is based on said transform, wherein said defining comprises using said data and said index character to define said search region.

In some embodiments, the method for counting the number of times a word occurs in a genome further comprises: providing data which is based on said transform; and determining a prior character count, said prior character count being the number of times the character preceding the index character occurs in said transform before the beginning of said search region; wherein said defining comprises using said data, said index character, and said prior character count to define said search region. In some embodiments, said prior character count is obtained using K-intervals, said K-intervals being stored at predetermined locations along said transform and maintain a running total of each character that has appeared in said transform up to and including a particular predetermined location.

In some embodiments, the invention provides a system comprising user equipment that is configured to perform a method for counting the number of times a word occurs in a genome, wherein said word comprises a string of characters.

Other features and advantages of the invention will be apparent from the following drawings, detailed description and claims.

BRIEF DESCRIPTION OF THE DRAWINGS

FIG. 1A shows the results where the samples hybridized are a BglII representation and a BglII representation depleted of fragments with a HindIII cleavage site. The Y-axis (Mean Ratio) is the mean measured ratio from two hybridizations of depleted representation to normal representation plotted in log scale. The X-axis (Index) is a false index constructed such that probes deriving from fragments defined as having an internal HindIII site are to the right side. FIG. 1B shows the reproducibility of the duplicate experiments used to generate the average ratio in FIG. 1A. The Y-axis (Ratio Exp1) is the measured ratio from experiment 1 and the X-axis (Ratio Exp2) is the measured ratio of experiment 2. Both axes are plotted in log scale. FIG. 1C graphs the normalized ratio on the Y-axis as a function of intensity of the sample that was not depleted on the X-axis. Both the ratio and intensity were plotted in log scale. FIG. 1D represents data generated by simulation. The X-axis (Index) is a false index. Probes, in groups of 600, detect increasing copy number, from left to right. 600 flanking probes detect normal copy number. The Y-axis (Mean Ratio) is mean ratio plotted on a log scale.

FIGS. 2A1-2A3, 2B1-2B3, and 2C1-2C3 show the genomic profiles for a primary breast cancer sample (CHTN159), with aneuploid nuclei compared to diploid nuclei from the same patient (FIG. 2A1-2A3), a breast cancer cell line compared to a normal male reference (FIG. 2B1-2B3), and a normal male to a normal male reference (FIG. 2C1-2C3), using the 10K printed array (FIG. 2A1, FIG. 2B1, FIG. 2C1) and the 85K photoprint array (FIG. 2A2, FIG. 2B2, FIG. 2C2). In each case (FIG. 2A1, FIG. 2B1, FIG. 2C1 and FIG. 2A2, FIG. 2B2, FIG. 2C2) the Y-axis is the mean ratio, and the X-axis (Gen Index) is an index, which plots the probes in genomic order, concatenating the chromosomes, and allowing the visualization of the entire genome from chromosome 1 to Y. FIG. 2A3, FIG. 2B3, and FIG. 2C3 show the correspondence of the ratios measured from "brother" probes present in the 10K and the 85K microarrays. The Y-axis is the measured ratio from the 10K microarray and the X-axis is the measured ratio from the 85K micro array.

FIG. 3A represents copy number fluctuations identified for chromosome 5, FIG. 3B for chromosome 8, FIG. 3C for chromosome 17 and FIG. 3D for the X chromosome.

In FIGS. 4A-4D, the Y-axis is the value of the mean segment for each probe in log scale. In FIG. 4A and FIG. 4C, the X-axis (Mean Segment Index) is each listed in ascending value of their assigned mean segment. In FIG. 4B and FIG. 4D the X-axis (Gen Index) is a genomic index, which, as described above, places the entire genome end to end. Plotted on top of the mean segment data is a copy number lattice extrapolated from the array data using formulas within the text (horizontal lines). Calculated copy number for each horizontal line is to the right of the lattice.

FIG. 5A shows a region from X chromosome with a region of loss. Plotted over the measured array ratio is the calculated segmentation value. FIG. 5B shows a region of chromosome 8 (c-myc located to the right of the center of the graph) from results of SK-BR-3 in comparison to normal reference. Plotted on top of the data are the segmentation values for SK-BR-3 in comparison to normal reference in diagonal hatch and the segmentation values for the primary tumor CHTN159 in vertical hatch. FIG. 5C shows a lesion on chromosome 5 demonstrating the resolving power of the 85K as compared to the 10K array. Results are from SK-BR-3 compared to a normal reference. Open circles are from the 10K printed microarray and filled circles are from the 85K photoprint array. Horizontal lines are copy number estimates, based on modeling from mean segment values. FIG. 5D shows comparison of SK-BR-3 to normal reference, displaying a region of homozygous deletion on chromosome 19. The mean segment value is plotted as a white line, and the lattice are copy number estimates as described above.

FIGS. 6A-6D show the results of a normal compared to a normal, identical to that displayed in FIG. 2C2 with the exception that singlet probes have been filtered as described in the text. FIG. 6B illustrates the serial comparison of experiments for a small region from chromosome 4. The Y-axis is the mean ratio in log scale. The X-axis is a genomic index. The filled (85K) and open (10K) circles are from the comparison of SK-BR-3 to normal. The empty triangles are a comparison of a pygmy to the normal reference. FIG. 6C illustrates a lesion found in the normal population on chromosome 6. The filled circles are plotted by mean ratio for analysis of the pygmy to the normal reference. The vertical hatch line is the mean segment value for the pygmy to normal reference comparison. The diagonal hatch line is the mean segment value for the SK-3-BR-3 to normal reference comparison. The cross hatch line is the segment value from the primary tumor (CHTN159 aneuploid to diploid) comparison. FIG. 6D shows a region of chromosome 2. The data shown in circles is from the comparison of SK-BR-3 to normal reference. The mean segment line for this comparison is shown in vertical hatch. The mean segment line for the comparison of a pygmy to the normal reference is shown in diagonal hatch and for the primary tumor CHTN159 in cross hatch. For FIG. 6C and FIG. 6D the calculated copy number for the horizontal lines is found to the right of the panel.

FIGS. 10A and 10B show an illustrative example of word counting algorithm of FIGS. 9A and 9B in accordance with certain embodiments of the invention.

DETAILED DESCRIPTION OF THE INVENTION

Figure 1A:
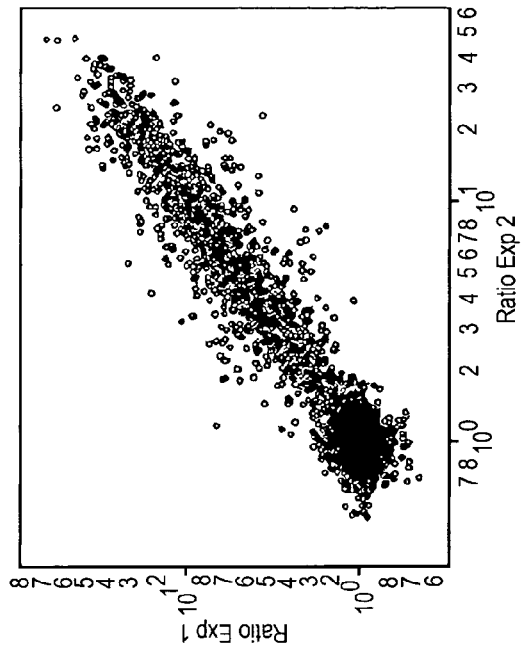
FIGS. 1A-1D demonstrate the predictability of informatics and accuracy of the array measurements using microarrays comprising 10,000 oligonucleotides.
Figure 1B:
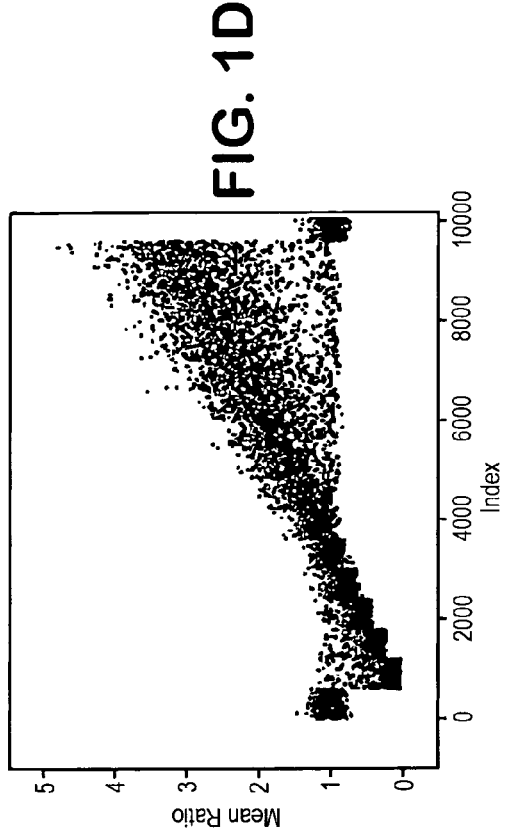
Figure 1C:
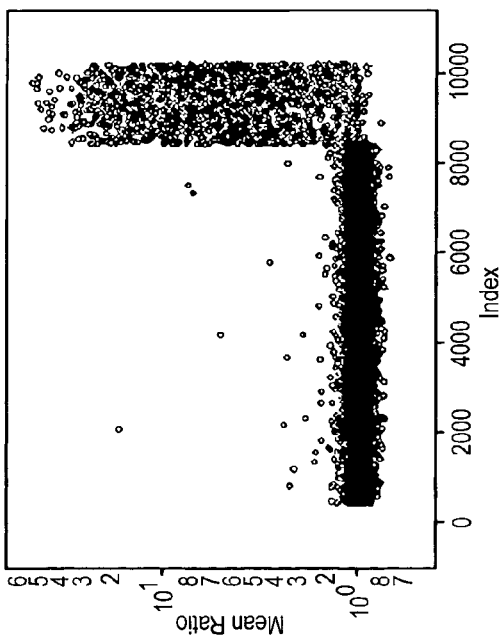
Figure 1D:
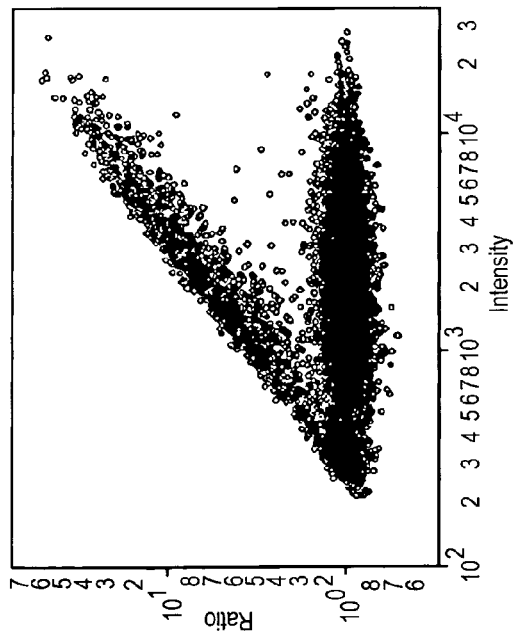

This invention features oligonucleotide probes for analyzing representations of a DNA population (e.g., a genome, a chromosome or a mixture of DNAs). The oligonucleotide probes may be used in solution or they may be immobilized on a solid (including semi-solid) surface such as an array or a microbead (e.g., Lechner et al., Curr. Opin. Chem. Biol. 6:31-38 (2001); Kwok, Annu. Rev. Genomics Human Genet. 2:235-58 (2601); Aebersold et al., Nature 422:198-207 (2003); and U.S. Pat. Nos. 6,355,431 and 6,429,027). A representation is a reproducible sampling of a DNA population in which the resulting DNA typically has a new format or reduced complexity or both (Lisitsyn et al., Science 258:946-51 (1993); Lucito et al., Proc. Natl. Acad. Sci. USA 92:151-5 (1998)). For example, a representation of a genome may consist of DNA sequences that are from only a small portion of the genome and are largely free of repetitive sequences. Analysis of genomic representations may reveal changes in a genome, including mutations such as deletions, amplifications, chromosomal rearrangements, and polymorphisms. When done in a clinical setting, the analysis can provide insight into the molecular basis of a disease as well as useful guides to its diagnosis and treatment.

The oligonucleotide compositions of this invention can be used to hybridize to representations of a source DNA, where hybridization data are processed to provide genetic profiles of the source DNA (e.g., disease-related genetic lesions and polymorphisms). It may be preferred that the representations (or "test representations" hereinafter) and at least a fraction of the oligonucleotide probes in the compositions are derived from the same species. DNA from any species may be utilized, including mammalian species (e.g., pig, mouse, rat, primate (e.g., human), dog, and cat), species of fish, species of reptiles, species of plants and species of microorganisms.

I. OLIGONUCLEOTIDE PROBES

The oligonucleotide probes of this invention are preferably designed by virtual representation of a source DNA, such as the genomic DNA of a reference individual. Representation of the genome generally, but not invariably, results in a simplification of its complexity. The complexity of a representation corresponds to the fraction of the genome that is represented therein. One way to calculate complexity is to divide the number of nucleotides in the representation by the number of nucleotides in the genome. The genomic complexity of a representation can range from below 1% to as high as 95% of the total genome. Where DNA from an organism with a relatively simple genome is used, the representation may have a complexity of 100% of the total genome, e.g., the representation may be generated by restriction digest of total DNA without amplification. Representations associated with the invention typically have a complexity of between 0.001% and 70%. Reduction of complexity allows for desirable hybridization kinetics.

An "actual" representation of DNA involves laboratory procedures ("wet work") by which representational DNAs are selected. Virtual representations, on the other hand, take advantage of the fact that complete genomes, for example, the human genome, have been sequenced. Through computational analysis of the available genomic sequences, one can readily design a large number of oligonucleotide probes that hybridize to mapped regions of the genome and have a minimal degree of sequence overlap to the rest of the genome.

By way of example, to design a set of oligonucleotide probes for human genetic analysis, one can perform an in silico (i.e., virtual) digestion of the human genome by locating all cleavage sites of a selected restriction endonuclease in the sequenced genome. One can then analyze the resulting fragments to identify those that are in a desired range (e.g., 200-1,200 bps, 100-400 bps and 400-600 bps) that can be amplified by, e.g., PCR. Such fragments are defined herein as "predicted to be present" in a representation. A restriction endonuclease may be selected based on the complexity of the representation desired. For example, restriction endonucleases that cut infrequently, such as those that recognize 6 bp or 8 bp target sequences, will produce representations of lower complexity, whereas restriction endonucleases that cut frequently, such as those that recognize 4 bp target sequences, will produce representations of higher complexity. In addition, factors such as the G/C content of the genome analyzed will affect the frequency of cleavage of particular restriction endonucleases and consequently influence the selection of the restriction endonucleases. Generally, robust restriction endonucleases that do not exhibit star activity are used. Alternatively, cleavage based on methylation state of a target site may also be employed, e.g. through the use of a methylation-sensitive restriction enzyme or other enzyme such as McrBC, which recognizes methylated cytosines in DNA.

Sequences of all digested fragments of a desired range (e.g., 200-1,200 bps, 100-400 bps and 400-600 bps) are analyzed by computer, where regions of some of these fragments that are at least about 30 bps in length and have minimal homology to the rest of the genome can be selected as representational oligonucleotide probes for the human genome. Examples 1 and Section VI below further illustrate methods of identifying the oligonucleotides of this invention.

Oligonucleotides of the invention may range in length from about 30 nucleotides to about 1,200 nucleotides. The exact length of oligonucleotides chosen will depend on the intended use, e.g., the size of the source DNA from which the representation is prepared and whether they are used as components of an array. The oligonucleotides typically have a length of at least 35 nucleotides, e.g., at least 40, 45, 50, 55, 60, 65, 70, 75, 80, 85, 90, 95 or 100 nucleotides, but they may also be shorter having a length of, e.g., 20, 21, 22, 23, 24, 25, 26, 27, 28, 29 or 30 nucleotides. The oligonucleotides typically have a length of no more than 600 nucleotides, e.g., no more than 550, 500, 450, 400, 350, 300, 250, 200 or 150 nucleotides. As would be recognized by one of skill in the art, the length of the oligonucleotides will depend on features of the genome analyzed, e.g., complexity and amount of repetitive sequences.

II. OLIGONUCLEOTIDE ARRAYS

The oligonucleotide probes of this invention can be used in an array format. An array comprises a solid support with nucleic acid probes attached thereto at defined coordinates, or addresses. Each address contains either many copies of a single DNA probe, or a mixture of different DNA probes. Nucleic acid arrays, also termed "microarrays" or "chips," have been generally described in the art. See, e.g., U.S. Pat. No. 6,361,947 and references cited therein. We have termed genetic analysis using the new arrays "representational oligonucleotide microarray analysis" ("ROMA") or, where cleavage depends on methylation at the target site, "methylation detection oligonucleotide microarray analysis" ("MOMA").

To manufacture a microarray of this invention, pre-synthesized oligonucleotides are attached to a solid support, which may be made from glass, plastic (e.g., polypropylene or nylon), polyacrylamide, nitrocellulose, or other materials, and may be porous or nonporous. One method for attaching the nucleic acids to a surface is by printing on glass plates, as is described generally by Schena et al., Science 270:467-70 (1995); DeRisi et al., Nature Gen. 14:457-60 (1996); Shalon et al., Genome Res. 6:639-45 (1996); and Schena et al., Proc. Natl. Acad. Sci. USA 93:10539-1286 (1995). For low density arrays, one can also use dot blots on a nylon hybridization membrane. See, e.g., Sambrook et al., Molecular Cloning—A Laboratory Manual (2nd Ed.), Vol. 1-3, Cold Spring Harbor Laboratory, Cold Spring Harbor, N.Y., 1989.

Another method for making microarrays is by using photolithographic (or "photoprint") techniques to synthesize oligonucleotides directly on the array substrate, i.e., in situ. See, e.g., Fodor et al., Science 251:767-73 (1991); Pease et al., Proc. Natl. Acad. Sci. USA 91:5022-6 (1994); Lipschutz et al., Nat. Genet. 21 (1 Suppl):20-46 (1999); Nuwaysir et al., Genome Res. 12(11):1749-55 (2002); Albert et al., Nucl. Acids Res. 31(7):e35 (2003); and U.S. Pat. Nos. 5,578,832, 5,556,752, and 5,510,270. Other methods for rapid synthesis and deposition of defined oligonucleotides can also be used. See, e.g., Blanchard et al., Biosensors & Bioelectronics 11:687-90 (1996); and Maskos and Southern, Nucl. Acids Res. 20:1679-1684 (1992).

The arrays of the invention typically comprise at least 100 (e.g., at least 500, 1,000, 5,000 or 10,000) oligonucleotide probes, and may comprise many more probes, for example, up to 25,000, 50,000, 75,000, 85,000, 100,000, 200,000, 250, 000, 500,000 or 700,000 probes. The arrays of the invention typically do not comprise more than 700,000 probes. However, they may comprise more, e.g., up to 800,000, 900,000 or 1,000,000 probes. In some embodiments, the arrays are high density arrays with densities greater than about 60 different probes per 1 cm$^2$. The oligonucleotides in the arrays may be single-stranded or double-stranded. To facilitate manufacturing and use of the arrays, the oligonucleotide probes of this invention may be modified by, e.g., incorporating peptidyl structures and analog nucleotides, into the probes.

III. TEST REPRESENTATIONS

The oligonucleotide arrays of this invention can be used to probe any nucleic acid sample of choice. For example, the sample may be a cDNA library, a genomic DNA library, or an RNA preparation. In other embodiments, the arrays of this invention are used to probe DNA samples that are representations (or "test representations") of a complex DNA population, such as the genome of a higher organism.

Representations and methods for their preparation are described in, e.g., Lisitsyn et al., Proc. Natl. Acad. Sci. USA 92:151 (1995); Lucito et al., Proc. Natl. Acad. Sci. USA 95:4487-4492 (1998); and WO 99/23256. One approach for making a representation involves reproducibly cleaving a DNA population into fragments. Reproducible cleavage is generally accomplished by digesting with one or more restriction endonucleases (e.g. DpnI or BglII) or enzyme(s) that cleave at particular methylated sites (e.g. McrBC), but any method that reproducibly cleaves the DNA may be used. The resulting DNA fragments are linked to adaptor oligonucleotides. These fragments are then amplified by, e.g., polymerase chain reaction ("PCR") or ligase chain reaction, using primers complementary to the adaptors. The amplified fragments represent a subset of the starter DNA population. Due to the amplification step, representations can be made from very small amounts of starting material (e.g., from 5 ng of DNA). Representational difference analysis ("RDA") as described in Lisitsyn et al., Science 258:946-51 (1993) and U.S. Pat. Nos. 5,436,142 and 5,501,964 may be used to remove any known, unwanted sequences from the representation, including repetitive sequences.

The starter DNA population can be large DNA molecules such as the genome of an organism, or a part thereof (e.g., a chromosome or region thereof). We refer to representations of such a DNA population as chromosomal or genomic representations, respectively. The starter DNA populations can be obtained from, e.g., diseased tissue samples such as tumor biopsy samples, normal tissue samples, tumor cell lines, normal cell lines, cells stored as fixed specimens, autopsy samples, forensic samples, paleo-DNA samples, microdissected tissue samples, isolated nuclei, isolated chromosomes or regions of chromosomes, and fractionated cell or tissue samples. One can also make a representation of a representation (or a "compound representation"). Compound representations are useful for screening for polymorphisms. See, e.g., WO 99/23256.

For comparative analysis of representations from two DNA sources, such as comparing a genomic representation from a normal cell with a genomic representation from a cancerous or otherwise diseased cell, it may be preferred to prepare the two representations in parallel, e.g., isolating the starter DNA from the two cells at the same time and in the same manner, preparing the representations from the same amount of starter DNA, and amplifying DNA fragments at the same time under the same conditions in the same thermal cycler. It may also be preferred that the normal cell and the diseased cell are taken from the same individual, although it is possible to obtain "normal" genomic DNA by combining, e.g., the DNA from both parents of the individual.

The complexity of a representation is generally lower than that of the starter DNA population, because there are sequences present in the starter population that are not present in the representation. The complexity of a representation is related to the cutting frequency of the restriction endonuclease in a particular starter population. A more frequent cutter gives rise to a more complex representation. Because fragments between 200-1,200 basepairs are preferentially amplified by PCR under typical conditions, one can obtain high complexity representations by cleaving the starter DNA such that a majority of the fragments are between 200-1,200 basepairs. Conversely, low complexity representations can be obtained by cleaving the DNA molecule such that fewer of the fragments are between 200-1,200 basepairs. For example, DpnII digestion of human genomic DNA may give rise to a representation having about 70% of the complexity of the entire human genome. Digestion by a less frequent cutter such as BamHI or BglII, on the other hand, may give rise to a representation having only about 2% of the complexity of the human genome. High complexity representations are useful for, e.g., determining gene copy number, deletion mapping, determining loss of heterozygosity, comparative genomic hybridization, and archiving of DNA. Generally, low complexity representations are useful for the same purposes, but give better hybridization kinetics than high complexity representations.

The complexity of a representation may be further finetuned by using more than one restriction enzyme to generate fragments prior to ligation of the adaptors, and/or by using one or more additional restriction enzymes to cleave a subset of the fragments after ligation of the adaptors, thus depleting the resulting representation of those fragments. Any restriction enzyme, including methylation sensitive restriction enzymes, may be used to produce a representation for analysis as described herein.

The complexity of the representation also can be shaped by the choice of adaptors used for amplification. For example, which adaptors are used can influence the sizes of members of a representation. Where identical adaptors are ligated to both ends of the cleaved fragments, panhandle formation between adaptors within the single strands competes with primer annealing, thus inhibiting amplification by PCR. See Lukyanov et al., Anal. Biochem. 229:198-202 (1995). Amplification of shorter fragments is more likely to be inhibited because the adaptors are closer to each other in shorter fragments, resulting in a higher effective local concentration of the ligated adaptors and, thus, greater interaction. Adaptors that form panhandles of approximately 29 basepairs allow for amplification of fragments in the size range of 200-1,200 basepairs. Adaptors that form shorter panhandles, e.g., 24 basepairs, release some of the inhibition of the smaller fragments, resulting in the favoring of smaller PCR amplification products and therefore, a representation of altered complexity.

IV. HYBRIDIZATION OF NUCLEIC ACID SAMPLES TO ARRAYS

The microarrays of this invention are typically hybridized to samples of single-stranded nucleic acids in solution. Because the potential hybridization signal may vary from address to address in the hybridization chamber, the probe array may preferably be used as a comparator, measuring the ratio of hybridization between two differently labeled specimens (the sample) that are thoroughly mixed and therefore share the same hybridization conditions. Typically the two specimens will be from test (e.g., diseased) and control (e.g., disease-free) cells, respectively.

Samples to be hybridized to the microarrays, e.g., the above-described test representations, can be detectably labeled by any means known to one of skill in the art. In some embodiments, the sample is labeled with a fluorescent moiety by, for example, random primer labeling or nick translation. When the sample is a representation, it may be labeled during the amplification step by inclusion of labeled nucleotides in the reaction. The fluorescent label may be, for example, a lissamine-conjugated nucleotide or a fluorescein-conjugated nucleotide analog. In some embodiments, two differentially labeled samples (e.g., one labeled with lissamine and the other with fluorescein) are used. In some embodiments, the samples are unlabeled.

Hybridization and wash conditions are chosen such that the nucleic acid molecules in the sample specifically bind to complementary oligonucleotides on the array. Arrays containing double-stranded oligonucleotides are generally subjected to denaturing conditions to render the oligonucleotides single-stranded prior to contacting with the sample. Optimal hybridization conditions will depend on the length and type (e.g., RNA or DNA) of the oligonucleotide probe and sample nucleic acids.

Hybridization to an array of the invention may be detected by any method known to those of skill in the art. In some embodiments, the hybridization of flourescently labeled sample nucleotides is detected by laser scanner. In some embodiments, the hybridization of labeled or unlabeled sample nucleotides is detecting by measuring their mass. When two different fluorescent labels are used, the scanner may be one that is able to detect fluorescence of more than one wavelength, the wavelength corresponding to that of each fluorescent label, typically simultaneously or nearly simultaneously.

V. EXEMPLARY USES FOR THE OLIGONUCLEOTIDE PROBES

The oligonucleotide probes of the invention may be used to detect and quantify the changes in the copy number or methylation status of specific sequences in a genome. Where representations derived from a plurality of DNA samples are hybridized to the same oligonucleotide probes, the relative intensity of hybridization between the two samples to a particular probe is indicative of the relative copy number or methylation status of the sequence corresponding to that probe in the two samples. Genomes, for example, typically contain either extra copies of certain sequences due to amplification or fewer or no copies of certain sequences due to deletion of specific regions. These methods can be used, for example, to analyze changes in the copy of number or methylation status of sequences between a reference sample and patient samples where amplification, deletion or methylation status of specific sequences is implicated in, for example, the predisposition, progression or staging of specific diseases including, for example, cancer, neurological diseases (e.g., autism), diabetes, cardiological diseases and inflammatory diseases (e.g., autoimmune diseases).

In addition, positional information on the alteration of copy number or methylation status in a genome can be obtained because the sequences in the genome to which the oligonucleotide probes of the invention are complementary are known. Where the oligonucleotide probes are designed to hybridize frequently in the genome sequence and the sample is a high complexity representation, it is possible to map precisely regions of genome amplification, deletion or methylation status. Thus, the invention may be used to identify individual genes that may be involved in the predisposition, progression or staging of specific diseases. These genes may be oncogenes and tumor suppressor genes depending on whether the sequence is amplified, deleted or methylated/unmethylated in a cancer genome relative to a reference genome, respectively.

The oligonucleotide probes of the invention also may be used to identify polymorphic sites, including single nucleotide polymorphisms (SNPs), both within an individual and between individuals. These polymorphisms are common and as many as 2-3% of oligonucleotide probes display polymorphic behavior even between "normal" individuals. Detectable polymorphisms may result from the loss or gain of restriction endonuclease fragments, e.g., due to point mutations, deletions, genomic rearrangements or gene conversions extending over heterozygous polymorphisms, where they are reflected in their presence or absence in a representation. For example, digestion of the a nucleotide sequence with a restriction enzyme may result in one large (i.e., uncleaved) or two small fragments depending on whether a restriction site is present. This polymorphic restriction site is known to exist in a test genome if the oligonucleotide probes detect one or both of the small fragments in the test representation.

Similarly, genomic rearrangements, including translocations, insertions, inversions and deletions, may result in the creation of new restriction endonuclease fragments spanning at least part of the rearrangement. Some of these new fragments may be amplifiable and, therefore, present in a representation of the rearranged genome but absent from a reference representation. Conversely, genomic rearrangements may result in the loss of a fragment from a representation. In either case, a difference between the test and reference representations in hybridization to certain probes suggests that genomic rearrangements may have occurred in the test genome relative to the reference genome. By analyzing the sequences of these probes and the locations of these probes in the reference genome, one can obtain information on the genetic rearrangements, including the type of rearrangements and the junctions of the rearrangements.

The ability to analyze copy number and other polymorphisms of specific sequences within and between individuals has many uses that will be apparent to one of skill in the art. These may be, but are not limited to, identification of individuals, e.g., for forensic testing and paternity testing; breeding of plants or animals; discovery of polymorphisms that are genetically linked to an inherited trait, including the analysis of quantitative traits; determination of drug response in a patient, including predicting a beneficial or adverse response to a drug; diagnosis; and for patient identification and stratification in clinical trials.

VI. AN EXEMPLARY SEARCH ENGINE

The following describes an algorithm that can be used to obtain the above-mentioned oligonucleotide probes. It will be understood that the following description is not intended to show that this algorithm is the only means to obtain such probes. It will also be understood that this algorithm has applications other than generating the oligonucleotide probes of this invention. Some of the other applications are described herein.

This algorithm, sometimes referred to herein as a search engine or a mer-engine, uses a transform of a genome (e.g., a Burrows-Wheeler Transform) and an auxiliary data structure to count the number of times a particular word occurs in the genome. A "word" refers to a nucleotide sequence of any length.

In general, the engine searches for a particular word by first finding the last character of the word. Then it proceeds to look for the character immediately preceding the last character. If the first immediately preceding character is found, it then looks for the second immediately preceding character to the last character of the word, and so on until the word is found. If further preceding characters are not found, it will be concluded that the word does not exist in the genome.

This particular algorithm is advantageous because it can be used to implement several practical applications involving genomic studies, as discussed above. One application of the search engine is that it can be used to annotate a nucleotide sequence such as a genome. Particularly, the genome can be annotated using substrings of a particular length that exist within the genome. The search engine can then count the number of times a particular length substring occurs in the genome. These counts provide an indication of the uniqueness of a particular substring, where lower counts represent a higher degree of uniqueness than higher counts.

Probe design is another practical application that is advantageously enhanced by using the search engine. The engine's ability to rapidly count the number of times a particular word appears in a genome is particularly useful in designing probes that are unique and hybridize to a specific region of DNA, with minimal cross-hybridization. By using the search engine, potential cross-hybridizations can be minimized by requiring a probe to be comprised of constituent segments that are unique and meet certain stringency conditions such as having low word counts or no word counts within the entire genome.

Yet another application of the search engine is to detect differences between two genomes. For example, as the human genome project progresses, new segments of the genome are mapped and released to the public. Using the search engine and probes that were designed on another version of the same genome, it can be determined how many of those probes can be applied to the new version of the genome.

Yet still another application in which the search engine can be used is to verify whether a particular word exists in the genome. It may be desirable to find words that do not appear in the genome so that there is little chance that the word will hybridize to a section of the genome. These words may be generated randomly according to a predefined set of criteria. When a word is found, its complement is also submitted to the search engine to determine whether it appears in the genome. If both the word and its complement do not appear in the genome, it is known that both of these words will hybridize to each other and not to the genome.

A. System Description

Figure 7:
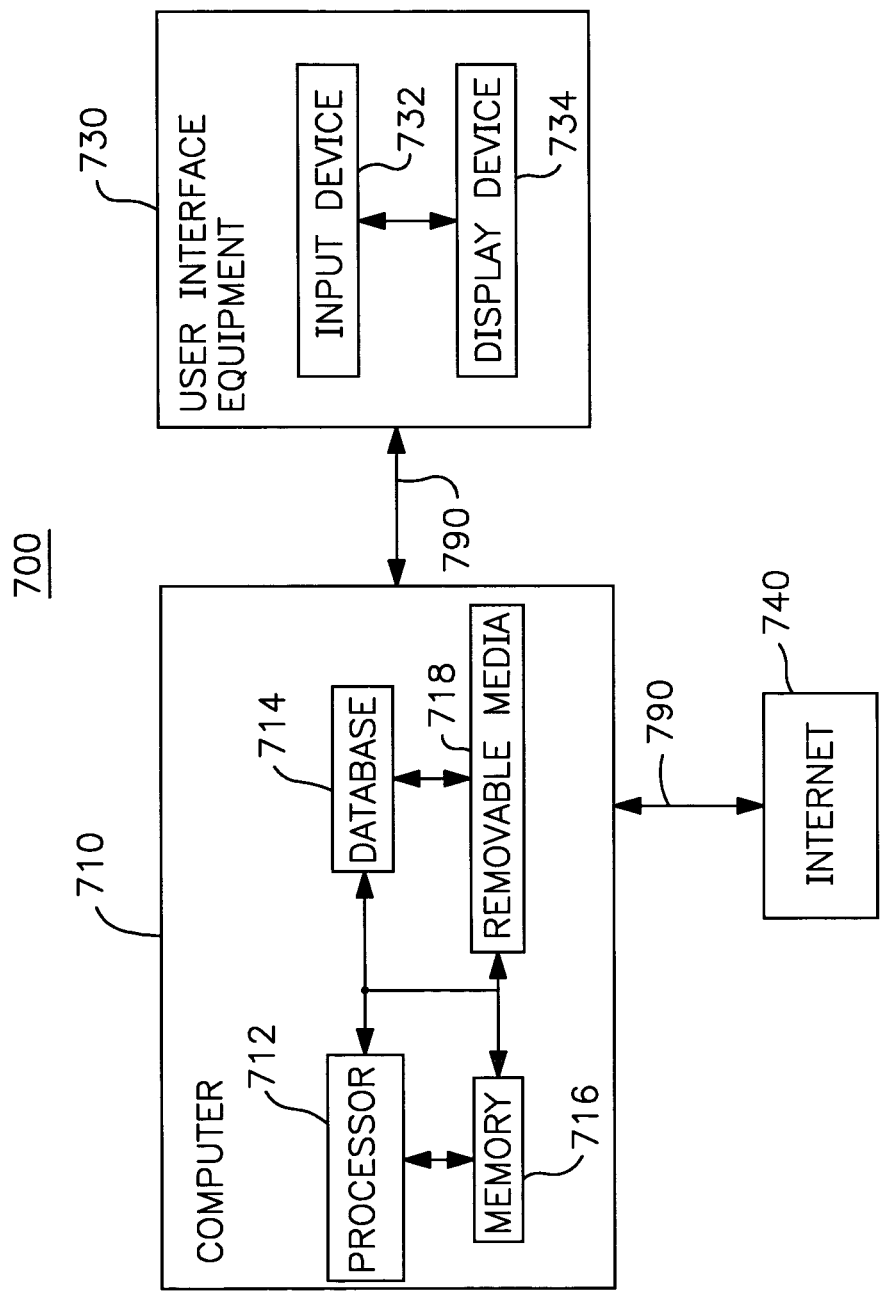
FIG. 7 shows a block diagram of an illustrative system in accordance with certain embodiments of the invention.

The search engine and applications thereof can be performed in accordance with the present invention using illustrative system 700 shown in FIG. 7. System 700 may include computer 710, user interface equipment 730, Internet 740, and optional laboratory equipment (not shown). System 700 may include multiple computers 710 and user interface equipment 730, but only one of each is illustrated in FIG. 7 to avoid complicating the drawing. Computer 710 is shown to be connected to user interface equipment 730, and Internet 740 via communication paths 790.

Computer 710 may include circuitry such as a processor 712, database 714 (e.g., a hard-drive), memory 716 (e.g., random-access-memory), and removable-media drive 718 (e.g., a floppy disk drive, a CD-ROM drive, or a DVD drive). This circuitry can be used to transmit data to, from, and/or between user interface equipment 730 and the Internet 740. Computer 710 may initiate techniques of the invention by responding to user input from user interface equipment 730. Computer 710 may also provide information to the user at user interface equipment 730 with respect to results obtained from operation of the search engine.

Database 714 stores information that provides the search engine with data. More particularly, database 714 may include the sequence of a genome or a particular portion of the genome. The invention may use the genome information stored on database 714 to construct a suffix array, which can also be stored on database 714. The suffix array is a data structure that is generated in preparation for constructing a transform of a genome or a portion thereof. Data representative of a genome may be obtained, for example, from a readable medium (e.g., a floppy diskette, a CD-Rom, or a DVD) which can be accessed through removable-media drive 718. Alternatively, genome data may be obtained through Internet 740, where the data is transmitted from a server located, for example, at a research facility (e.g., the National Institutes of Health or a university). If desired, database 714 may be updated with new genome data as it becomes available.

Generally, the quantity of data representing the suffix array is much larger than the quantity of data representing the genome. Therefore, database 714 may be more suitable for storing the suffix array than memory 712 because databases readily store more data than memory.

User interface equipment 730 enables a user to input commands to computer 730 via input device 732. Input device 732 may be any suitable device such as a conventional keyboard, a wireless keyboard, a mouse, a touch pad, a trackball, a voice activated console, or any combination of such devices. Input device 732 may, for example, enable a user to enter commands to perform a word count of a particular word, or perform statistical analysis of potential probes. A user may monitor processes operating on system 700 on display device 734. Display device 734 may be a computer monitor, a television, a flat panel display, a liquid crystal display, a cathode-ray tube (CRT), or any other suitable display device.

Communication paths 790 may be any suitable communications path such as a cable link, a hard-wired link, a fiber-optic link, an infrared link, a ribbon-wire link, a blue-tooth link, an analog communications link, a digital communications link, or any combination of such links. Communications paths 790 are configured to enable data transfer between computer 710, user interface equipment 730, and Internet 740.

Laboratory equipment may be provided in system 700 so that results obtained with the search engine can be directly applied to experiments, and vice versa.

An advantage of the search engine is that the techniques for counting exact word matches can take place entirely within the memory (e.g., memory 716) of the computer. This provides for extremely fast and efficient querying of the genome for exact word matches. There is no need to access a database (e.g., a hard-drive). Such a need can substantially hamper search engine performance. The techniques used for counting exact word matches are 100% accurate.

B. Suffix Array, Burrows-Wheeler Transform and Alphabounds

Figure 8:
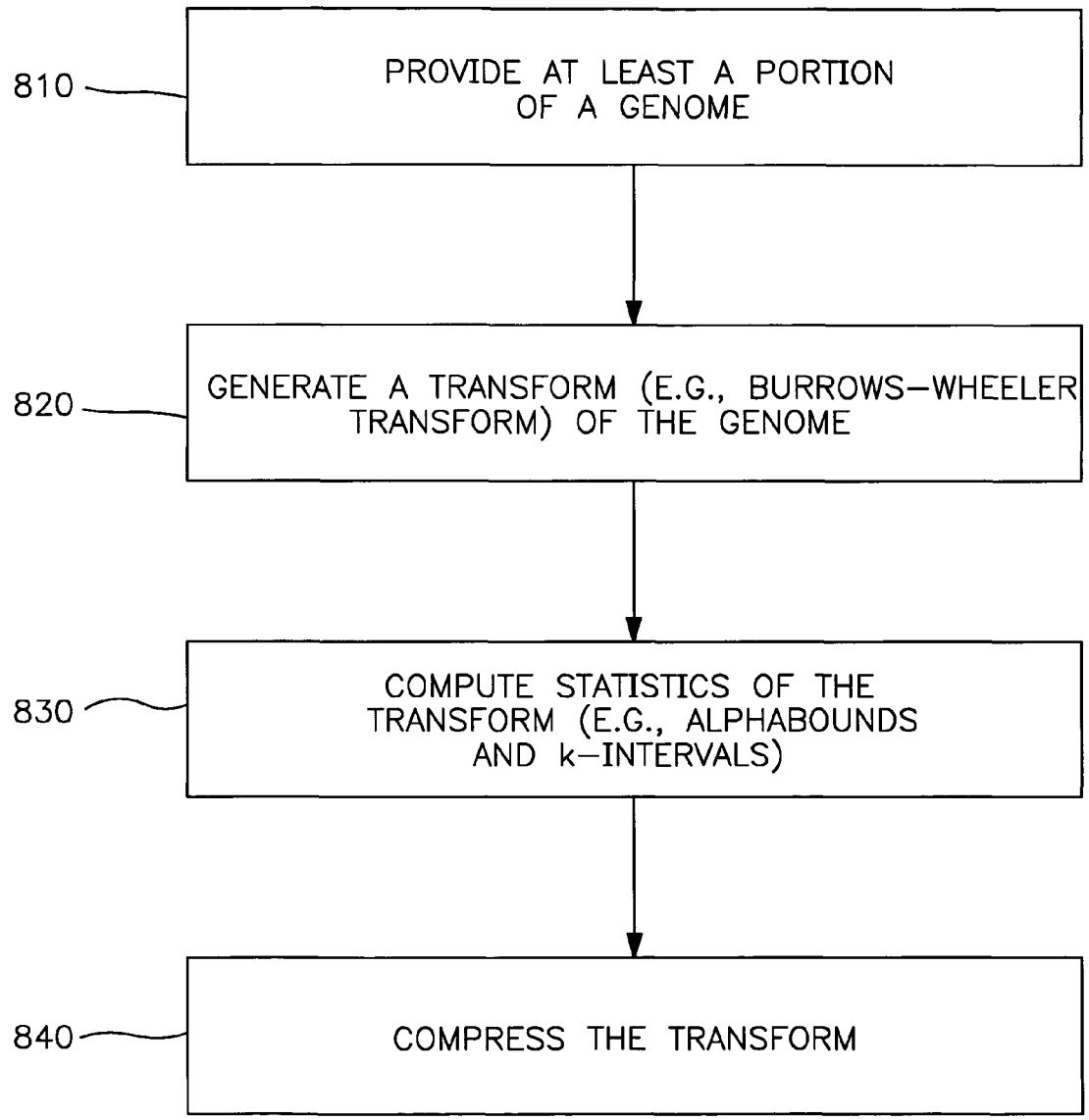
FIG. 8 shows a flow chart of an illustrative pre-processing step for performing exact word counts in accordance with certain embodiments of the invention.

Referring now to FIG. 8, illustrative flow chart 800 shows steps in preparing a genome for use in the search engine according to the principles of the present invention. Flow chart 800 uses techniques to build a suffix array data structure which provides the basis for generating a transform of a particular genome. This transform provides a basis for the search engine of this invention, where the search engine can rapidly count the number of occurrences of a particular word (e.g., a word having a length of 15, 21, 70 or 80 characters). At step 810 a nucleotide sequence such as a genome or a portion of a genome is provided. The genome may be arranged as a string of characters having a length of N nucleotides, where N represents the total number of nucleotides in the string of characters representing the genome.

The genome provided at step 810 can be derived from any organism or it can be randomly generated. For example, the entire known human genome may be provided or a portion of the human genome may be provided (e.g., a portion of the genome representing a chromosome or a region of a chromosome). If desired, non-human genome data may be provided such as the genomes of viruses, bacteria, single-celled and multi-celled organisms, including yeast, plant, and animals such as lizards, fish, and mammals (e.g., mice, rats, and nonhuman primates).

At step 820, the genome is subjected to a transformation process which reorganizes the nucleotide arrangement of the genome according to a predetermined lexicographical order. The transform maintains the same constituent letters (e.g., As, Cs, Gs, and Ts) that appear in the genome, but these letters are arranged in a different order. In one embodiment of the invention, the genome is subjected to a known transform called the Burrows-Wheeler transform. The Burrows-Wheeler transform can be obtained from a suffix array. According to this invention, a suffix array is an N×N matrix representing all the cyclical permutations of the genome, where the permutations are arranged according to predetermined criteria (e.g., alphabetical, numerical, etc.). Advantageously, the Burrows-Wheeler transform represents the sorted N×N matrix of the cyclical permutations. Thus, when the search engine of the present invention searches through the Burrows-Wheeler transform, it, by extension, searches through the suffix array, which by further extension, searches through the original string representing the genome.

Genome sequence assemblies can include an ambiguous character in addition to A, C, G, and T, thus extending the genome alphabet to five characters. This ambiguous character, commonly referred to as N, is typically used when the nucleotide at a particular position of a nucleic acid sequence is unknown.

Because the Burrows-Wheeler transform represents a sorted suffix array, there is no need to access the suffix array when searching for a particular string of characters. Preferably, the transform is stored in memory, where searching functions can be executed much faster than when the transform is stored on a hard-disk. Moreover, because the quantity of data contained in a suffix array can be substantial, the suffix array may have to be stored in a hard-disk drive, as opposed to faster operating memory (e.g., random access memory of a computer). For example, the size of a suffix array for the human genome is on the order of twelve gigabytes. If such an array were to be stored in memory, the cost of a machine having twelve gigabytes of memory would be much more costly than a machine having, for example, three gigabytes of memory. Therefore, one advantage of the search engine is that it does not require expensive and memory-intensive machines because the transform represents a condensed version of the sorted suffix array.

While the suffix array is not necessary for performing word searches according to this invention, it is useful to describe how such arrays are obtained in order to show the relationship between the transform and the array. The suffix array can be constructed by first obtaining the cyclical permutations of a nucleotide sequence. For example, Table 1 illustrates the cyclical permutations of the genome "AGACAGTCAT$," (SEQ ID NO: 1) where "$" is provided to mark the end of the genome string.

TABLE 1

| AGACAGTCAT$ | (SEQ ID NO: 1) |
|---|---|
| GACAGTCAT$A | |
| ACAGTCAT$AG | |
| CAGTCAT$AGA | |
| AGTCAT$AGAC | |

TABLE 1-continued

GTCAT$AGACA

TCAT$AGACAG

CAT$AGACGTC

AT$AGACAGTC

T$AGACAGTCA $AGACAGTCAT (SEQ ID NO: 1)

After the cyclic permutations are obtained, the rows are sorted according to predetermined criteria to obtain a particular lexicographic order (e.g., an alphabetical lexicographic order). For example, Table 2 illustrates an alphabetical arrangement of permutations shown in Table 1, under the heading, Sorted Array.

TABLE 2

| Row | Sorted Array | | Transform |
|---|---|---|---|
| 0 | $AGACAGTCAT (SEQ ID NO: 1) | -> | T |
| 1 | ACAGTCAT$AG (SEQ ID NO: 1) | -> | G |
| 2 | AGACAGTCAT$ (SEQ ID NO: 1) | -> | $ |
| 3 | AGTCAT$AGAC (SEQ ID NO: 1) | -> | C |
| 4 | AT$AGACAGTC (SEQ ID NO: 1) | -> | C |
| 5 | CAGTCAT$AGA (SEQ ID NO: 1) | -> | A |
| 6 | CAT$AGACAGT (SEQ ID NO: 1) | -> | T |
| 7 | GACAGTCAT$A (SEQ ID NO: 1) | -> | A |
| 8 | GTCAT$AGACA (SEQ ID NO: 1) | -> | A |
| 9 | T$AGACAGTCA (SEQ ID NO: 1) | -> | A |
| 10 | TCAT$AGACAG (SEQ ID NO: 1) | -> | G |

Once the cyclic permutations are sorted, the transform of the genome can be obtained by taking the last letter of each row of the sorted array. These letters are reproduced under the column heading "Transform," indicating that the transform of the genome "AGACAGTCAT$" (SEQ ID NO: 1) is "TG$C-CATAAAG."

In one embodiment, the suffix array of a genome such as the human genome can be built using a parallel radix sort using a 16-node cluster. Using this approach, the genome is divided into X number (e.g., 100) equal-size substrings, each overlapping by seven nucleotides, with X being a predetermined number. The offsets into the genome (i.e., the "genome" coordinate) within each substring are assigned to one of $5^7$ "prefix" bins according to the 7-mer (seven nucleotides) at each offset. The offsets within each prefix bin are sorted based on the sequence following the 7-mer prefix, thereby creating the suffix array.

At step 830, various statistics are computed to generate an auxiliary data structure, which can include an alphabounds data structure, a K-interval data structure, and a dictionary counts data structure. The alphabounds indicate how many adenine, cytosine, guanine, and thymine nucleotides there are in the transform. For example, using the genome of Tables 1 and 2, the alphabounds for A, C, G, and T are 4, 2, 2, and 2, respectively.

The alphabounds can be used to delimit ranges in the transform that correspond to particular characters existing at the front of each row of the sorted suffix array. For example, a delimited range for the nucleotide A includes each row of the suffix array that starts with A. Referring to Table 2, it shows that rows 1-4 of the sorted array start with A. Thus, the four rows correspond to the alphabounds computed for A. Table 2 shows that rows 5-6 begin with C, which correspond to the alphabounds computed for C. Likewise, the G block corresponds to rows 7 and 8, and the T block to rows 9 and 10 of the transform.

Step 830 may also generate K-intervals for every K number of characters in the transform, where K is a predetermined number. K-intervals may be used to keep a running total of each nucleotide as they appear in the transform. These K-intervals may be used by the search engine of the present invention to speed up the counting process, which is discussed below in connection with FIGS. 3 and 4. Specifically, the use of the K-interval enables the search engine to outperform and use less space than conventional word counting techniques, especially when applied to nucleotide sequences greater than four million characters in length.

The following example further explains how a transform is tabulated using K-intervals. Assume that the transform has the ten characters ACGTCAGTCA (SEQ ID NO: 2), and the K-intervals are stored every five characters. At the first interval, the K-interval includes one A, two Cs, one G, and one T. At the second interval (e.g., the tenth character) the K-interval includes a tabulation of all the nucleotides that have occurred in the transform thus far. The second K-interval includes three As, three Cs, two Gs, and two Ts.

At step 840, the Burrows-Wheeler string is compressed according to a predetermined compression ratio. Preferably the string is compressed using a 3-to-1 compression ratio. That is, for every three characters, the string is compressed to one character (e.g., 3000 characters is condensed down to 1000 characters). Those of skill in the art will appreciate that other compression ratios can be used. For example, a four-to-one or a five-to-one compression may be employed. The string can be compressed using a dictionary-based compression scheme, where one of 125 distinct single byte codes represents one of each of the $5^3$ possible three-letter substrings (e.g., AAA, AAC, . . . , TTT). More specifically, the transform is divided up into three character substrings and each substring is compressed according the dictionary based compression scheme. For example, if a three character substring is AAA, it may be equivalent to byte 0 of the dictionary compression scheme. Similarly, if the substring is TTT, this may be equivalent to byte 124 of the dictionary compression scheme.

The dictionary-counts data structure may be generated to assist the search engine in the counting process by providing a fast access lookup table for quickly identifying the number of times a particular letter occurs in a compressed byte. This is advantageous because it enables the search engine to perform counting operations on the transform while in its compressed state. It is noted, however, that a byte may have to be decompressed in order for the search engine to finish counting the number of times a particular letter occurs within a search region. On average, it has been found that a byte of the compressed transform is decompressed two-thirds of the time during the character counting step being performed by the search engine.

Once the transform is compressed, it is ready for use in the search engine of the present invention. Particularly the compressed Burrows-Wheeler transform can be queried to locate and count each occurrence of a particular word contained within the genome.

C. Word Counting Algorithm

Figure 9A:
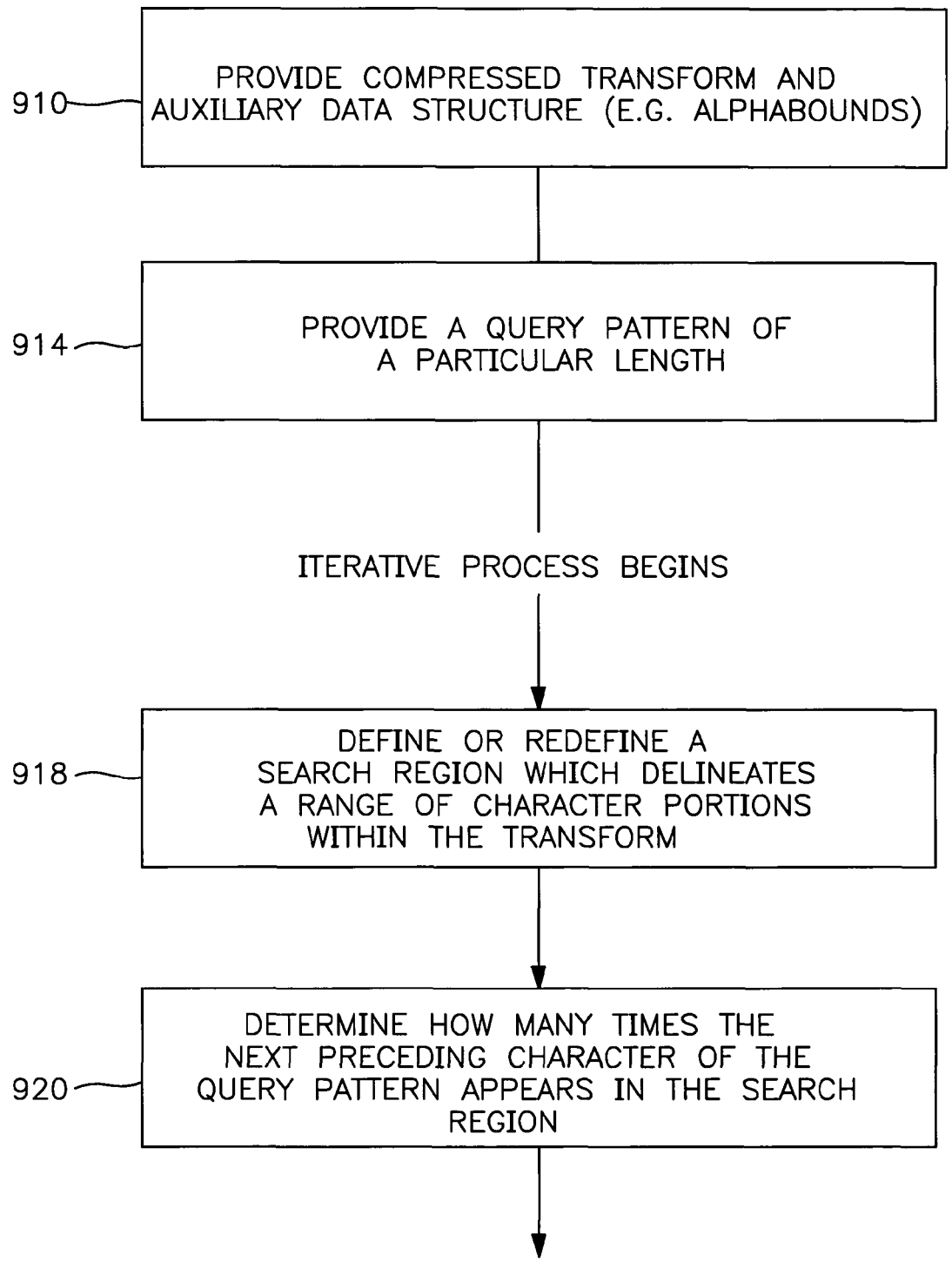
FIGS. 9A and 9B show a flow chart of an illustrative word counting algorithm in accordance with certain embodiments of the invention.
Figure 9B:
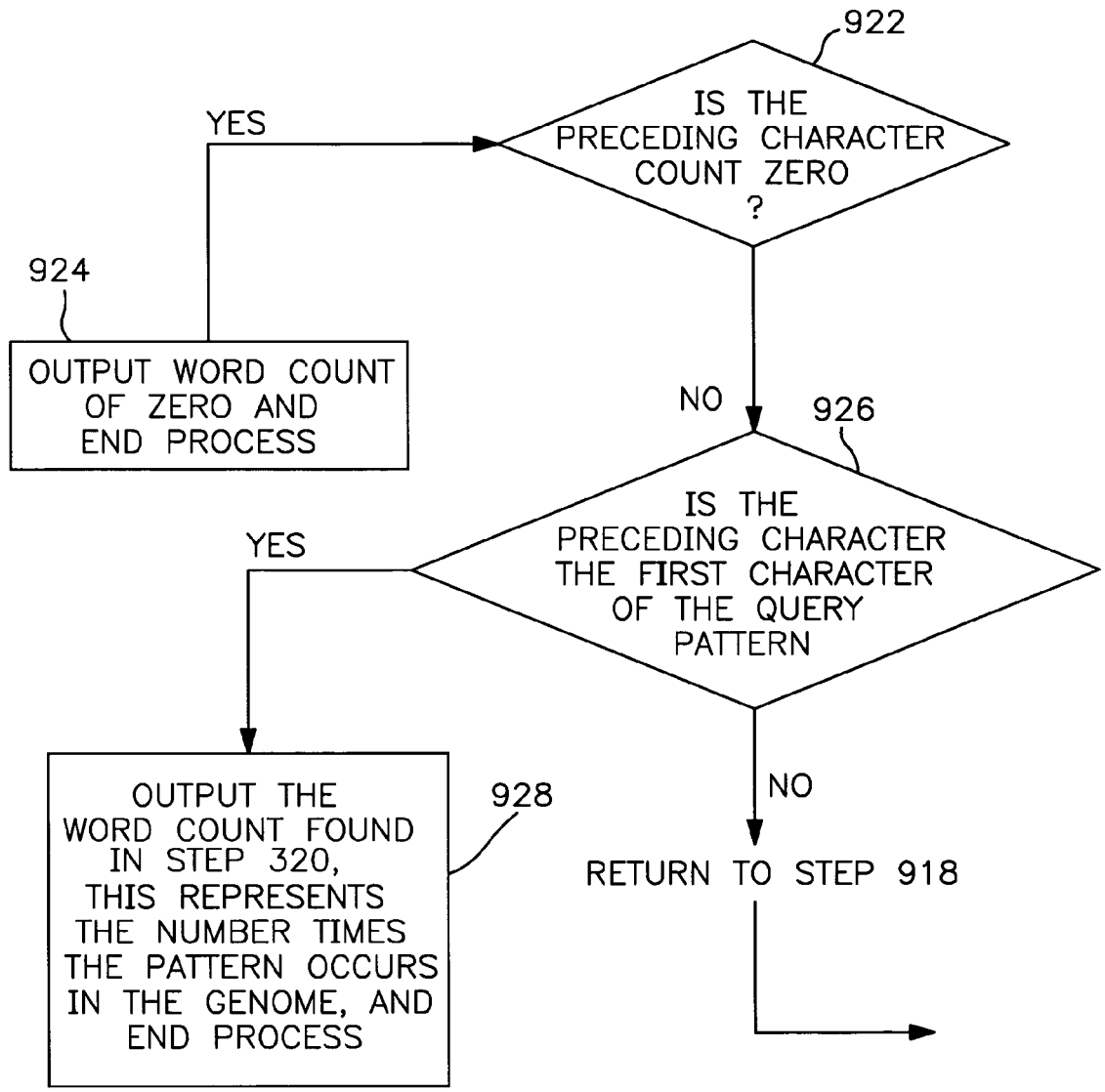

FIG. 9 shows a simplified flowchart of illustrative steps for counting the number of times a particular word exists in a given genome in accordance with the principles of the mer engine. Beginning at step 910, a compressed transform of the genome and an auxiliary data structure are provided. The compressed transform and the auxiliary data structure can be obtained, for example, from the flowchart illustrated in FIG. 8. At step 914, a query pattern of a particular length is provided (e.g., ACG ... G). The pattern is preferably a string of nucleotides that the search engine looks for in the transform of the genome.

After the query pattern is provided, the search engine begins an iterative searching process to determine whether the pattern exists. If the pattern does exist, it quickly and accurately outputs the number of times it appears. At step 918, the iterative process begins by defining (or redefining) a search region, which delimits a range of character positions within the transform. The search region delineates a block of characters starting at position X and ending at position Y of the compressed transform. This search region (or block) potentially contains all occurrences of the query pattern. The search region is defined using predefined criteria such as a particular character of the query pattern, alphabounds, and other data. A more detailed explanation of how the search region is defined is discussed in conjunction with the description accompanying FIG. 10.

At step 920, the process determines how many times the next preceding character of the query pattern appears in the search region. At step 922, if the proceeding character count is zero, the query pattern does not exist and the process ends (step 924). If at least one character is found within the delimited range, the process proceeds to step 926. At step 926, it is determined whether the preceding character is the first character in the query pattern. If so, the process proceeds to step 928, where the count obtained in step 920 is outputted and the process ends. If the preceding character is not the first character of the query pattern, the process loops back to step 918 because it has not yet been determined if the query pattern does or does not exist in the genome. At step 918, the search region is redefined using predetermined criteria.

More particularly, the search region is redefined using equations 1 and 2 below:

$$\text{Start Position} = A + Z \quad (1)$$

$$\text{End Position} = \text{Start Position} + M - 1 \quad (2)$$

where A is the start position of the preceding character according to the alphabounds, Z represents the number of times the preceding character occurs in the transform prior to the currently defined search region, and M represents the number of times the preceding character occurs in the currently defined search region.

The redefined search region also potentially contains all occurrences of the query pattern, but the newly defined search region further limits the character positions that need to be searched in step 920. After the new search region is defined, the process continues to step 920, where the next preceding character (i.e., the character proceeding the last character used in the previous step 920) of the query pattern is counted within the newly defined search region. This loop may repeat as many times as necessary before finding the first character of the query pattern, and consequently the number of word counts. If one of the preceding characters is not found in a search region, it will be concluded that no such pattern exists in the genome.

FIGS. 10A-B illustrate an example of the foregoing word counting algorithm. This example uses the illustrative genome (AGACAGTCAT$) (SEQ ID NO: 1), suffix array, Burrows-Wheeler transform (TG$CCATAAAG), and alphabounds described previously in connection with Tables 1 and 2. In this example, assume that a user wants to determine how many times the word "CAG" appears in the genome.

In FIG. 1A, the process begins by delimiting the G block because G is the last letter in the word "CAG." As illustrated, the G block begins at position 7 and ends at position 8 of the Burrow-Wheeler transform. These positions are obtained from the alphabounds. Once the G block is delimited, the engine searches for and counts the number of As, the next preceeding character of "CAG," existing within the G block. FIG. 10A shows that two As appear in the G block, thus indicating that the genome contains two occurrences of "AG."

If desired, K-intervals could be used to facilitate the step of counting the number of times a particular letter appears within a search region (e.g., counting the number of As in the G block) and can also be used to count the number of times a particular letter appears before a search region. To carry out such counting steps, the particular character is counted starting from a predetermined position (e.g., the start position) and progress to the nearest position that is a multiple of K. One advantage of using the K-intervals in connection with the search engine is that the time it takes to determine how many times a particular word appears in a genome is linear with respect to the K-intervals, the size of the word being searched, and the time required to access various memory addresses. Thus, the size of the genome is not a factor in determining the word count, unless the size of the compressed transform and the K-interval data structure are too large to fit in memory (e.g., random-access-memory). In one embodiment, the K can be set to 300 characters, or equivalently, 100 compressed bytes. With such an arrangement, the maximum number of counts that need to be performed does not exceed K/2.

If desired, subintervals of size K^ within each K-interval may be used to maintain a running total of each character occurring within a particular K-interval. If the size of K is limited to be less than $2^8$, for example, then the counts for each letter at every K-interval can be recorded using a single byte. This provides for increased density of the counting index by a factor of K/K^ while increasing the space requirements for the K-interval counts by a factor of only [(K/K^)/4]. Such subintervals and size constraints have been employed by the auxiliary data structure being used in connection with this algorithm. Depending on the choices of K and K^, a three to fivefold increase in query execution speed has been achieved while maintaining a memory requirement of less than two gigabytes for the human genome.

To further speed the counting process, the dictionary counts data structure can be used. Note that the compression scheme used is a 3:1 compression scheme, where bytes 0 through 124 decompress to "AAA" through "TTT" respectively. The dictionary-counts structure is a two-dimensional array that can be thought of as a matrix with 125 rows with five columns. Each row corresponds to one of the compression dictionary entries, and each column corresponds to each letter of the genome alphabet, A through T. The following explains by way of example how the dictionary counts structure and K-intervals can be used to perform counting operations.

Assume, for example, that the search engine is in the process of determining the number of As that occur before the search region. Using the K-interval counts structure described above, the engine can "jump" to within at least 50 bytes of the current start position of the search region in a single look-up. Further assume that the start position is pointing to the third "T" in a compressed "ATT" (a byte) which is the $49^{th}$ byte of the interval. For each of the 48 preceeding bytes, the byte itself can be used as the row number in the dictionary counts data structure, and the letter of interest, "A," represents the column number. Using this information as coordinates for accessing the dictionary counts array, the dictionary counts data structure provides the number times "A" appears in that compressed byte. Therefore, to determine how many As appear before the start of the search region, the dictionary counts structure needs to be access 48 times. In addition, the $49^{th}$ byte may need to be decompressed in order to examine the first two letters "AT" of the "ATT" byte.

Thus, when the dictionary counts data structure is combined with the K-intervals data structure, the step of counting any number characters requires only K/6+1 table look-ups, plus two character comparisons in the worst case.

Referring back to FIG. 10, the search engine then delimits the AG block within the transform so that it knows where to search for the next preceding character. The boundaries of the AG block are found by adding the number of times A precedes the G block in the transform to the first position that the A block begins in the transform. In this example, only one A occurs before the G block. Therefore, using equation 1 above, where A is 1 and Z is 1, a start position of 2 for the AG block is obtained. The ending position of the AG is obtained using equation 2 above, where M is 2 (number of As found in the G block). Equation 2 yields an AG Block end position of 3, as shown in FIG. 10B.

Once the AG block is found, the search engine counts the number of times C occurs therein. This count yields the number of CAGs that occur in the genome because C is the first character of the word "CAG." Thus, the search engine yields a word count of one.

Figure 11:
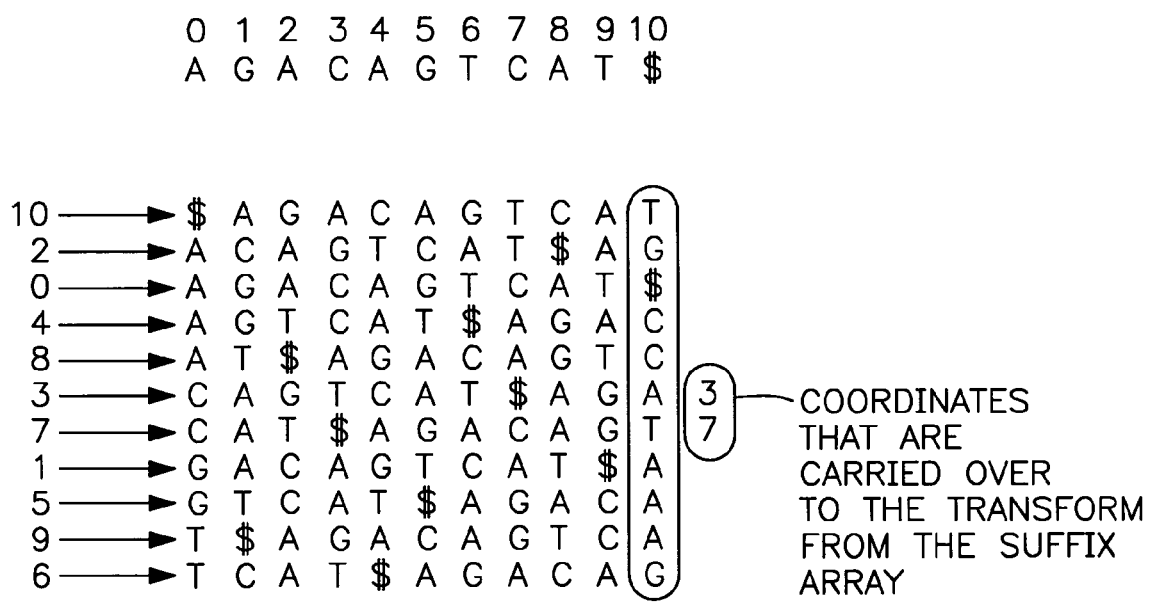
FIG. 11 shows an illustrative suffix array having coordinate positions corresponding to the coordinates of the genome in accordance with certain embodiments of the invention. The AGACAGTCAT 10-mer is SEQ ID NO: 1.

FIG. 11 shows an illustrative genome having coordinate positions and a sorted suffix array that has coordinate positions corresponding to the genome's coordinate positions. That is, the first character in each row of the suffix array corresponds to one of the characters in the genome. For example, the second row of the array has a coordinate position of 2, which corresponds to position two of the genome. Thus the coordinate positions of the suffix array correlate to the coordinate positions of the genome.

If desired, the suffix array can be used to locate the coordinate position of a particular word. For example, if the coordinate position of "CAG" is being sought, the suffix array of FIG. 11 can be accessed and it will indicate that CAG starts at position 3. However, as mentioned above, accessing the suffix array is a time consuming process because it requires harddisk drive access. Therefore, it is desirable to obtain word coordinates by only accessing memory. This can be achieved by assigning preselected suffix array coordinates to the transform, thereby allowing a coordinate location algorithm to use the transform to locate the starting coordinate of a particular word.

Such a coordinate location algorithm is explained by way of example. Assume that the circled portion of the suffix array is the transform of the genome and that only coordinates 3 and 7 have been carried over to the transform from the suffix array. Further assume that it is desired to find the coordinates of TC. (Note that if the transform had coordinates associated with the G that is affiliated with TC, the coordinates of TC would be known without having to resort to using the coordinate location algorithm.) It is known that the TC is associated with the last G in the transform. Starting with this G, the algorithm determines how many preceding G's there are. In this case, there is one preceding G.

The alphabounds data structure and the number of preceeding G's are used to determine which letter precedes this particular G. Using the alphabounds, it is known that the G block starts at position 7. Since there is one preceding G, the algorithm adds this number to 7 to obtain 8. Thus, the A that corresponds to the suffix array string that starts with GT is the letter that precedes the aforementioned G. This completes one iteration of the coordinate location algorithm. Generally speaking, this iteration is repeated until a coordinate (e.g., 3 or 7) on the transform is reached. Once a coordinate is reached, the number of iterations is added to the coordinate and the resulting sum is the actual starting coordinate position of the desired word (e.g., TC).

Continuing with the iterative process, it is known that two As precede the A associated with the suffix array string beginning with GT. Using the alphabounds and the number of preceding A's, the algorithm settles on the C associated with the suffix array beginning with AGT. Since there are no C's preceding this particular C, the algorithm settles on the A associated with the suffix array string starting with CAG. Because this A has a coordinate position (e.g., 3), the actual position of the word TC can be determined by adding 3 (the coordinate position of this A) to the number of iterations, which in this example is 3, resulting in a coordinate position of 6. Thus, TC begins at the coordinate position of 6 in the original genome.

D. Applications of the Search Engine

Now that the operative features of the search engine have been described, practical applications of the engine can be discussed. One application of the search engine is that it can be used to annotate a genome (or any other type of nucleotide sequence). Particularly, the genome can be annotated using substrings of a particular length that exist within the genome. The search engine can then count the number of times a particular length substring occurs in the genome. These counts provide an indication of the uniqueness of a particular substring, where lower counts represent a higher degree of uniqueness than higher counts.

If desired, any region of the genome or the whole genome may be annotated based on its constituent "mer" frequencies. A "mer" is another term for a word or substring of a particular length. Thus when a genome or a portion thereof is being annotated, it is annotated based on mers of a particular length (e.g., mer lengths of 15, 18, 21, and 24). Regardless of the mer length being annotated, every mer of that length that exists in the genome is counted. For example, if the mer length is 15, the search engine will determine the word count for the first 15-mer and each 15-mer occurring thereafter. Each succeeding 15-mer overlaps the previous 15-mer word by one character. That is, characters 1 through 15 constitute a 15-mer, characters 2 through 16 constitute another 15-mer, characters 3 through 17 constitute yet another 15-mer, and so forth. This ensures that every annotated 15-mer is assigned a word count, such that the word count represents the number of times that particular 15-mer occurs in the entire genome.

Probe design is facilitated by using the search engine. The engine's ability to rapidly count the number of times a particular word appears in a genome is useful in designing probes that are unique and hybridize to a specific region of DNA with minimal cross-hybridization. By using the search engine, potential cross-hybridizations can be minimized by selecting a candidate probe that is comprised of smaller mers that are unique and meet certain stringency conditions such as having low or no word counts within the entire genome. A unique word may be a particular string of nucleotides that have less than a predetermined number of word counts (e.g., less than 2, 5, 10, 25, 50, or 100 word counts) or an absence of word counts (e.g., zero word counts) within a genome of portion thereof.

More particularly, candidate probes are obtained based on a set of predetermined criteria such as requiring the candidates to have a length, L1, and also requiring that the candidates have a predetermined word count (e.g., a candidate probe having a word count of one). In addition, the predetermined criteria can also require that the reverse complement of a candidate to have a predetermined word count (e.g., one). Once the candidates are obtained, they are subjected to additional predetermined criteria to determine which candidates are suitable for use as probes. These additional criteria are used to filter the candidates based on their constituent subregions (i.e., mers of a length contained within the candidate probe). For example, the filtering criteria may require a mer of length L2, where L2 is less than L1, to have word counts that are minimized relative to other probe candidates. Thus, a relationship exists among the criteria used in finding probes—a relationship between "hard" constraints (e.g., in which each candidate is unique with respect to the genome) and "soft" constraints (e.g., in which the constituent mer counts are minimized).

One way to satisfy the "hard" constraints is to obtain candidates based on the results of a previously performed annotation. Using word count information, candidates can be selected from regions of the genome having low concentrations of word counts (e.g., it is preferable to obtain candidates having a minimum mean value of word counts of a predetermined length, a geometric mean value of word counts of a predetermined length, a mode value of word counts of a predetermined length, a minimized maximum value of word counts of a predetermined length, a sum total value of word counts of a predetermined length, a product value of word counts of a predetermined length, a maximum length string of a particular nucleotide, or a combination thereof).

To satisfy the "soft" constraint, the candidates can be annotated according to predefined criteria such as 15-mer counts, 17-mer counts, etc. The data obtained from the annotation is analyzed to determine whether a candidate is unique enough to be used as a probe. A candidate may be selected as a probe if, for example, it has the lowest sum of 15 mer counts of all the candidates. Other criteria such as minimal occurrences of composition bias (e.g., long strings of a particular nucleotide) can be applied to determine which probe is best. After the criteria are applied to each candidate, the one or more candidates are selected as suitable probes.

Yet another application of the search engine is to detect changes from one genome to another. For example, as the human genome project progresses, new segments of the genome are mapped and released to the public. Using the search engine and probes that were designed on another version of the same genome, it can be determined how many of those probes can be applied to the new version of the genome.

Yet still another application in which the search engine can be used is to verify whether a particular word exists in the genome. It may be desirable to find words that do not appear in the genome so that there is little chance that the word will hybridize to a section of the genome. These words may be generated randomly according to a predefined set of criteria. When a word is found, its complement is also submitted to the search engine to determine whether it appears in the genome. If both the word and its complement do not appear in the genome, there is a minimal chance that this word and its complement will hybridize to the genome. Such non-hybridizing probes can be used in hybridization as readable barcodes and in hybridization array controls, and can be added to nucleic acid probes for the purpose of enhancing hybridization signals through network formation.

One way to minimize the chance of hybridization is to minimize the frequency of a particular word's constituent mers. That is, it is preferable to obtain probes that have as many constituent mer lengths that have word counts of zero. For example, assume that several 20-mer oligonucleotides are generated with the aim of not hybridizing to the human genome. Then, further assume that each 20-mer is annotated for each of its constituent overlapping 19-mers, 18-mers, 17-mers, 16-mers, down to, for example, 6-mers. Theoretically, the most desirable 20-mer would preferably have zero word counts for each length mer. In practice, a probe that has minimal chance for hybridization preferably has as many mer counts of zero as far down in the mer lengths as possible (e.g., a desirable probe may have zero word counts for mer lengths of 19, 18, 17, 16, 15, 14, and 13). Thus, if one probe has zero counts of its constituent 15 and 14-mers, it is less likely to hybridize to the genome than a probe that has zero counts of its constituent 15-mers, but has one or more counts of its constituent 14-mers. Thus, the former probe has less of an opportunity to hybridize than the latter probe because it does not have any 14-mers that match with sections of the genome.

Non-hybridizing oligonucleotides can be constructed using constituent mers of a particular mer that have a zero or low word count. For example, if a particular 20-mer has a 13-mer that has a zero word count, this 13-mer can be used to build oligonucleotides that probably do not exist in the genome (e.g., two of these 13-mers can be attached to each other to create a unique 26-mer).

In a laboratory setting, for example, a zero count word and its zero count complement (non-hybridizing oligonucleotides) can be attached to a (hybridizing) probe or target word. In an abstract sense, the words are the "arms" that are attached to the "body" (i.e., the probe). When hybridization commences, the words ("arms") only hybridize to each other, while the probe hybridizes to the genome. Because the words ("arms") typically carry a detectable material (e.g., a fluorescent label) the self hybridization helps a person distinguish the probe's location within the genome against background hybridization. Thus, the self hybridization of the arms serves to amplify visibility of the probe that is hybridized to the genome.

The non-hybridizing oligonucleotides can also be used as tags to uniquely identify a particular sequence among a vast population of other sequences. The non-hybridizing oligonucleotides can be attached to the known sequence, thereby tagging or labeling a particular sequence.

In yet another example, several different DNA sequences can be concatenated to form the single genome (e.g., provided, for example, at step 810 of FIG. 8). Such a concatenated genome is useful, for example, if it is desired to design a probe that detects the presence of a particular pathogen (e.g., a virus) within a human blood sample. A concatenated genome is needed because the DNA extracted from human blood not only contains human DNA, but also DNA from other sources such as the pathogen. Therefore, in order for the probe to effectively detect the pathogen in human blood, it should not cross hybridize to the human genome.

In the event that the pathogen probe is not completely unique with respect to the other genomes in a tissue sample (e.g., the patient's genome and genomes of other microorganisms found in the patient), it may be necessary to compare the word count for the probe in the pathogen genome with the word counts for the probe in the other genomes. This approach may require two search engines—one for the pathogen of interest, and the other for a combination of the other genomes. Note that in applying this dual search engine approach, it may be advantageous to design probes that have high mer counts within the pathogen genome, as long as the probe counts in the other genomes in the tissue sample are disproportionately low.

VII. EXAMPLES

The following examples are provided by way of illustration only. They are not intended to limit the scope of the invention disclosed herein.

Example 1

Selection of Oligonucleotides Complementary to a Representation

This example demonstrates the identification of oligonucleotide probes that are complementary to a BglII-derived representation of a human genome. Similar approaches may be used to design oligonucleotides complementary to any population of nucleic acids whose sequences are known or predicted. Using the published draft assembly of the human genome sequence, we performed an in silico BglII digestion of the human genome by locating all BglII restriction sites within the draft assembly. We further selected all sequences of BglII fragments that were between 200 to 1,200 basepairs in length. We then analyzed the sequences of these fragments using an algorithm described herein. This algorithm (also called "a mer-engine") can be used to determine the copy number of any given oligonucleotide sequence in any sequenced genome. This copy number is also called the "word count" of the oligonucleotide sequence in the genome.

We annotated each BglII-digested fragment with the word counts of their constituent, overlapping 15- and 21-mers (i.e., oligonucleotides having 15 or 21 nucleotides) using the mer-engine constructed from the same draft assembly of the human genome. To do this, we generated in silico for each fragment every constituent, overlapping 70-mer oligonucleotide (e.g., a 100 basepair fragment would have 31 such 70-mers). The following attributes were determined for every such 70-mer of a fragment as described below: maximum 21-mer count (or maximum 18-mer count), arithmetic mean of 15-mer counts, percent G/C content, and quantity of each base, and the longest run of any single base.

To determine the maximum 21-mer count, we broke each 70-mer into overlapping 21-mers and compared each of these 21-mers against all of the 21-mer sequences in the genome. We discarded all 70-mers whose maximum 21-mer count was greater than 1, i.e., those with a 21-mer sequence that was 100% complementary to more than one 21-mer sequence in the genome. This was our initial set of 70-mer probes.

We further optimized the 70-mer probe set by removing those with a GC content less than 30% or greater than 70%, a run of A/T greater than 6 bases, or a run of G/C greater than 4 bases. From the remaining 70-mers, we chose for each BglII fragment the one (or more) 70-mer which had a GC/AT proportionality closest to that of the genome as a whole. We further analyzed each of the thus-chosen 70-mers by determining the genome word count for each of the 70-mer's constituent, overlapping 15-mers. We chose 70-mers that had the lowest mean 15-mer count.

As a final check for overall uniqueness, the optimal 70-mer probes for each BglII fragment were compared to the entire genome using the BLAST software program. Default parameters were used with the exception of filtration of low complexity sequence, which was not performed. Any 70-mer probe with any degree of homology along 50% or more of its length to any sequence other than itself was eliminated.

The mer-engine algorithm affords rigor, flexibility and simplicity to the probe design process. The ability to rapidly determine word counts for words of all sizes allows design criteria to be framed quantitatively in a way that is analogous to real hybridization events. The word counts can be considered as a quantitative measure of the degree to which sequences belong to two or more sets of polynucleotides. For instance, the small probe "AGT" can be thought of as a set containing six distinct words, namely "A", "G," "T," "AG," "GT," and "AGT." If this probe were annotated with word counts for all words of all sizes, it would be discovered that the number of times each word appears in the first set, that being the probe "AGT," would be vastly overshadowed by the number of times they appear in the second set, namely the three billion nucleotide genome.

This relationship can be expressed as a ratio X/Y, where X is the sum of counts for all of a probe's constituent words relative to said probe and Y is the sum of counts for all of the same words within the genome. When selecting a 70-mer probe that hybridizes to a target sequence with minimal cross-hybridization, one can maximize the ratio X/Y, where the maximum value of X/Y for probes derived from the genome sequence is 1. The technique of selecting only two word lengths with which to annotate is essentially one of many possible short cuts toward this goal.

In the event that no unique probes can be found within a genomic region of interest, it is possible to make use of non-unique probes to provide clear measurements of relative copy number differences or simply the quantity of matter. The problem then extends to a comparison between three sets of words: the probe, the encompassing region of interest, and the genome. Let Z represent the sum of all probe word counts relative to the encompassing region. Assume that X and Y still represent the sums of all probe word counts relative to the probe and the genome respectively. The goal is then to maximize the value of the expression, (X/Y)/(X/Z), or simply, Z/Y. In other words, one can find probes that are region-specific regardless of the overall copy number. This special case can be generalized to include any circumstance in which one is selecting probes to recognize one particular entity out of many through hybridization. A further example is the recognition of the DNA of one organism when exposed to the DNA of many other organisms.

Yet another application of this paradigm is that of minimization of set membership. We have designed probes that acted as hybridization controls in microarray experiments. These probes were controls in the sense that they were intended to hybridize to only those fragments of DNA that any other probe had an equal chance of recognizing. The goal in this case was simply to design a probe where Y was as close to zero as possible. Such a probe will also be useful, e.g., as hybridization-readable unique identifiers or as additions to other nucleic acid sequences for enhancing hybridization signal through networking.

In addition to sums and arithmetic means of word counts, many other statistics can be used, including, for example, the variance of a probe's word counts for words of a particular size. This variance can act as a rapid prescreen for the selection of probes that must exist in a particular copy number. The maximum word count for a particular word size can be taken as an indication of the worst possible hybridization outcome for an otherwise unique probe. These quantitative measures are ideal for rapidly determining the fitness of a hybridization probe relative to other candidates. The mer-engine algorithm in essence can reduce the process of probe selection to a single pass scan over the sequence of interest.

One of the probe sets that we designed consisted of 85,000 70-mers, possessed a mean 18-mer count relative to the human genome of 1.2 with a standard deviation of 0.8. The mean was calculated over the set of all 18-mers of all probes combined. Compared with the prior art, in particular a published set of approximately 23,000 70-mer expression array probes, the mean of the 18-mer counts for all probes combined was 1.9 with a standard deviation of 14.8. Therefore, this set of probes was the larger of the two by a factor of 4, and was more consistently unique by a factor of 18. The set of 85,000 probes in this example were selected by us based on the combination of a unique 21-mer constraint and a minimized aggregate 15-mer count constraint as previously described. The advantages included a large increase in confidence that probes that proved to perform well empirically were not simply hybridizing to a large heterogeneous population of DNA fragments and thereby increasing their signal. This further illustrates the precision with which probe sets can be designed to satisfy rigorously defined criteria, such as an extremely small standard deviation about a target mean word count.

Example 2

Preparation of Arrays

We used two formats for constructing microarrays containing oligonucleotide probes designed according to Example 1. In the first of these, the "print" format, we purchased about 10,000 oligonucleotides made with solid phase chemistry, and printed them with quills on a glass surface. Specifically, we used the Cartesian PixSys 5500 (Genetic Microsystems) to array our probe collection onto the slides using a 4×4 pin configuration. The dimensions of each printed array was roughly 2 cm². Our arrays were printed on commercially prepared silanated slides (Corning® ultraGAPS™ #40015). Pins used for the arrayer were from Majer Precision.

In the second format, the "photoprint" format, oligonucleotides were synthesized by NimbleGen™ Systems, Inc. directly on a silica surface using laser-directed photochemistry. Approximately 700,000 unique 70-mer oligonucleotides were first screened for "performance" by arraying them onto eight chips and hybridizing them with BglII and EcoR1-depleted BglII representations of genomic DNA from a normal male J. Doe. We picked the 85,000 oligonucleotides that generated the strongest signal and arrayed them on a single chip.

In both formats, we arrayed the oligonucleotides in a random order to minimize the possibility that a geometric artifact during array hybridization would be incorrectly interpreted as a genomic lesion. In subsequent examples, we describe results with the 10K printed arrays and the 85K photoprint arrays.

Example 3

Preparation and Labeling of Test Representations

For some experiments described herein, we chose BglII to make the representations. BglII has characteristics useful for these particular experiments: It is a robust enzyme; its cleavage site is not affected by CpG methylation; it leaves a four base overhang; and its cleavage sites have a reasonably uniform distribution in the human genome. BglII representations are made up of short fragments, generally smaller than 1,200 bps. We estimated that there are about 200,000 of them, comprising about 2.5% of the human genome, with an average spacing of 17 kb.

In all of the experiments described herein, we used comparative hybridization of representations prepared in parallel. The DNA from two samples being compared were prepared at the same time, and representations prepared from the same concentration of template, using the same protocols, reagents and thermal cycler. This would diminish the possible "noise" created by variable yield upon PCR amplification.

We prepared BglII representations of human genomic DNA as previously described by Lucito et al., 1998, supra. Briefly, we digested 3-10 ng of human genomic DNA with BglII under conditions suggested by the supplier. We purified the digest by phenol extraction and ethanol precipitation in the presence of 10 µg of tRNA. We resuspended the pellet in 30 µl of 1×T4 DNA ligase buffer with 444 pmol of each adaptor (RBgl24 and RBlg12; Lucito, R. and M. Wigler. 2003. "Preparation of Target DNA." In Microarray-based Representational Analysis of DNA Copy Number (eds. D. Bowtell & J. Sambrook), pp. 386-393. Cold Spring Harbor Press, Cold Spring Harbor, N.Y.). We placed the reaction mixture in a preheated 55° C. heat block and placed the heat block on ice for approximately 1 hour until the temperature had dropped to 15° C. We then added 400 units of T4 DNA ligase and incubated the reaction mixture at 15° C. 12-18 hours.

We added $\frac{1}{40}$th of the ligated material, 20 µl of 5×PCR buffer [335 mM Tris.HCl, pH 8.8; 20 mM $MgCl_2$; 80 mM $(NH_4)_2SO_4$; 50 mM β-mercaptoethanol and 0.5 mg/ml BSA], 2'-dideoxynucleoside 5'-triphosphates to a final concentration of 0.32 mM, RBgl24 adaptor to a final concentration of 0.6 µM, 1.25 U of Taq polymerase and water to a 250 µl tubes to bring the volume to 100 µl. The tubes were placed into an MJ Research TETRAD™ thermocycler preheated at 72° C. We then conducted the amplification as follows: one cycle at 72° C. for 5 minutes, and then 20 cycles of 1 minute at 95° C. and 3 minutes at 72° C. followed by a 10 minute extension time at 72° C. We cleaned the representations (i.e., the PCR products) by phenol:chloroform extraction and ethanol precipitation before resuspending in TE (pH 8) and determining the DNA concentration.

For certain experiments, we prepared depleted representations by digestion with an additional restriction endonuclease to cleave those fragments that contained its restriction site. In these cases, we digested the ligation mixture with the second restriction endonuclease just before the amplification step. In the experiments described below, the depleted BglII representation was produced using HindIII.

We labeled fragments in the representations by placing the DNA in a 0.2 ml PCR tube. We added 10 µl of primers from the Amersham-Pharmacia Megaprime™ labeling kit and mixed them well with the DNA. We brought the volume up to 100 µl with water. We placed the tubes in an MJ Research TETRAD™ machine at 100° C. for 5 minutes, placed on ice for 5 minutes and added 20 µl of labeling buffer from the Amersham-Pharmacia Megaprime™ labeling kit, 10 µl of label (either Cy3™-dCTP or Cy5™-dCTP) and 1 µl of New England BioLabs® Klenow fragment. We incubated the tubes at 37° C. for two hours, combined the labeled samples (Cy3™ and Cy5™) into one Eppendorf® tube, and then add 50 µl of 1 µg/ul Human Cot 1 DNA, 10 µl of 10 mg/ml stock yeast tRNA, and 80 μl of Low TE (3 mM Tris pH 7.4, 0.2 mM EDTA). We loaded the sample on a Centricon® Filter and centrifuged for 10 minutes at 12,600 rcf. We discarded the flow through and washed the filter with 450 μl of Low TE. We repeated the centrifugation and TE wash twice. We collected the labeled sample by inverting the Centricon® column into a new tube and centrifuging for 2 minutes at 12,600 rcf. We transferred the labeled sample to a 200 μl PCR tube and adjusted the volume with Low TE to 10 μl.

In addition, for some experiments, we digested DNA isolates from a primary ovarian cancer cell and from normal reference with McrBC and ligated linkers and amplified as described above.

Example 4

Hybridization of Test Representations to Arrays

We UV-crosslinked the oligonucleotide probes to the slide using a Stratagene® Stratalinker® set at 300 mJ, rotated the slide 180 degrees, keeping the slide in the same spot in the crosslinker, and repeated the treatment. We washed the slides for 2 minutes in 0.1% SDS, 2 minutes in Milli-Q® water, 5 minutes in boiled Milli-Q® water, and finally in ice cold 95% benzene-free ethanol. We dried the slides by placing them in a metal rack and spinning them for 5 minutes at 75 rcf. We prehybridized the printed microarrays by placing them in a coplin jar or other slide processing chamber, adding prehybridization buffer (25% deionized formamide, 5×SSC and 0.1% SDS) and preheating the chamber to 61° C. for two hours and then washed them in Milli-Q® water for 10 seconds. We again dried the slides by placing them in a metal slide rack and spinning for 5 minutes at 75 rcf. NimbleGen™ photoprinted arrays did not require UV-crosslinking or prehybridization.

We added 25 μl of hybridization solution to 10 μl of labeled sample prepared as in Example 3 and mixed. For printed slides, the hybridization solution was 25% formamide, 5×SSC, and 0.1% SDS. For NimbleGen™ photoprinted arrays, it was 50% formamide, 5×SSC, and 0.1% SDS. We denatured the samples in an MJ Research™ TETRAD™ at 95° C. for 5 minutes and then incubated at 37° C. for 30 minutes. We spun down the samples and pipetted them onto a slide prepared with lifter slip and incubated it in a hybridization oven (such as the Boekel InSlide Out™ oven) set at 58° C. for printed arrays or 42° C. for NimbleGen™ photoprinted arrays for 14 to 16 hours.

After hybridization, we washed the slides as follows: briefly in 0.2% SDS/0.2×SSC to remove the coverslip; 1 minute in 0.2% SDS/0.2×SSC, 30 seconds in 0.2×SSC; and 30 seconds in 0.05×SSC. We dried the slides as before by placing them in a rack and spinning them at 75 rcf for 5 minutes. We then scanned the slides immediately.

We scanned the slides using an Axon GenePix® 4000B scanner set to a pixel size of 10 microns for printed arrays and 5 microns for photoprinted arrays. We quantified the intensity of the arrays using GenePix™ Pro 4.0 software and imported the data into S-PLUS® for further analysis. We calculated the ratios between two signals in an experiment using measured intensities without background subtraction. We normalized the data using an intensity based lowess curve fitting algorithm similar to that described in Yang et al., Nucl. Acids Res. 30: e15-15 (2002). We averaged the data obtained from color reversal experiments and displayed it as presented in the figures.

Example 5

Performance and Validation of Arrays

As discussed above in Example 1, we should be able to predict based on the published human genome sequence which oligonucleotide probes could hybridize with which representations. To confirm this, we tested our 10K printed arrays by hybridizing them to BglII representations of normal human genomic DNA labeled with one fluorescent dye and to HindIII-depleted BglII representations of the same DNA labeled with another fluorescent dye.

FIG. 1 illustrates results obtained with BglII representations depleted by HindIII. In FIG. 1A, we graph the ratios of hybridization intensity of each probe along the Y-axis. Each experiment was performed in color reversal, and the geometric mean of ratios from the separate experiments is plotted. Probes predicted to detect fragments in both the full and depleted representations did hybridize to both (FIG. 1A; left). There were about 8,000 of these probes. Probes predicted not to detect probes in the depleted representation did not (FIG. 1A; right). There were about 1,800 of these probes. These results validate that: (1) the restriction profile of representational fragments was correctly predicted, (2) the oligonucleotides were correctly arrayed, and (3) the oligonucleotides detected the predicted probes with acceptable signal intensity. In FIG. 1B, the agreement between the ratios of the color reversal experiments is graphed. These data confirm the reproducibility of our array.

A very small number of oligonucleotide probes failed to hybridize to target fragments in the representations as predicted. For instance, of the 8000 probes predicted to hybridize to fragments not cleaved by HindIII, about 16 appeared to hybridize BglII fragments that were in fact cleaved. This could be due to a divergence between our sample and the published human sequence, which could result from polymorphism or sequencing errors. However, the data here show that the public human sequence is sufficiently reliable for the design of probes for representational oligonucleotide microarrays.

Example 6

Global Analysis of Tumor Genomes

Figure 2:
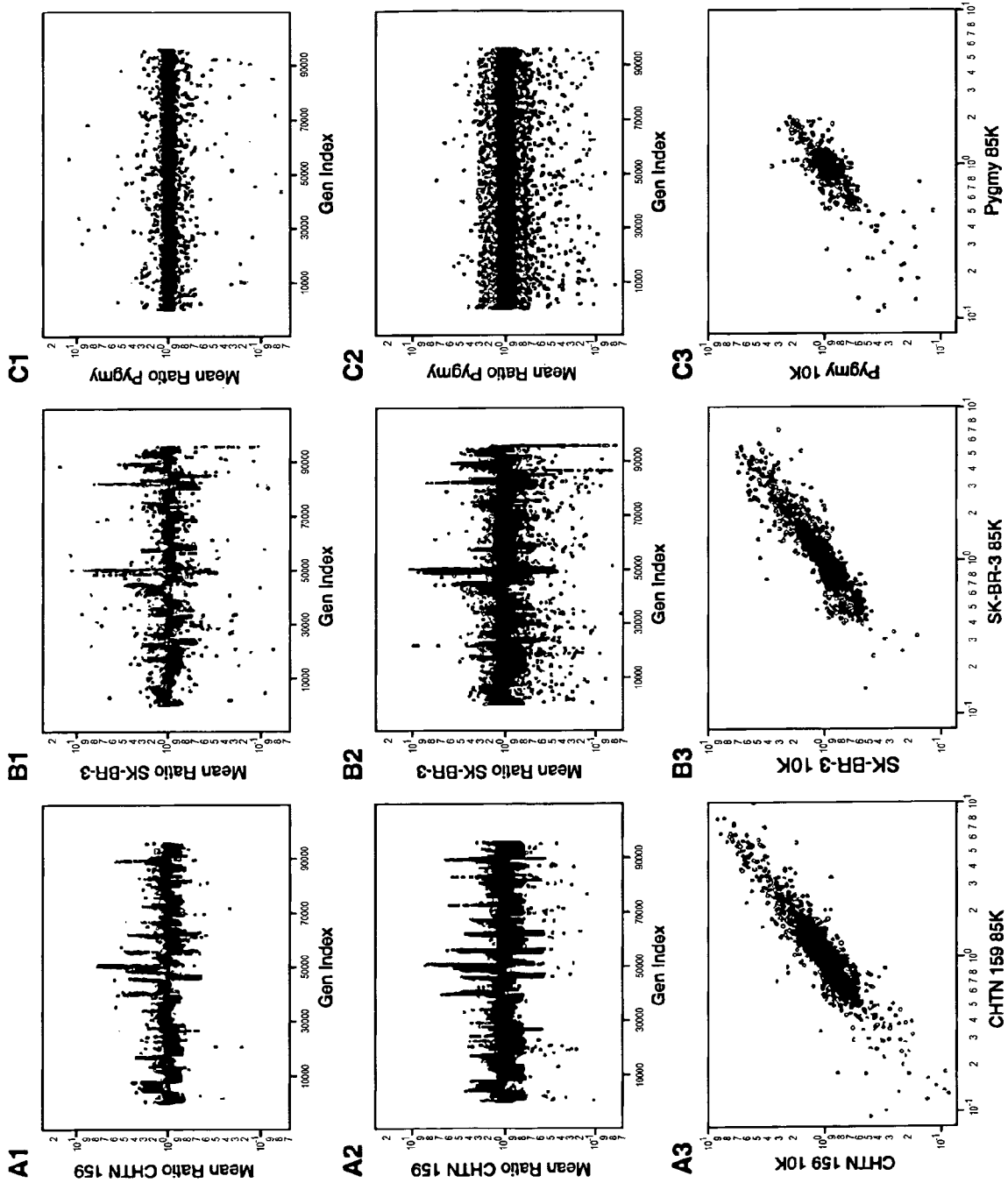

The oligonucleotide arrays of the invention readily detect large-scale genomic lesions, whether they are deletions or amplifications. FIGS. 2A1-A3, 2B1-B3, and 3C1-3C3 show the array hybridization data for three genomic comparisons: FIGS. 2A1-A3 compare aneuploid breast cancer cells to normal, diploid cells from the same biopsy (CHTN159) (the two sample representations were prepared from about 100 ng of DNA, each isolated from nuclei from aneuplid and diploid fractions separated by flow cytometry); FIGS. 2B1-B3 compare a breast cancer cell line (SK-BR-3) derived from a patient of unknown ethnicity to an unrelated normal male J. Doe (of mixed European and African parentage; see Example 2); and FIGS. 2C1-C3 compare cells from another normal male (African pygmy) vs. the same J. Doe. In each case, the samples were hybridized twice, with color reversal, and the geometric mean ratio (on a log scale) was plotted against the genome order of the oligonucleotide probes. Increased copy number (amplification) is indicated by a ratio above 1, and decreased copy number (deletion) by a ratio below 1. Data shown in FIGS. 2A1, 2B1 and 2C1 were obtained with the 10K print arrays. Data shown in FIGS. 2A2, 2B2 and 2C2 were obtained with the 85K photoprint arrays.

There were clear profiles to the cancer genomes. The profiles of the two breast cancer lines were distinct, but each showed large regions of amplification and deletion in the genome (FIGS. 2A1-A2 and 2B1-B2). In contrast, the profile of the normal-normal was essentially flat, indicating no large scale amplifications or deletions between these genomes (FIGS. 2C1-C2). These data confirm that the oligonucleotide arrays of the invention can detect large-scale genomic changes.

The results also indicate that there were many oligonucleotide probes detecting minor losses and gains in all three genomes (the two cancer genomes and the African male's genome). These losses and gains are shown as stand-alone dots in FIGS. 2A1-A2, 2B1-B2 and 3C1-C2, and are manifest in FIG. 2C2 (the normal-normal comparison) as a "shell" or zone of probes that approach the ratios of 0.5 and 2.0 throughout the genome. These losses and gains were likely the result of heterozygous BglII polymorphism between the individuals sampled.

Further, comparison between the 10K print format and the 85K photoprint format clearly demonstrates that, although they had different resolutions, both captured a similar view of the large-scale genomic features. We call probes "brothers" if they share complementarity to the same BglII fragment. Brothers do not necessarily have overlapping sequences, although they may overlap by up to half of their length, or may be complementary across their entire length. In FIGS. 2A3, 2B3 and 2C3, we plot the ratios of brother oligonucleotides from the 10K format (Y-axis) to ratios of their brother oligonucleotides from the 85K format (X-axis). There were in excess of 7,000 brother probes. There was remarkable agreement between the ratios of brother probes in the two formats for all three experiments, in spite of the facts that the probe sequences differed between formats, that their patterns of arraying were different, that the hybridization conditions differed, and the surfaces of the array were different. These data confirm the reproducibility of results obtained using arrays comprising oligonucleotides of the invention.

In addition, analysis of MOMA representations produced by cleavage with McrBC showed regions of the genome with altered methylation status between the cancer cell and normal cell genomes. Normalization to copy number differences in these regions using the BglII representation confirmed that the observed difference at many of these sites was due to a difference in methylation status and not in copy number.

Example 7

Automated Segmentation and Whole Genome Analysis

We also analyzed the data from smaller regions of the genome to map the variation seen in Example 6. For example, we analyzed the data from one chromosome at a time using a statistical segmentation algorithm that parses the probe ratio data into segments of similar mean after taking variance into account (termed circular binary segmentation (CBS); see Olshen and Venkatraman, Change-Point Analysis of Array-Based Comparative Genomic Hybridization Data, Alexandria, Va., American Statistical Association, 2002). The algorithm recursively identifies the best possible segmentation from each chromosome, rejecting or accepting each proposed split based on the probability that the difference in mean could have arisen by chance. This probability is determined by a randomization method. Due to its nonparametric nature, the algorithm prevented us from identifying aberrations recognized by fewer than three probes.

FIGS. 3A-D illustrate the output for this analysis on four chromosomes (chromosomes 5, 8, 17 and X in FIGS. 3A-D, respectively) of the cancer cell line SK-BR-3 using the 85K array. We observed similar segmentation profiles and segment means when we used the data from the 10K array. Further analysis of the data enabled us to determine the ploidy level of the cells.

Figure 4A:
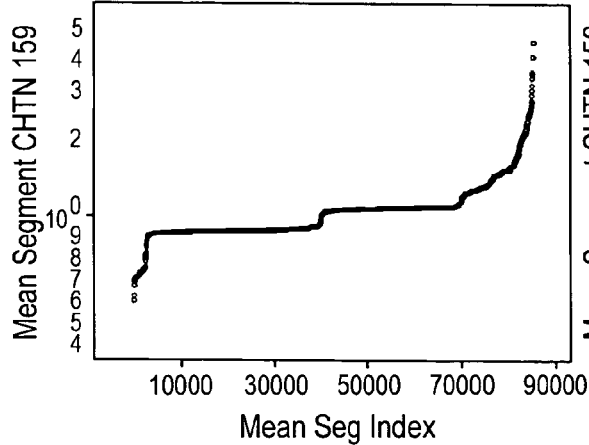
FIGS. 4A-4D show the mean segmentation calculated from the analysis of SK-BR-3 compared to the normal reference (FIG. 4A and FIG. 4B) and CHTN159 (FIG. 4C and FIG. 4D).
Figure 4B:
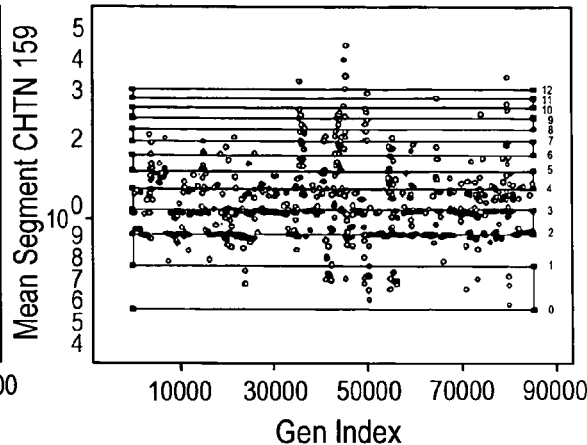
Figure 4C:
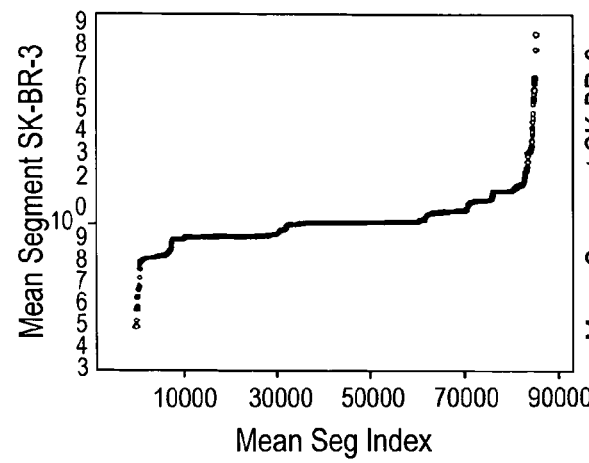
Figure 4D:
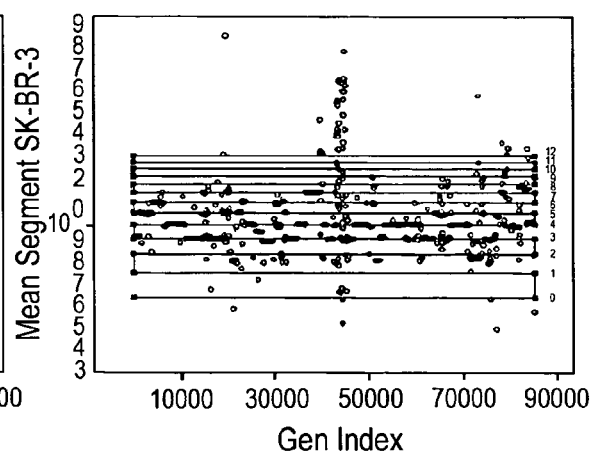

Once segmented, we assigned to each oligonucleotide the mean-ratio of the segment to which it belonged and plotted the mean-ratios in sorted order. These data are plotted for the cancer genomes of CHTN159 (FIG. 4A) and SK-BR-3 (FIG. 4C). The figures demonstrate that the segment mean-ratios within each genome were quantized, with major and minor plateaus of similar value. We deduced the copy number of these regions based on counting and the knowledge by flow analysis that CHTN159 was sub-triploid and SK-BR-3 was tetraploid. If each sample was roughly monoclonal, then the two major plateaus in CHTN159 would be two and three copies per cell, and the major plateaus SK-BR-3 would be three and four copies per cell.

We used the copy number calculated for the major plateaus to solve the ploidy and $S_N$ for each experiment. We used an equation:

$$R_M = (R_T \times S_N + 1)/(S_N + 1)$$

where $R_M$ was the mean measured ratio, $R_T$ was the true ratio, and $S_N$ was an experimentally derived character measuring "specific to non-specific" noise. We selected $R_M$ as the average of the probes of the segments in the plateau and set $R_T$ to $C_N/P$, where $C_N$ was the true copy number known from the plateau, and P was the ploidy of the tumor genome. The combination provided two equations and two unknowns, P and $S_N$. For the CHTN159 experiment (FIG. 4A), we calculated the ploidy P to be 2.60, and $S_N$ to be 1.13. For the SK-BR-3 experiment (FIG. 4C), we calculated that P was 3.93, and $S_N$ was 1.21.

We also used the equation to calculate what mean-ratios would be predicted for higher and lower copy numbers. We marked these predicted values on the respective graphs, from zero to a copy number of 12, with horizontal lines forming a "copy number lattice." The assigned mean-segment values for probes are displayed in genome order, embedded with the expected copy number lattice, in FIGS. 4B and 4D. The copy number lattice fits remarkably well the minor plateaus of the data, especially for the higher copy numbers.

Example 8

Analysis of Fine-Scale Genomic Lesions

We also analyzed the data to determine precise breakpoints in individual chromosomes that had amplifications or deletions. Our analysis demonstrated that the arrays of the invention can be used to identify genomics lesions at the resolution of individual genes. Accordingly, data obtained from the arrays may be used to predict the impact of aberrations in particular genes on conversion of a normal cell to a cancerous one.

Figure 3A:
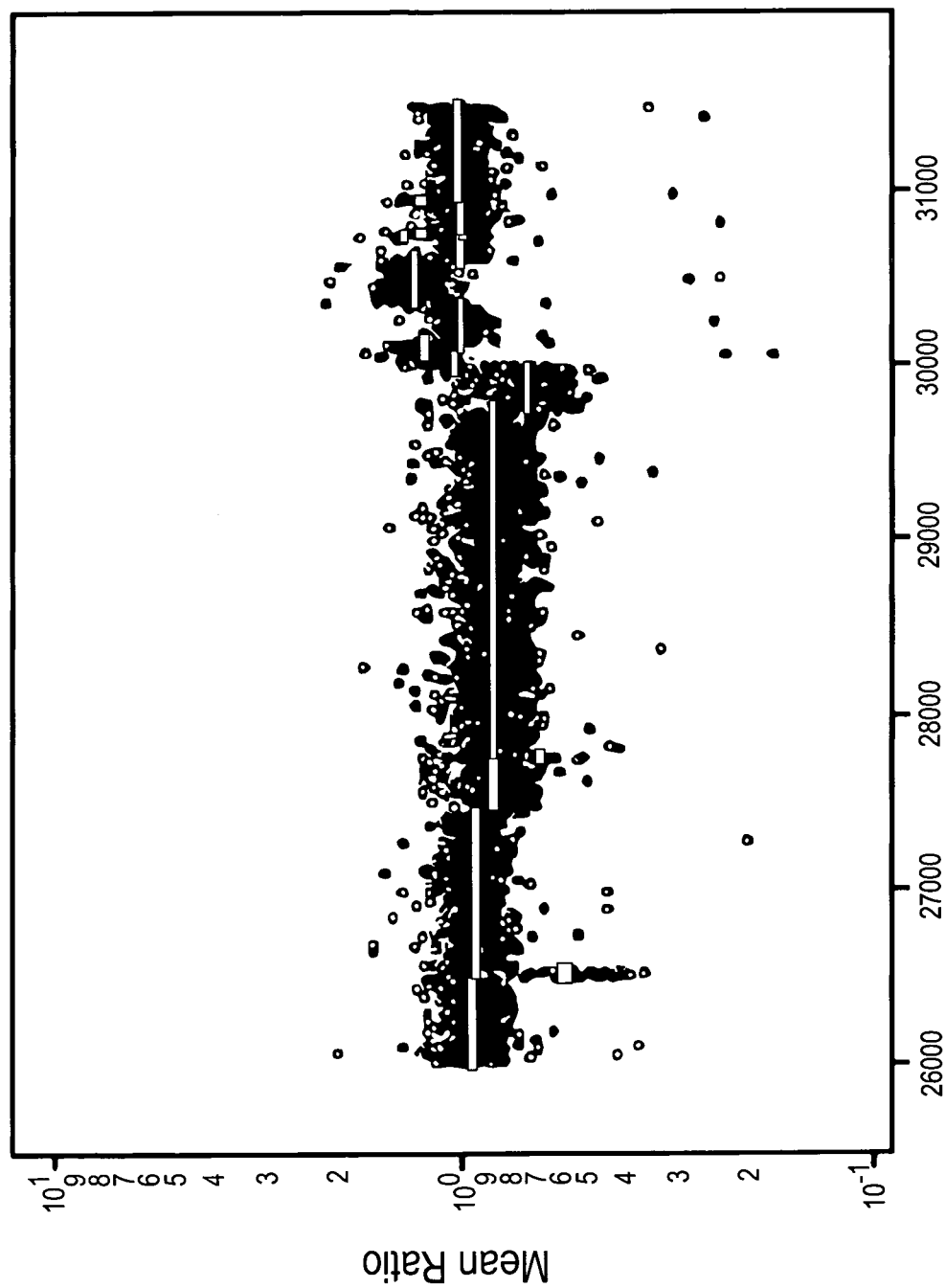
FIGS. 3A-3D show several chromosomes with varying copy number fluctuations from analysis of the tumor cell line SK-BR-3 as compared to the normal reference. The Y-axes (Mean Ratio) represents the mean ratio of two hybridizations in log scale. The X-axes (Gen Index) is an index of the genomic coordinates.
Figure 3B:
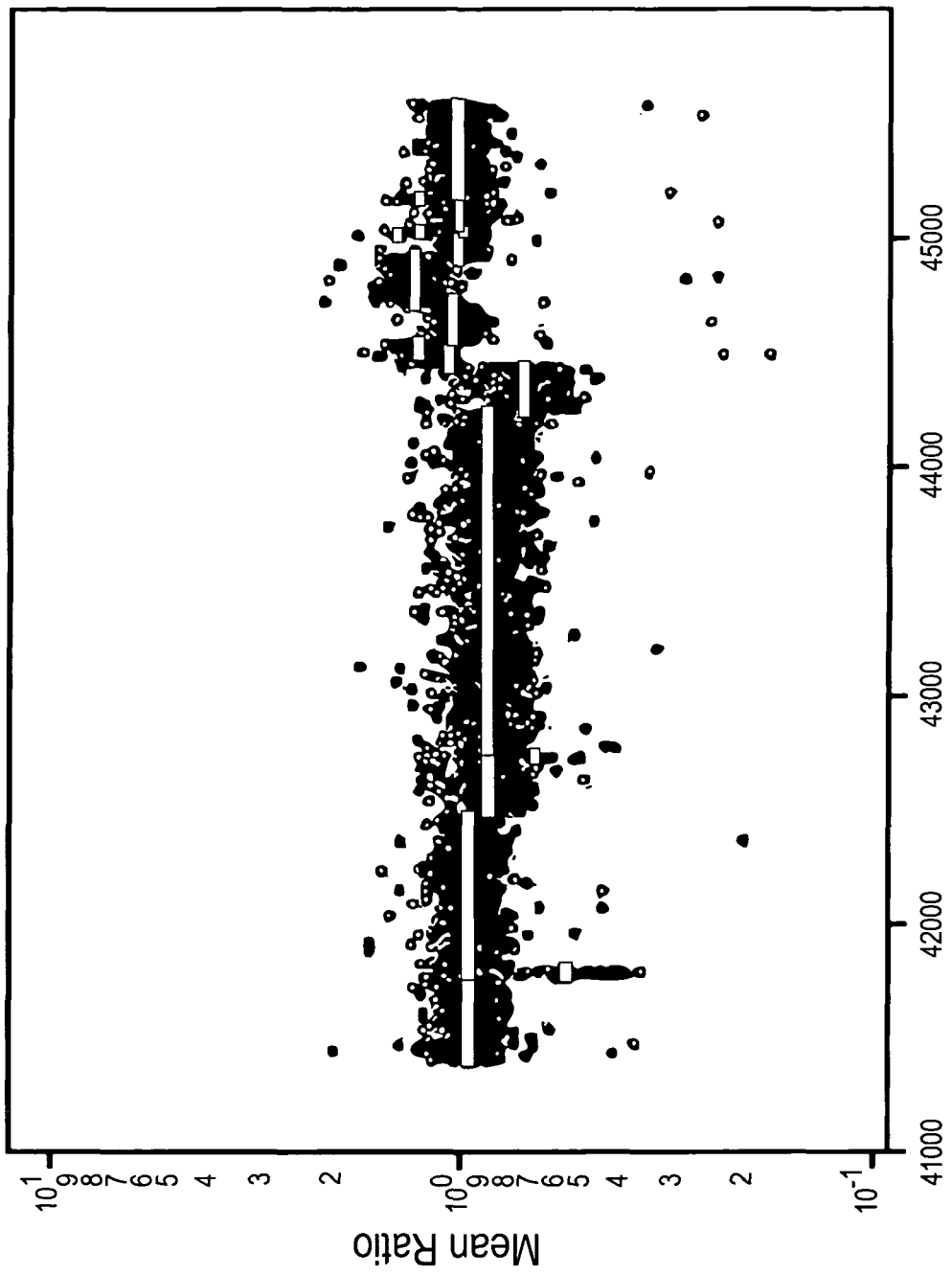
Figure 3C:
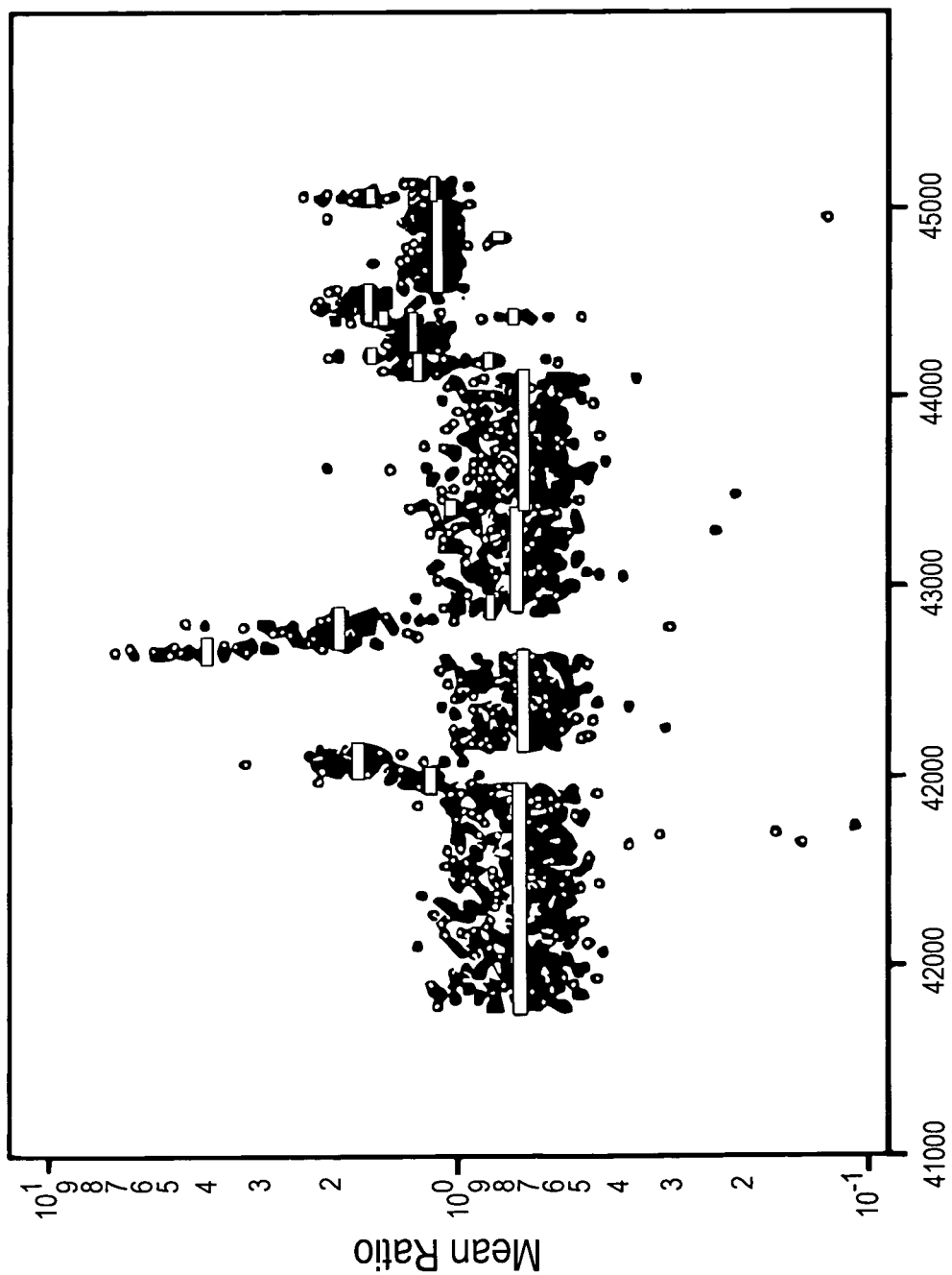
Figure 3D:
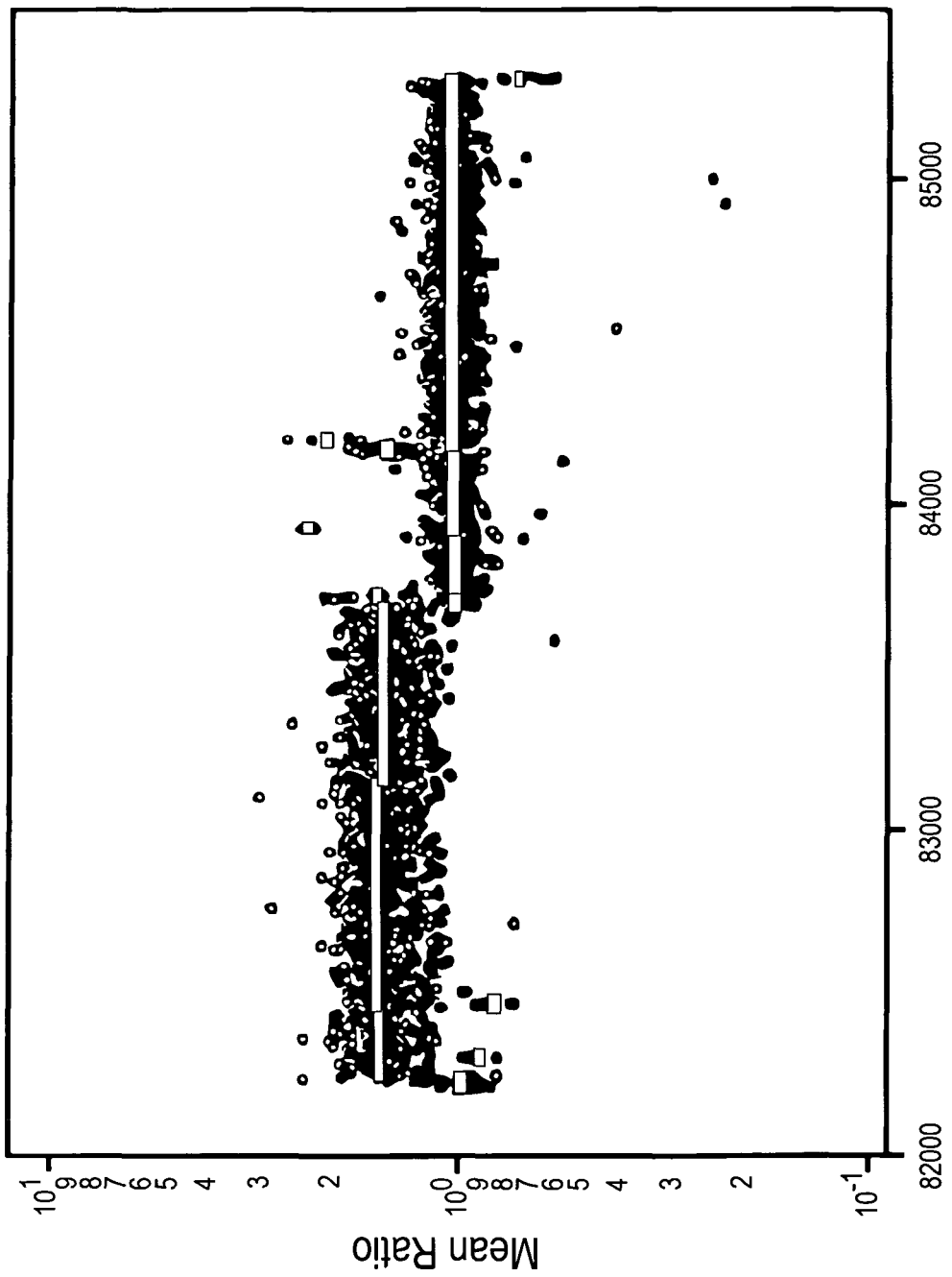
Figure 5A:
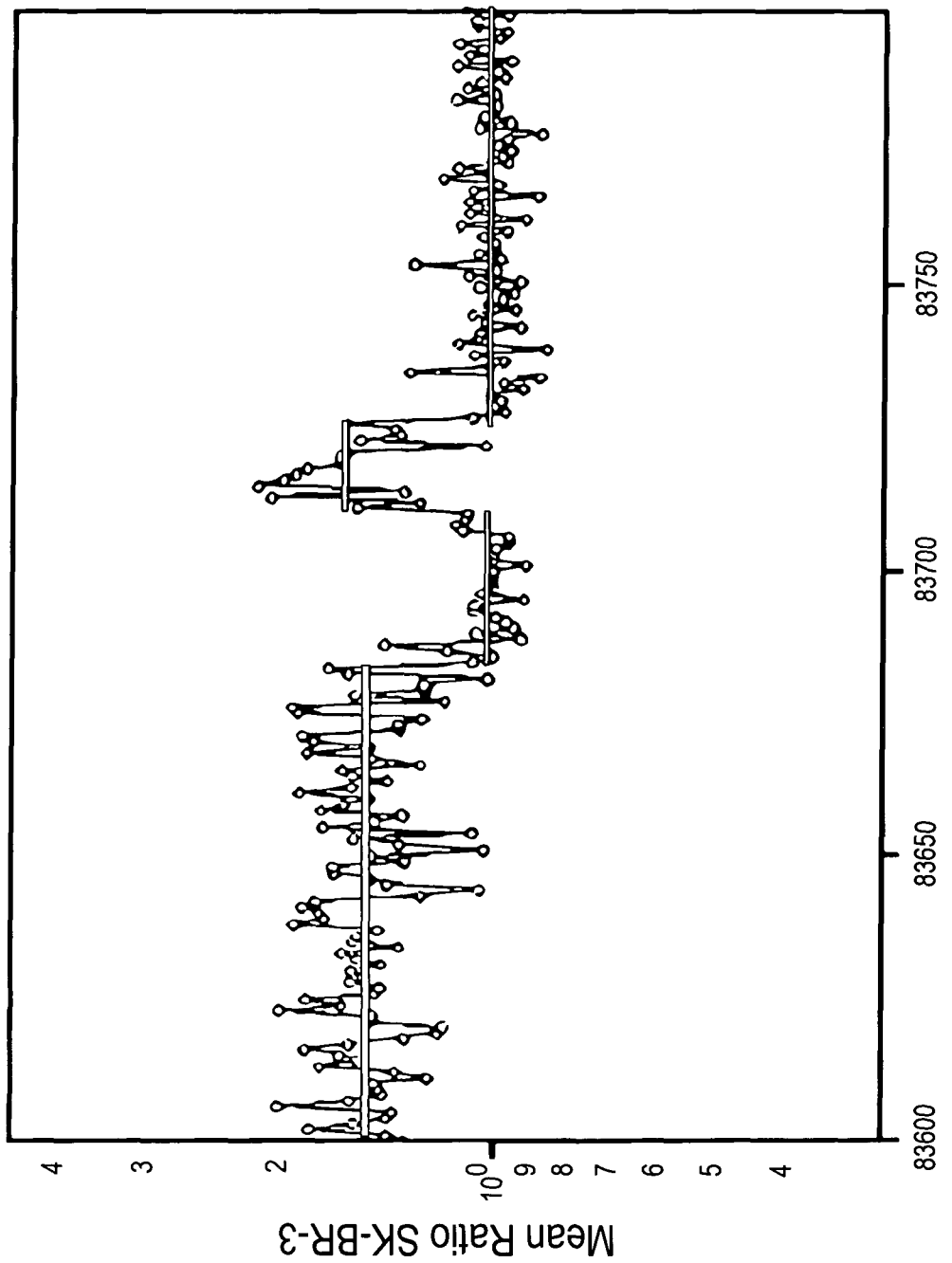
FIGS. 5A-5D graph on the Y-axis (Mean Ratio SK-BR-3) the mean ratio of two hybridizations of SK-BR-3 compared to a normal reference in log scale. The X-axis (Gen Index) is a genomic index.

We first analyzed a region of a break in the X chromosome, seen in FIG. 3D. SK-BR-3 cells, which were derived from a female, were compared to cells of an unrelated male. We expected that probes in chromosome X would have elevated ratios. This was the case through much of the long arm of chromosome X. But in the midst of Xq13.3, there was a sharp break in copy number over a region spanning 27 kb and ratios near one were observed for the remainder of the chromosome (FIG. 5A). Thus, it was possible to draw boundaries of genetic lesions from array data by segmentation. We have observed many other instances of sharp copy number transitions that must break genes.

There were three to four narrow amplifications in the SK-BR-3 genome, each containing two or fewer genes, among which were transmembrane receptors.

Figure 5B:
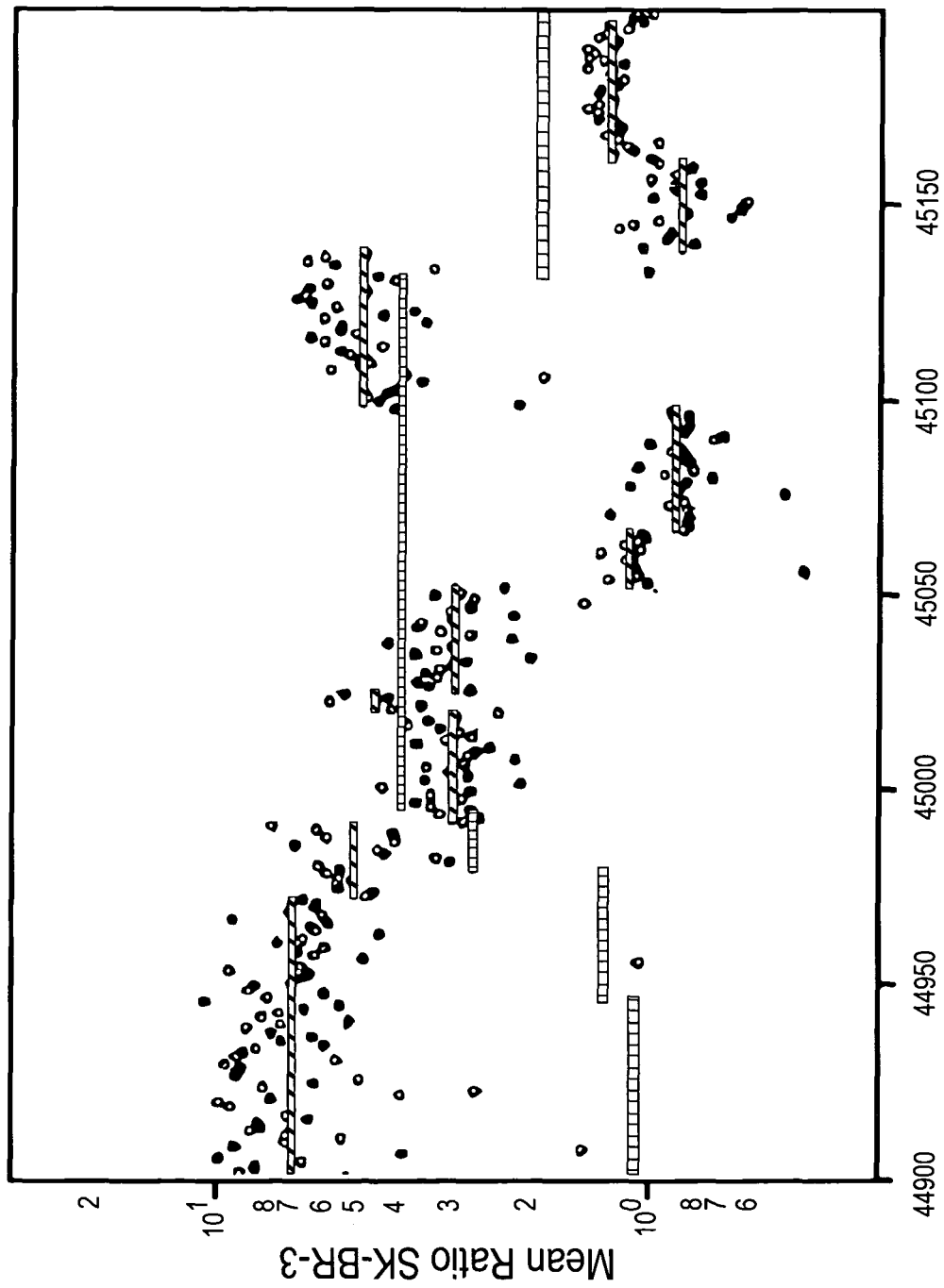

We then analyzed the data from chromosome 8 (FIG. 3B), which had an abundance of aberrations, including broad, distinct regions of amplification (FIG. 5B). The rightmost peak was approximately a one-megabase stretch, comprised of thirty-seven probes (probe coordinates 45099-45138, June genome coordinates 126815070-128207342). Yet it contained a single well characterized gene, c-myc.

There was a second broad peak in SK-BR-3, ascending to the left of the c-myc peak, and off the graph (FIG. 5B). This broad peak had a broad shoulder on its right (probe coordinates 44994-45051, June genome coordinates 123976563-125564705), with a very narrow peak in its midst. We overlaid on this the segmentation data from the tumor genome, CHTN159, which had an even broader peak encompassing c-myc (probe coordinates 44996-45131, June genomic coordinates 124073565-127828283). The peak in CHTN159 also encompassed the shoulder of the second SK-BR-3 peak (FIG. 5B). Thus the shoulder may contain candidate oncogenes that merit attention. Within that region, at the narrow peak, we found TRC8, the target of a translocation implicated in hereditary renal carcinoma (Gemmill et al. Proc. Natl. Acad. Sci. USA 95:9572-7 (1998)). These results illustrate the value of coordinating data from multiple genomes, and the need for automated methods for analyzing multiple data sets.

Figure 5C:
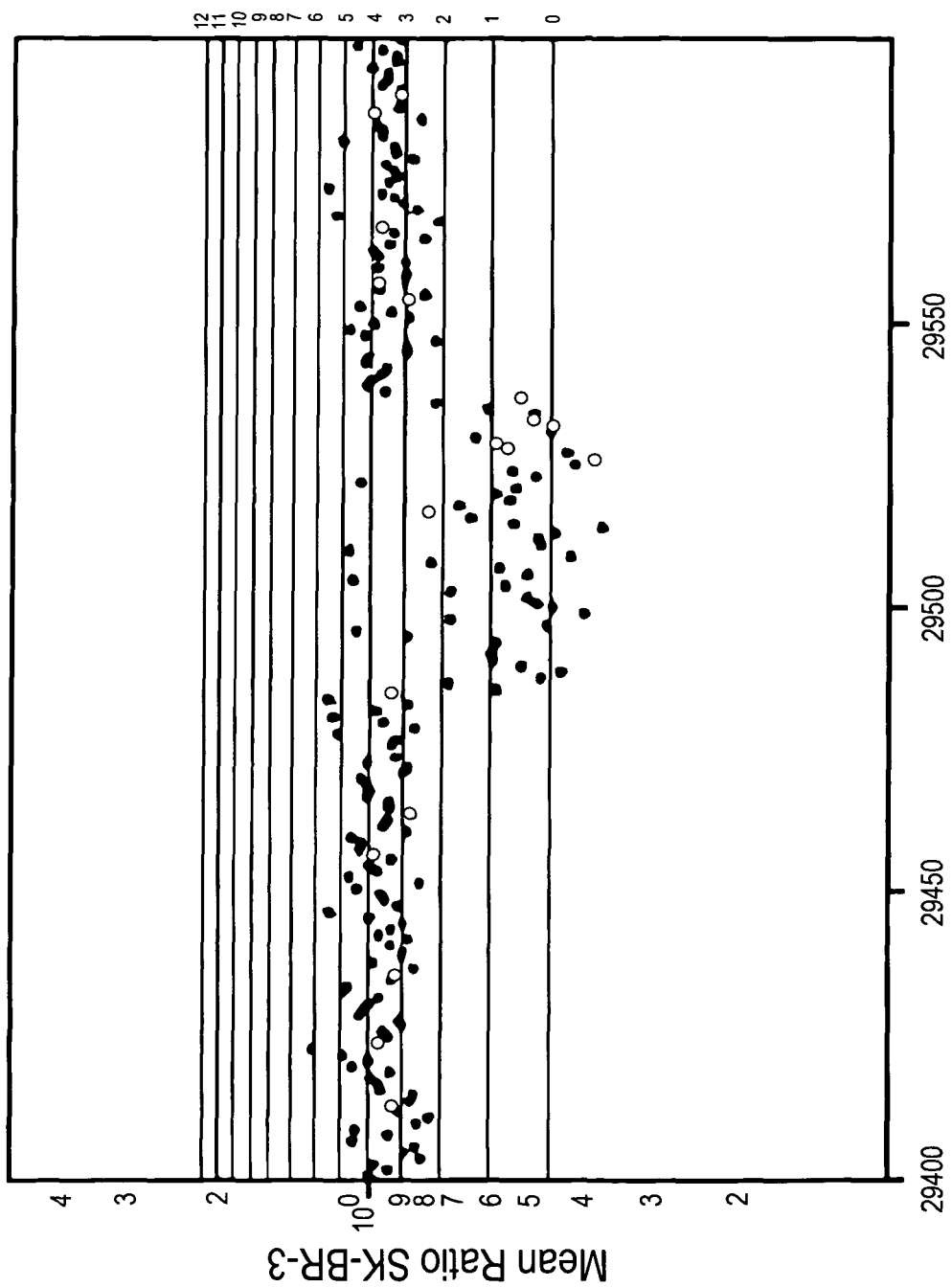

We also analyzed a narrow deletion on chromosome 5. FIG. 5C shows the results of a combined 10K (empty circles) and 85K (filled circles) analysis overlaid on a copy number lattice. A deletion was evident at both the 10K and 85K resolutions (probe coordinates 29496-29540, June genomic coordinates 14231414-15591226), but the boundaries were much more clearly resolved at 85K. This region contained TRIO, a protein having a GEF domain, an SH3 domain, and a serine threonine kinase domain (Lin and Greenberg, Cell 101:230-42 (2000)); ANKH, a transmembrane protein (Nurnberg et al., Nat. Genet. 28:37-41 (2001)); and FBXL, a component of the ubiquitin ligase mediated protein degradation pathway (Ilyin et al., Genomics 67:40-47 (2000)).

Figure 5D:
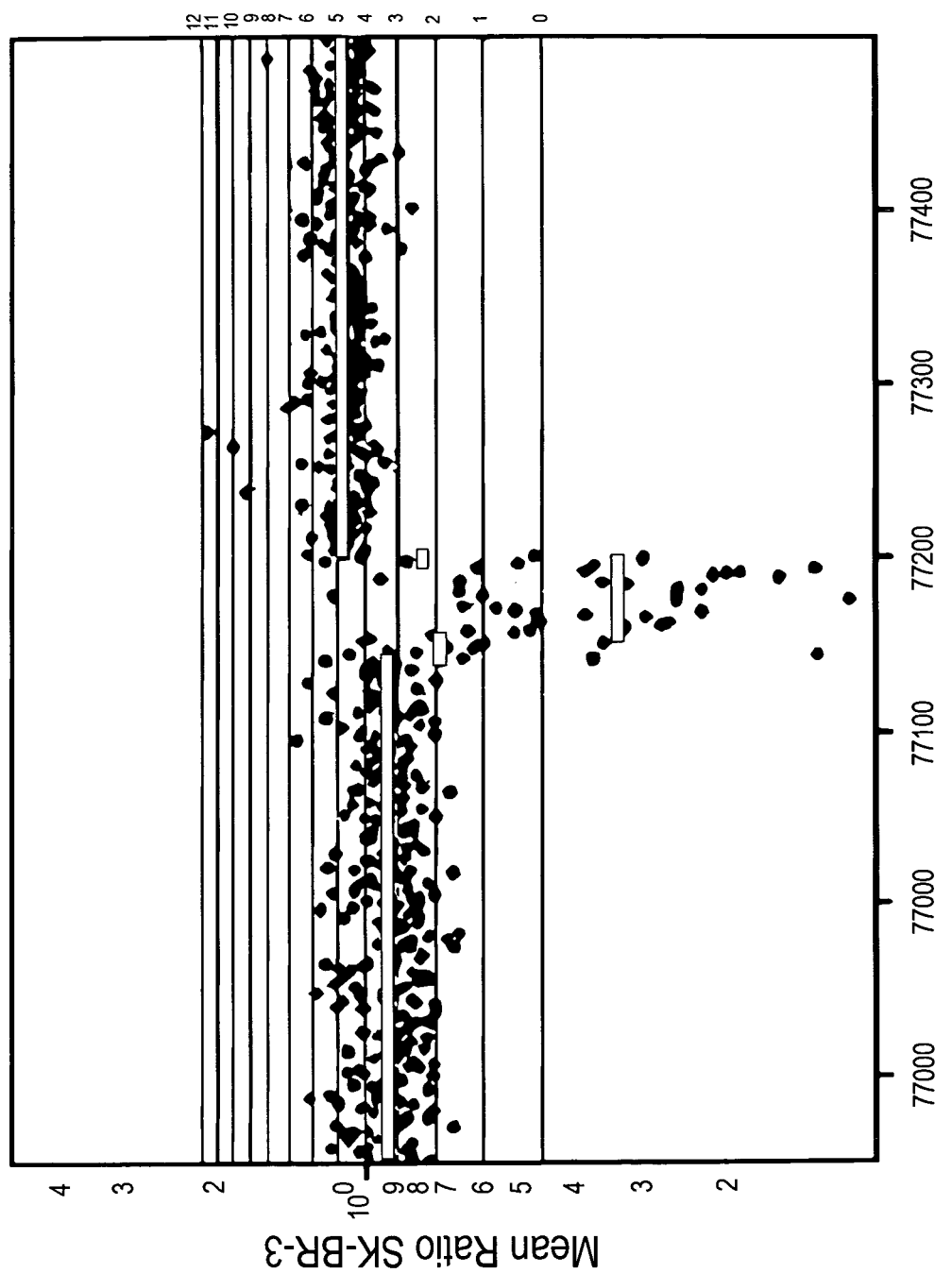

Finally, we analyzed a region of homozygous loss on chromosome 19 affecting a cluster of zinc finger proteins (FIG. 5D; probe coordinates 77142-77198, June genomic coordinates 21893948-24955961). Some of these genes may encode transcription factors, whose deletion may have role in tumorigenesis. We observed an abundance of narrow hemizygous and homozygous lesions, some of which might be attributable to normal variation. See Example 9.

Example 9

Examining "Normal" Genomic Variation

We also used the oligonucleotide arrays and methods of this invention to analyze copy number variation between two normal genomes and observed differences resulting from polymorphic variation. This analysis is important, e.g., in situations where a tumor DNA sample cannot be matched against normal DNA and an unrelated normal DNA is used as a reference because differences observed may be the result of polymorphic variation. This variation can be of two sorts, point sequence variation of the sort that creates or destroys a BglII fragment, e.g., SNPs, or actual copy number fluctuation present in the human gene pool. The former has limited impact on analysis using the arrays of the invention as it will produce scattered "noise" that can largely be filtered by statistical means.

In FIG. 6A (combined data from the 10K and 85K datasets), we demonstrate that a mild filtration algorithm (if a ratio was the most deviant of the surrounding four, we replaced it with the closer ratio of its two neighbors) can minimize the impact of point sequence variation and detect instances where there is actual copy number variation. The cloud of scattered polymorphisms present in an unfiltered sample (e.g., FIG. C2) is lifted in this presentation of the data revealing non-random clusters of deviant probe ratios, indicating large-scale genomic differences between normal individuals.

Figure 6B:
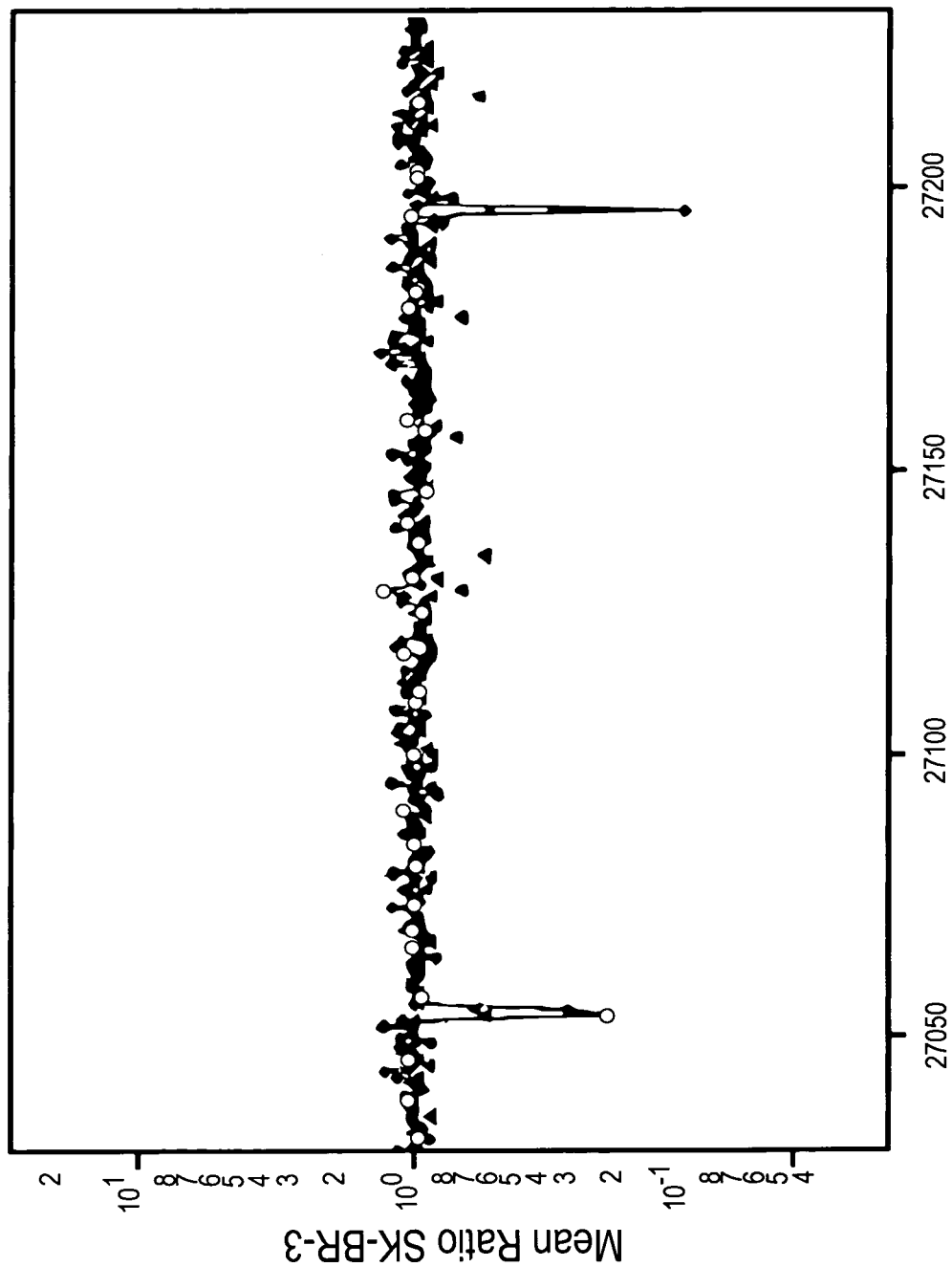

Polymorphic variation of the scattered variety can also be filtered by serial comparison of experiments. For example, FIG. 6B shows data from SK-BR-3 compared to normal donor, J. Doe, the 85K ratios displayed in filled circles, and the 10K in empty circles. On the same graph we display the ratios of J. Doe compared to another normal, DNA from an African pygmy, in green triangles. We see three probes of extreme ratio in the SK-BR-3-normal hybridization that can be identified as polymorphisms by comparison to hybridization between the two normal individuals. The simplest interpretation of these data is that J. Doe is +/+, pygmy+/− and SK-BR-3−/− where + designates the presence of a small BglII fragment (most likely a SNP at a BglII site). In general, pairwise comparisons of three genomes allow interpretable calls of allele status. Thus, these kinds of data are especially useful when a malignant genome cannot be paired to a matched normal.

Polymorphism in copy number, however, presents a different sort of problem. FIG. 6A demonstrates large regional differences in copy number in the normal-normal comparison. We applied segmentation analysis to these data and identified multiple regions that display altered copy number between the two normal individuals. We observed about a dozen variant regions in any normal-normal comparison. They stretch from one hundred kilobases to greater than a megabase in length, can occur anywhere but are more frequently observed near telemeres and centromeres, and often encompass known genes.

Figure 6C:
Figure 6D:
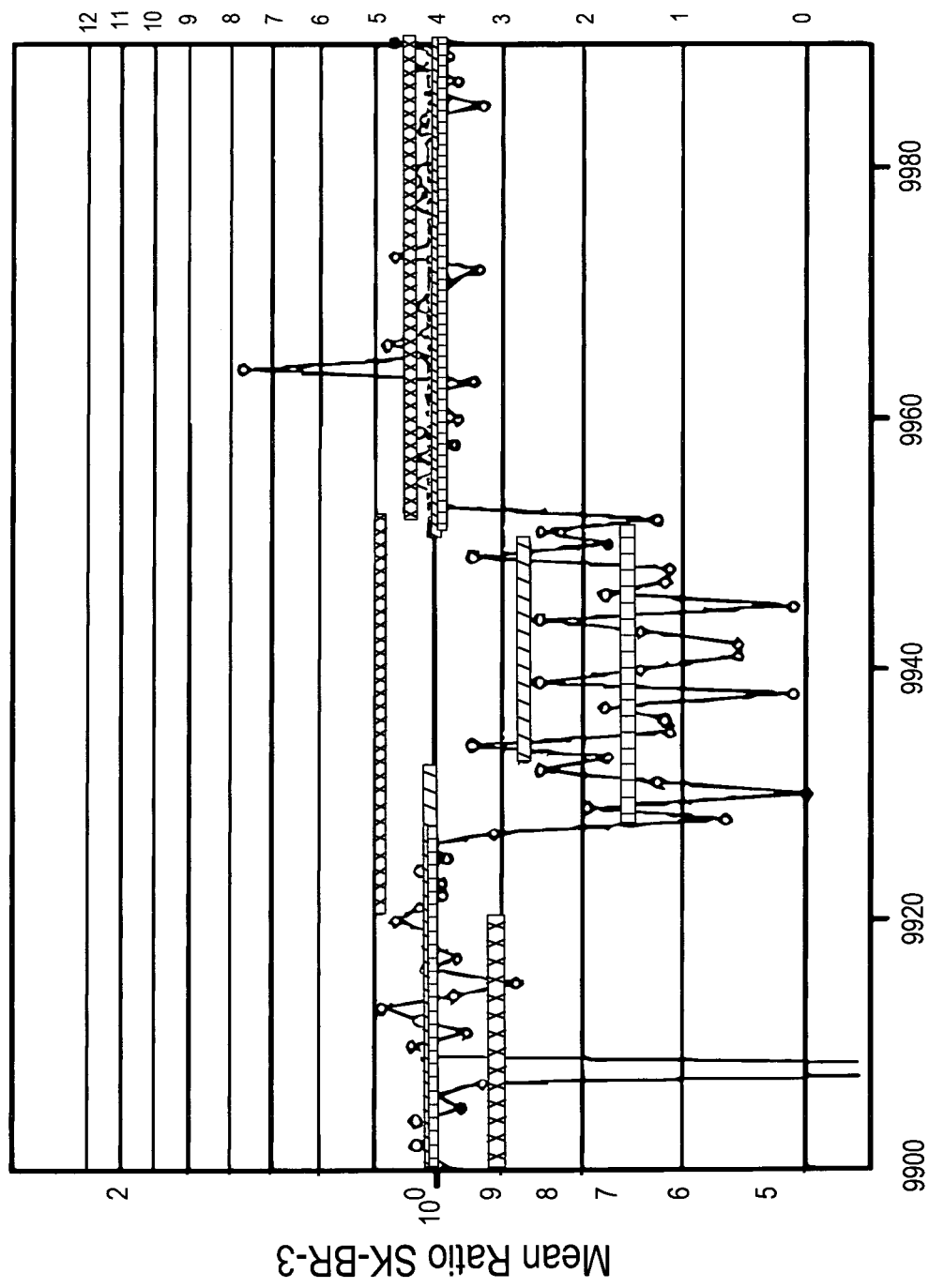

Close inspections of two such regions are displayed in FIG. 6C and FIG. 6D, with ratios as connected circles and segmentation values as lattice. In FIG. 6C, the abnormal region is 135 kb on chromosome 6p21 (probe coordinates 32518-32524, June genomic coordinates 35669083-35804705), and encompasses three known genes. In FIG. 6D, the region is a 620 kb region from chromosome 2p11 (probe coordinates 9927-9952, June genomic coordinates 88787694-89385815) that contains a number of heavy chain variable regions.

We analyzed the impact of the normal-normal variation on the interpretation of cancer-normal data. In FIG. 6C and FIG. 6D we have overlain the segmentation values from the analysis of SK-BR-3 in diagonal and vertical hatch, respectively. The copy number lattice for SK-BR-3 is plotted as lattice. FIG. 6C illustrates a region in SK-BR-3 that would be called a deletion in comparison to the normal. In SK-BR-3 the flanking region occurs at a copy number that we judge to be two copies per cell, and within that region, copy number becomes reduced to one. But the same region appears in the comparison of pygmy DNA to that normal. In FIG. 6D we observe an analogous condition on chromosome 2p11. In FIG. 6D we have also plotted segmentation data from the tumor. This region is evidently abnormal there as well.

Example 10

Annotation of a Genome of a Portion Thereof

The following examples are meant to illustrate uses of the search engine. Suitable modifications and adaptations of the described conditions and parameters normally encountered in the art which are obvious to those skilled in the art are within the spirit and scope of the present invention.

The search engine of the present invention can be used to perform computations on a genome or on subsets of a genome (e.g., a chromosome). In performing these computations, several regions having high word counts are found which are not detected by search tools such as Repeat Masker. It has been shown that the database of repeats used by Repeat Masker does not include region specific or chromosome specific repeats. Using the search engine described above in section VII, such repeats are easily found because exact match counting can form the basis for set algebra of the genome. In particular, a subset of the genome can be made into transform strings, which are examined to find chromosome specific repeats.

A transform string from chromosome 1 was annotated with the word counts within itself and within the entire genome. A search was performed to look for contiguous regions of chromosome 1, at least 100 bp in length, with high 18-mer counts in which the exact matches were found to derive mainly from chromosome 1. Such regions were readily found, ranging in length from 100 bp to 35 kb. Focusing on one such region, it was observed that its mer terrain was nearly a step function, composed of shorter sequences each with a signature modal frequency and length. The chromosome-specific regions containing one of these signature regions were collected and a family of chromosome 1 specific sequences was quickly identified. The chromosome 1 specific region was selected by identifying 18 mers whose chromosome 1 counts exceeded 90% of their whole genome counts, these 18 mers were strung together to create the chromosome specific repeat. In addition, the space between the 18 mers that were strung was not allowed to exceed 100 base pairs. It was found at least once that this repeat has been annotated as overlapping a RefSeq gene (accession number NM_015383), with many exons that together encode a large predicted protein sequence having low homology to myosin.

The same process by which chromosome specific repeats are identified can be applied to finding repetitive DNA throughout the genome, including those that are not recognized by Repeat Masker or other programs.

Example 11

Probe Design Using the Mer Engine

The above-mentioned search engine can be used in probe design. Probes are generally useful for their ability to hybridize specifically to complementary DNA, and therefore one of the primary objectives in probe design is to minimize cross hybridization. Previous probes designing applications have used repeat masking to exclude repeat regions from consideration. This type of solution is problematic, in that it does not provide protection from regions that are repetitive such as chromosome specific repeats, and it excludes "repetitive" regions that are unique.

While rules for hybridization between imperfectly matched sequences are not well understood, it is known in the art that probes that have exact "small" matches to multiple regions of the genome should preferably be avoided. Previous probe applications have chosen probes that minimize aggregate exact 12-mer match counts, but for genomic probes, these methods are inadequate. First, it is unclear that exact matches of 12-mers have any effect on hybridization under normally stringent annealing conditions. Nor do 12-mer counts predict homology, let alone uniqueness in the genome. In fact, a comparison of 15-mer counts to the geometric mean of counts from their constituent 12-mers yielded a poor correlation between two sequences that are essentially unique.

A general protocol for probe design using the mer-engine is described as follows. First, the genome is annotated according to a particular length mer such that sufficiently long stretches of uniqueness are found (i.e., candidate probes). Second, these candidate probes are annotated using at least one predefined length mer, preferably of a length shorter than the mer length used to find the candidate probes. One of the candidate probes is selected as the probe based on the minimum aggregate mer-counts of the predefined shorter lengths.

Following the above-mentioned protocol, 70-mer candidate probes were selected from small BglII fragments, using uniqueness data obtained from 21-mer counts. Within these candidate probes, a 70-mer was selected with the lowest sum of 15-mer counts, with a cut off value of about 900. Additional criteria that eliminated runs of single nucleotides and severe base composition bias were also applied to assist in determining which candidate probe to choose. Selected probes were synthesized and printed on glass to test their performance in micro-array hybridization conditions. It was found that substantially all the probes performed at or above specified performance criteria. More particularly, a success rate of about 70% to about 98% was achieved with the probes designed using the above-mentioned protocol, where success is defined as having a substantial (e.g., large) signal/noise ratio.

BLAST was used to test whether the selected probes were unique within a particular published genome sequence. 30,000 such probes were tested using the default parameters for MegaBLAST (filtration of simple sequence was turned off). It was found that greater than 99% of the selected probes were unique within the genome.

Example 12

Pseudo Code Representation of Algorithm

Figures 12A, 12B:
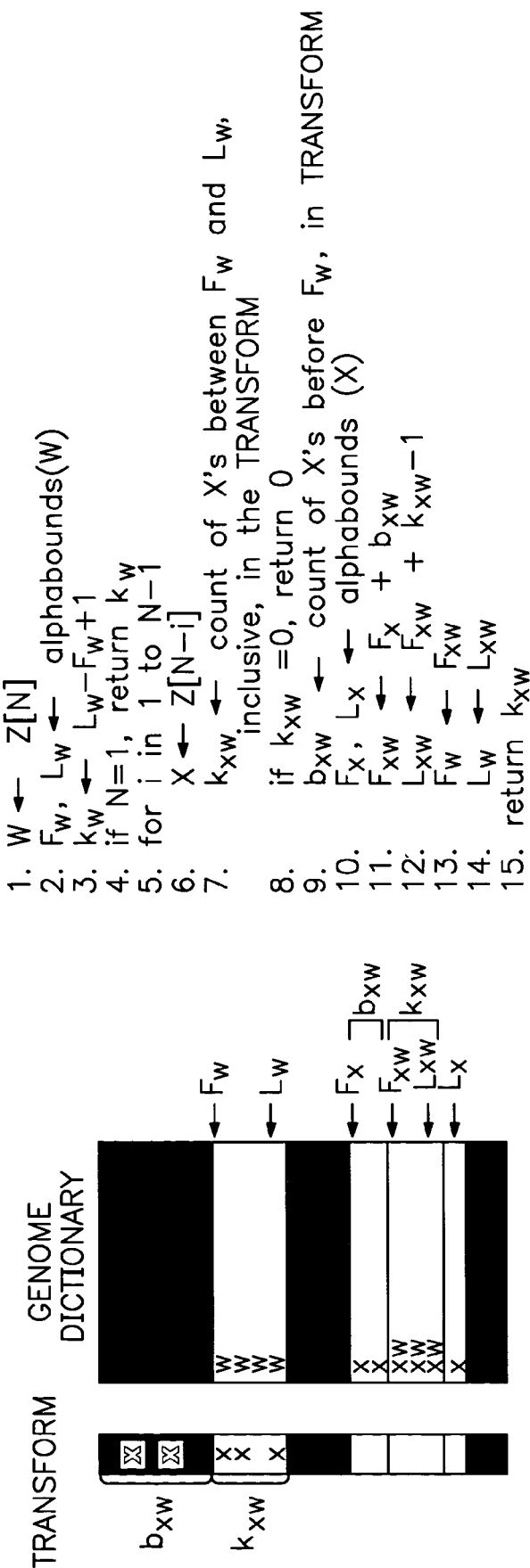
FIG. 12A shows a graphical representation of the variables and data structures used in connection with the algorithm according to certain embodiment of the invention.
FIG. 12B shows a pseudo code representation of the algorithm according to certain embodiments of the invention.

To further illustrate how the algorithm can be implemented to perform a word counting function, refer to FIGS. 12A and 12B. FIG. 12A graphically defines variables and data structures used by the algorithm and FIG. 12B shows a pseudo code representation of the algorithm. As indicated above in section VII, the transform can be used as a navigational tool for a "virtual" Genome Dictionary or suffix array. In the simplest case, assume that it is desired to determine whether a substring occurs in the genome, and if so, in how many copies. In this case, assume that the substring is the single character, "X." All occurrences of X can be viewed in the dictionary as a block (e.g., search region) where Fx and Lx are the indices of the first and last occurrence of X. Fx and Lx can be derived from the alphabounds data structure. The size of this block (e.g., search region) is kx=Lx−Fx+1, is also the number of occurrences of X. Note that this number can be determined by counting the number of occurrences of X in the transform.

In a more difficult case, such as when two or more character words are to be counted, the Fx, Lx, and kx of each character X in the genome need to be determined. In other words, the Fx and Lx for each character X is stored in the data structure called alphabounds. Once the alphabounds data structure is constructed, the algorithm can proceed to count the number of times a particular word, Z, occurs in the genome. Assume W is a suffix of Z, W exists in the genome, and the alphabounds (e.g., Fw and Lw as shown in FIG. 12A) of W are known. Next, a determination needs to be made as to whether XW exists as a substring, where X is the character preceding W in Z. In addition, the start and end indices (e.g., Fxw and Lxw) of the XW block need to be determined.

If and only if X occurs in the transform between Fw and Lw, then XW exists as a substring in the genome. Furthermore, the number of X's in the "W block" of the transform, indicated as kxw, is the word count of the substring XW in the genome. The start and end indices of XW can be completed using: 1) Fxw=Fx+bxw; and 2) Lxw=Fxw+kxw−1, where bxw is the number of words beginning with X in the Genome Dictionary that occur before XW. bxw can be determined by counting the number of Xs that occur before the W block of the transform.

This procedure is reiterated, lengthening the suffix one character at a time, stopping if the suffix does not exist in the Genome Dictionary. If the suffix W encompasses the entire word, Z, kw is the number of occurrences of Z in the genomic string. An outline of this procedure is outline in pseudo code, as shown in FIG. 12B. With respect to FIG. 12B, Z is a string of length N, composed of characters from the genome alphabet, and the alphabounds data structure contains the indices of the first and last occurrences in the genome dictionary for each character in the genome alphabet.

Unless otherwise defined, all technical and scientific terms used herein have the same meaning as commonly understood by one of ordinary skill in the art to which this invention belongs. All publications and other references mentioned herein are incorporated by reference in their entirety. In case of conflict, the present specification, including definitions, will control. The materials, methods, and examples are illustrative only and not intended to be limiting. Throughout this specification, the word "comprise," or variations such as "comprises" or "comprising" will be understood to imply the inclusion of a stated integer or group of integers but not the exclusion of any other integer or group of integers.

What is claimed is:

1. A method of identifying an oligonucleotide, the method comprising
   (A) cleaving a genome of at least Z basepairs in silico with a restriction enzyme to generate a plurality of predicted nucleic acid molecules,
   (B) generating a virtual representation of said genome by identifying predicted nucleic acid molecules, wherein each predicted nucleic acid molecule has a length of 200-1,200 basepairs, inclusive;
   (C) calculating the following:
      (i) $Z \geq 1 \times 10^8$;
      (ii) $300 \geq K \geq 30$;
      (iii) the integer closest to $(\log_4(Z)+2) \geq L_1 \geq$ the integer closest to $\log_4(Z)$;
      (iv) X is the integer closest to $D_1 \times (K-L_1+1)$;
      (v) Y is the integer closest to $D_2 \times (K-L_1+1)$;
      (vi) $1.5 \geq D_1 \geq 1$; and
      (vii) $1 > D_2 \geq 0.5$;
   (D) selecting oligonucleotides each having a length of K nucleotides, inclusive, and each with at least 90% sequence identity to a predicted nucleic acid molecule in (B);
   (E) identifying all of the $L_1$-mers occurring in each oligonucleotide; and
   (F) selecting one or more oligonucleotides that have a sum total value of $L_1$-mer counts in the virtual representation of no fewer than Y and no more than X, wherein an $L_1$-mer is a subregion of the oligonucleotide having a length of $L_1$ nucleotides, wherein an $L_1$-mer count is the number of times the sequence represented by one $L_1$-mer occurs in the genome, and wherein the sum total value of $L_1$-mer counts is the sum of every $L_1$-mer count of the oligonucleotide occurring in the virtual representation.

2. The method of claim 1, wherein the oligonucleotide is a nucleic acid probe.

SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:
      Illustrative polynucleotide sequence

<400> SEQUENCE: 1
agacagtcat                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:
      Illustrative polynucleotide sequence

<400> SEQUENCE: 2
acgtcagtca                                                            10

3. The method of claim 1, wherein K is 40 to 70.

4. The method of claim 1, wherein the virtual representation has no more than R % of the complexity of said genome, wherein 70%≥R %≥1%.

5. The method of claim 4, wherein R % is 1 to 2.5%.

6. The method of claim 1, wherein Z is at least $1 \times 10^9$.

7. The method of claim 1, wherein the genome is a mammalian genome.

8. The method of claim 1, wherein the genome is a human genome.

9. The method of claim 1, wherein $D_1$ is 1.

10. The method of claim 1, wherein $D_2$ is 0.5.

11. The method of claim 1, wherein $L_1$ is 15, 16, 17, 18, 19, 20, 21, 22, 23 or 24.

12. The method of claim 1, wherein said representation is obtained with two or more different restriction endonucleases.

\* \* \* \* \*